US007547767B2

(12) United States Patent
Yang et al.

(10) Patent No.: US 7,547,767 B2
(45) Date of Patent: Jun. 16, 2009

(54) GROWTH ARREST SPECIFIC GENE 6 PEPTIDES, ANTIBODIES, COMPOSITIONS, METHODS AND USES

(75) Inventors: Jing Yang, Ambler, PA (US); George Heavner, Malvern, PA (US); Robert Jordan, Thornton, PA (US); Jill Giles-Komar, Downingtown, PA (US); Ray Sweet, Bala Cynwyd, PA (US)

(73) Assignee: Centocor Ortho Biotech Inc., Horsham, PA (US)

( * ) Notice: Subject to any disclaimer, the term of this patent is extended or adjusted under 35 U.S.C. 154(b) by 39 days.

(21) Appl. No.: 11/602,865

(22) Filed: Nov. 21, 2006

(65) Prior Publication Data
US 2007/0128200 A1 Jun. 7, 2007

Related U.S. Application Data

(62) Division of application No. 10/671,019, filed on Sep. 24, 2003, now abandoned.

(60) Provisional application No. 60/413,250, filed on Sep. 24, 2002.

(51) Int. Cl.
*C07K 16/46* (2006.01)
(52) U.S. Cl. .............. 530/388.1; 424/139.1; 530/387.1
(58) Field of Classification Search ..................... None
See application file for complete search history.

(56) References Cited

U.S. PATENT DOCUMENTS

| 5,538,861 | A | 7/1996 | Schneider et al. |
| 5,585,269 | A | 12/1996 | Earp, III et al. |
| 5,955,420 | A | 9/1999 | Chen et al. |
| 6,033,660 | A | 3/2000 | Mather et al. |
| 6,169,070 | B1 | 1/2001 | Chen et al. |
| 6,211,142 | B1 | 4/2001 | Hammonds et al. |
| 6,455,304 | B1 * | 9/2002 | Weigel et al. ............ 435/320.1 |

FOREIGN PATENT DOCUMENTS

WO    WO 99/49894 A1    10/1999
WO    WO 00/53754 A1     9/2000

OTHER PUBLICATIONS

Kuby, Immunology, 2nd Ed, 1994, p. 109-112.*
Campbell, Monoclonal Antibody Technology, 1984, p. 1-31.*
Manfiolette et al, "The Protein Encoded by a Growth Arrest-Specific Gene (gas6) is a New Member of the Vitamin K-Dependent Proteins related to Protein S, A Negative Coregulator in the Blood Coagulation Cascade," Molecular and Cellular Biology, 1993, pp. 4976-4985, vol. 13.
Nakano et al, "Requirement of y-carbonxyglutamic acid residues for the biological activity of Gas6: contribution of endogenous Gas6 to the proliferation of vascular smooth muscle cells," J. Biochem, 1997, pp. 387-392, vol. 323, Great Britain.
Nagata et al, "Identification of the Product of Growth Arrest-specific Gene 6 as a Common Ligand for Axl Sky, and Mer Receptor Tyrosine Kinases," Journal of Biological Chemistry, 1996, pp. 30022-30027, vol. 271, No. 47, USA.
Mark et al, "Characterization of Gas6, a Member of the Superfamily of G. Domain-containing Proteins, as a Ligand for Rse and Ax1," Journal of Biological Chemistry, 1996, pp. 9785-9789, vol. 271, No. 16, USA.

* cited by examiner

*Primary Examiner*—Michael Szperka
*Assistant Examiner*—Yunsoo Kim
(74) *Attorney, Agent, or Firm*—Kenneth J. Dow

(57) ABSTRACT

The present invention provides novel proteins and peptides from the receptor binding region of human Growth Arrest Specific Gene 6 (Gas6) and antibodies, including specified portions or variants, specific for at least one such Gas6 peptide or fragment thereof. The aforesaid peptides can be used to generate human, primate, rodent, mammalian, chimeric, humanized and/or CDR-grafted anti-Gas6 antibodies. The invention also provides for the nucleic acids encoding such peptides and anti-Gas6 antibodies, complementary nucleic acids, vectors, host cells, and methods of making and using thereof, including therapeutic formulations, administration and devices. Fifteen novel peptide sequences from the Gas6 G domain that are implicated in Gas6 interactions with its receptors are identified, isolated, and synthesized so as to allow generation of anti-Gas6 antibodies. The peptide sequences include three ESTs that encompass regions predicted to contribute to receptor binding or that can raise anti-Gas6 antibodies. This invention provides for such antibodies to be used in modulating or treating at least one Gas6-related disease in a cell, tissue, organ, animal, or patient. Such diseases may include, but are not limited to, thromboembolic disease, ischemic disease, venous thromboembolism, arterial or venous thrombosis, pulmonary embolism, restenosis, diabetic angiopathy and allograft atherosclerosis.

5 Claims, 6 Drawing Sheets

A. pRSET/His-EST Expression

B. ProBond Affinity Purificat

SEQUENCE LISTING

<160> NUMBER OF SEQ ID NOS: 38

<210> SEQ ID NO 1
<211> LENGTH: 678
<212> TYPE: PRT
<213> ORGANISM: Homo sapiens

<400> SEQUENCE: 1

Met Ala Pro Ser Leu Ser Pro Gly Pro Ala Ala Leu Arg Arg Ala Pro
1               5                   10                  15

Gln Leu Leu Leu Leu Leu Leu Ala Ala Glu Cys Ala Leu Ala Ala Leu
                20                  25                  30

Leu Pro Ala Arg Glu Ala Thr Gln Phe Leu Arg Pro Arg Gln Arg Arg
            35                  40                  45

Ala Phe Gln Val Phe Glu Glu Ala Lys Gln Gly His Leu Glu Arg Glu
        50                  55                  60

Cys Val Glu Glu Leu Cys Ser Arg Glu Glu Ala Arg Glu Val Phe Glu
65                  70                  75                  80

Asn Asp Pro Glu Thr Asp Tyr Phe Tyr Pro Arg Tyr Leu Asp Cys Ile
                85                  90                  95

Asn Lys Tyr Gly Ser Pro Tyr Thr Lys Asn Ser Gly Phe Ala Thr Cys
                100                 105                 110

Val Gln Asn Leu Pro Asp Gln Cys Thr Pro Asn Pro Cys Asp Arg Lys
            115                 120                 125

Gly Thr Gln Ala Cys Gln Asp Leu Met Gly Asn Phe Phe Cys Leu Cys
        130                 135                 140

```
Lys Ala Gly Trp Gly Gly Arg Leu Cys Asp Lys Asp Val Asn Glu Cys
145                 150                 155                 160

Ser Gln Glu Asn Gly Gly Cys Leu Gln Ile Cys His Asn Lys Pro Gly
                165                 170                 175

Ser Phe His Cys Ser Cys His Ser Gly Phe Glu Leu Ser Ser Asp Gly
            180                 185                 190

Arg Thr Cys Gln Asp Ile Asp Glu Cys Ala Asp Ser Glu Ala Cys Gly
        195                 200                 205

Glu Ala Arg Cys Lys Asn Leu Pro Gly Ser Tyr Ser Cys Leu Cys Asp
    210                 215                 220

Glu Gly Phe Ala Tyr Ser Ser Gln Glu Lys Ala Cys Arg Asp Val Asp
225                 230                 235                 240

Glu Cys Leu Gln Gly Arg Cys Glu Gln Val Cys Val Asn Ser Pro Gly
                245                 250                 255

Ser Tyr Thr Cys His Cys Asp Gly Arg Gly Gly Leu Lys Leu Ser Gln
            260                 265                 270

Asp Met Asp Thr Cys Glu Asp Ile Leu Pro Cys Val Pro Phe Ser Val
        275                 280                 285

Ala Lys Ser Val Lys Ser Leu Tyr Leu Gly Arg Met Phe Ser Gly Thr
    290                 295                 300

Pro Val Ile Arg Leu Arg Phe Lys Arg Leu Gln Pro Thr Arg Leu Val
305                 310                 315                 320

Ala Glu Phe Asp Phe Arg Thr Phe Asp Pro Glu Gly Ile Leu Leu Phe
                325                 330                 335

Ala Gly Gly His Gln Asp Ser Thr Trp Ile Val Leu Ala Leu Arg Ala
            340                 345                 350

Gly Arg Leu Glu Leu Gln Leu Arg Tyr Asn Gly Val Gly Arg Val Thr
        355                 360                 365

Ser Ser Gly Pro Val Ile Asn His Gly Met Trp Gln Thr Ile Ser Val
370                 375                 380

Glu Glu Leu Ala Arg Asn Leu Val Ile Lys Val Asn Arg Asp Ala Val
385                 390                 395                 400

Met Lys Ile Ala Val Ala Gly Asp Leu Phe Gln Pro Glu Arg Gly Leu
                405                 410                 415

Tyr His Leu Asn Leu Thr Val Gly Gly Ile Pro Phe His Glu Lys Asp
            420                 425                 430

Leu Val Gln Pro Ile Asn Pro Arg Leu Asp Gly Cys Met Arg Ser Trp
        435                 440                 445

Asn Trp Leu Asn Gly Glu Asp Thr Thr Ile Gln Glu Thr Val Lys Val
    450                 455                 460

Asn Thr Arg Met Gln Cys Phe Ser Val Thr Glu Arg Gly Ser Phe Tyr
465                 470                 475                 480

Pro Gly Ser Gly Phe Ala Phe Tyr Ser Leu Asp Tyr Met Arg Thr Pro
                485                 490                 495

Leu Asp Val Gly Thr Glu Ser Thr Trp Glu Val Glu Val Val Ala His
            500                 505                 510

Ile Arg Pro Ala Ala Asp Thr Gly Val Leu Phe Ala Leu Trp Ala Pro
        515                 520                 525

Asp Leu Arg Ala Val Pro Leu Ser Val Ala Leu Val Asp Tyr His Ser
    530                 535                 540

Thr Lys Lys Leu Lys Lys Gln Leu Val Val Leu Ala Val Glu His Thr
545                 550                 555                 560
```

```
Ala Leu Ala Leu Met Glu Ile Lys Val Cys Asp Gly Gln Glu His Val
            565                 570                 575

Val Thr Val Ser Leu Arg Asp Gly Glu Ala Thr Leu Glu Val Asp Gly
        580                 585                 590

Thr Arg Gly Gln Ser Glu Val Ser Ala Ala Gln Leu Gln Glu Arg Leu
            595                 600                 605

Ala Val Leu Glu Arg His Leu Arg Ser Pro Val Leu Thr Phe Ala Gly
        610                 615                 620

Gly Leu Pro Asp Val Pro Val Thr Ser Ala Pro Val Thr Ala Phe Tyr
625                 630                 635                 640

Arg Gly Cys Met Thr Leu Glu Val Asn Arg Arg Leu Leu Asp Leu Asp
                645                 650                 655

Glu Ala Ala Tyr Lys His Ser Asp Ile Thr Ala His Ser Cys Pro Pro
            660                 665                 670

Val Glu Pro Ala Ala Ala
        675

<210> SEQ ID NO 2
<211> LENGTH: 15
<212> TYPE: PRT
<213> ORGANISM: homo

<400> SEQUENCE: 2

Val Pro Phe Ser Val Ala Lys Ser Val Lys Ser Leu Tyr Leu Gly
1               5                   10                  15

<210> SEQ ID NO 3
<211> LENGTH: 15
<212> TYPE: PRT
<213> ORGANISM: Homo sapiens

<400> SEQUENCE: 3

Leu Arg Phe Lys Arg Leu Gln Pro Thr Arg Leu Val Ala Glu Phe
1               5                   10                  15

<210> SEQ ID NO 4
<211> LENGTH: 18
<212> TYPE: PRT
<213> ORGANISM: homo sapiens

<400> SEQUENCE: 4

Ile Lys Val Asn Arg Asp Ala Val Met Lys Ile Ala Val Ala Gly Asp
1               5                   10                  15

Leu Phe

<210> SEQ ID NO 5
<211> LENGTH: 16
<212> TYPE: PRT
<213> ORGANISM: Homo sapiens

<400> SEQUENCE: 5

Val Met Lys Ile Ala Val Ala Gly Asp Leu Phe Gln Pro Glu Arg Gly
1               5                   10                  15

<210> SEQ ID NO 6
<211> LENGTH: 15
<212> TYPE: PRT
<213> ORGANISM: Homo sapiens

<400> SEQUENCE: 6

Ser Gly Phe Ala Phe Tyr Ser Leu Asp Tyr Met Arg Thr Pro Leu
```

```
                1               5                   10                  15

<210> SEQ ID NO 7
<211> LENGTH: 12
<212> TYPE: PRT
<213> ORGANISM: Homo sapiens

<400> SEQUENCE: 7

Tyr Met Arg Thr Pro Leu Asp Val Gly Thr Glu Ser
1               5                   10

<210> SEQ ID NO 8
<211> LENGTH: 15
<212> TYPE: PRT
<213> ORGANISM: Homo sapiens

<400> SEQUENCE: 8

Val Leu Phe Ala Leu Trp Ala Pro Asp Leu Arg Ala Val Pro Leu
1               5                   10                  15

<210> SEQ ID NO 9
<211> LENGTH: 13
<212> TYPE: PRT
<213> ORGANISM: Homo sapiens

<400> SEQUENCE: 9

Glu Ala Thr Leu Glu Val Asp Gly Thr Arg Gly Gln Ser
1               5                   10

<210> SEQ ID NO 10
<211> LENGTH: 18
<212> TYPE: PRT
<213> ORGANISM: Homo sapiens

<400> SEQUENCE: 10

Glu Val Ser Ala Ala Gln Leu Gln Glu Arg Leu Ala Val Leu Glu Arg
1               5                   10                  15

His Leu

<210> SEQ ID NO 11
<211> LENGTH: 16
<212> TYPE: PRT
<213> ORGANISM: Homo sapiens

<400> SEQUENCE: 11

His Leu Arg Ser Pro Val Leu Thr Phe Ala Gly Gly Leu Pro Asp Val
1               5                   10                  15

<210> SEQ ID NO 12
<211> LENGTH: 14
<212> TYPE: PRT
<213> ORGANISM: Homo sapiens

<400> SEQUENCE: 12

Val Pro Val Thr Ser Ala Pro Val Thr Ala Phe Tyr Arg Gly
1               5                   10

<210> SEQ ID NO 13
<211> LENGTH: 21
<212> TYPE: PRT
<213> ORGANISM: Homo sapiens

<400> SEQUENCE: 13

Leu Glu Val Asn Arg Arg Leu Leu Asp Leu Asp Glu Ala Ala Tyr Lys
```

His Ser Asp Ile Thr
            20

<210> SEQ ID NO 14
<211> LENGTH: 20
<212> TYPE: PRT
<213> ORGANISM: Homo sapiens

<400> SEQUENCE: 14

Phe Tyr Arg Gly Cys Met Thr Leu Glu Val Asn Arg Arg Leu Leu Asp
1               5                   10                  15

Leu Asp Glu Ala
            20

<210> SEQ ID NO 15
<211> LENGTH: 20
<212> TYPE: PRT
<213> ORGANISM: Homo sapiens

<400> SEQUENCE: 15

Ala Tyr Lys His Ser Asp Ile Thr Ala His Ser Cys Pro Pro Val Glu
1               5                   10                  15

Pro Ala Ala Ala
            20

<210> SEQ ID NO 16
<211> LENGTH: 227
<212> TYPE: PRT
<213> ORGANISM: Homo sapiens

<400> SEQUENCE: 16

Pro Arg Tyr Leu Asp Cys Ile Asn Lys Tyr Gly Ser Pro Tyr Thr Lys
1               5                   10                  15

Asn Ser Gly Phe Ala Thr Cys Val Gln Asn Leu Pro Asp Gln Cys Thr
            20                  25                  30

Pro Asn Pro Cys Asp Arg Lys Gly Thr Gln Ala Cys Gln Asp Leu Met
        35                  40                  45

Gly Asn Phe Phe Cys Leu Cys Lys Ala Gly Trp Gly Gly Arg Leu Cys
    50                  55                  60

Asp Lys Asp Val Asn Glu Cys Ser Gln Glu Asn Gly Gly Cys Leu Gln
65                  70                  75                  80

Ile Cys His Asn Lys Pro Gly Ser Phe His Cys Ser Cys His Ser Gly
                85                  90                  95

Phe Glu Leu Ser Ser Asp Gly Arg Thr Cys Gln Asp Ile Asp Glu Cys
            100                 105                 110

Ala Asp Ser Glu Ala Cys Gly Glu Ala Arg Cys Lys Asn Leu Pro Gly
        115                 120                 125

Ser Tyr Ser Cys Leu Cys Asp Glu Gly Phe Ala Tyr Ser Ser Gln Glu
    130                 135                 140

Lys Ala Cys Arg Asp Val Asp Glu Cys Leu Gln Gly Arg Cys Glu Gln
145                 150                 155                 160

Val Cys Val Asn Ser Pro Gly Ser Tyr Thr Cys His Cys Asp Gly Arg
                165                 170                 175

Gly Gly Leu Lys Leu Ser Gln Asp Met Asp Thr Cys Glu Asp Ile Leu
            180                 185                 190

Pro Cys Val Pro Phe Ser Val Ala Lys Ser Val Lys Ser Leu Tyr Leu
        195                 200                 205

```
Gly Arg Met Phe Ser Gly Thr Pro Val Ile Arg Leu Arg Phe Lys Arg
    210                 215                 220

Leu Gln Pro
225
```

<210> SEQ ID NO 17
<211> LENGTH: 135
<212> TYPE: PRT
<213> ORGANISM: Homo sapiens

<400> SEQUENCE: 17

```
Thr Arg Leu Val Ala Glu Phe Asp Phe Arg Thr Phe Asp Pro Glu Gly
1               5                   10                  15

Ile Leu Leu Phe Ala Gly Gly His Gln Asp Ser Thr Trp Ile Val Leu
            20                  25                  30

Ala Leu Arg Ala Gly Arg Leu Glu Leu Gln Leu Arg Tyr Asn Gly Val
        35                  40                  45

Gly Arg Val Thr Ser Ser Gly Pro Val Ile Asn His Gly Met Trp Gln
    50                  55                  60

Thr Ile Ser Val Glu Glu Leu Ala Arg Asn Leu Val Ile Lys Val Asn
65                  70                  75                  80

Arg Asp Ala Val Met Lys Ile Ala Val Ala Gly Asp Leu Phe Gln Pro
                85                  90                  95

Glu Arg Gly Leu Tyr His Leu Asn Leu Thr Val Gly Gly Ile Pro Phe
            100                 105                 110

His Glu Lys Asp Leu Val Gln Pro Ile Asn Pro Arg Leu Asp Gly Cys
        115                 120                 125

Met Arg Ser Trp Asn Trp Leu
    130                 135
```

<210> SEQ ID NO 18
<211> LENGTH: 144
<212> TYPE: PRT
<213> ORGANISM: Homo sapiens

<400> SEQUENCE: 18

```
Ser Thr Trp Glu Val Glu Val Ala His Ile Arg Pro Ala Ala Ala Asp
1               5                   10                  15

Thr Gly Val Leu Phe Ala Leu Trp Ala Pro Asp Leu Arg Ala Val Pro
            20                  25                  30

Leu Ser Val Ala Leu Val Asp Tyr His Ser Thr Lys Lys Leu Lys Lys
        35                  40                  45

Gln Leu Val Val Leu Ala Val Glu His Thr Ala Leu Ala Leu Met Glu
    50                  55                  60

Ile Lys Val Cys Asp Gly Gln Glu His Val Val Thr Val Ser Leu Arg
65                  70                  75                  80

Asp Gly Glu Ala Thr Leu Glu Val Asp Gly Thr Arg Gly Gln Ser Glu
                85                  90                  95

Val Ser Ala Ala Gln Leu Gln Glu Arg Leu Ala Val Leu Glu Arg His
            100                 105                 110

Leu Arg Ser Pro Val Leu Thr Phe Ala Gly Gly Leu Pro Asp Val Pro
        115                 120                 125

Val Thr Ser Ala Pro Val Thr Ala Phe Tyr Arg Gly Cys Met Thr Leu
    130                 135                 140
```

<210> SEQ ID NO 19

```
<211> LENGTH: 23
<212> TYPE: DNA
<213> ORGANISM: Homo sapiens

<400> SEQUENCE: 19
ccaagatact tagactgcat caa                                              23

<210> SEQ ID NO 20
<211> LENGTH: 20
<212> TYPE: DNA
<213> ORGANISM: Homo sapiens

<400> SEQUENCE: 20
cctcttgaag cgcagtcgga                                                  20

<210> SEQ ID NO 21
<211> LENGTH: 21
<212> TYPE: DNA
<213> ORGANISM: Homo sapiens

<400> SEQUENCE: 21
ccaggctggt agctgagttt g                                                21

<210> SEQ ID NO 22
<211> LENGTH: 21
<212> TYPE: DNA
<213> ORGANISM: Homo sapiens

<400> SEQUENCE: 22
tccgttcagc cagttccagc t                                                21

<210> SEQ ID NO 23
<211> LENGTH: 19
<212> TYPE: DNA
<213> ORGANISM: Homo sapiens

<400> SEQUENCE: 23
atccgcccag ccgcagaca                                                   19

<210> SEQ ID NO 24
<211> LENGTH: 20
<212> TYPE: DNA
<213> ORGANISM: Homo sapiens

<400> SEQUENCE: 24
cagtgtcatg cagccgcggt                                                  20

<210> SEQ ID NO 25
<211> LENGTH: 438
<212> TYPE: DNA
<213> ORGANISM: Homo sapiens
<220> FEATURE:
<221> NAME/KEY: CDS
<222> LOCATION: (1)..(438)
<220> FEATURE:
<221> NAME/KEY: misc_binding
<222> LOCATION: (148)..(162)
<220> FEATURE:
<221> NAME/KEY: misc_binding
<222> LOCATION: (205)..(255)
<220> FEATURE:
<221> NAME/KEY: misc_feature
<222> LOCATION: (305)..(305)
<223> OTHER INFORMATION: n is a, c, g, or t
<220> FEATURE:
<221> NAME/KEY: misc_binding
<222> LOCATION: (352)..(387)
```

```
<400> SEQUENCE: 25 atg gag ttt ggg ctg acc tgg gtt ttc ctc gtt gct ctt tta aga ggt        48
Met Glu Phe Gly Leu Thr Trp Val Phe Leu Val Ala Leu Leu Arg Gly
1               5                   10                  15 gtc cag tgt cag gtg cag ctg gtg gag tct ggg gga ggc gtg gtc cag        96
Val Gln Cys Gln Val Gln Leu Val Glu Ser Gly Gly Gly Val Val Gln
                20                  25                  30 cct ggg agg tcc ctg aga ctc tcc tgt gca gcg tct gga ttc acc ttc       144
Pro Gly Arg Ser Leu Arg Leu Ser Cys Ala Ala Ser Gly Phe Thr Phe
            35                  40                  45 agt agc tat ggc atg cac tgg gtc cgc cag gct cca ggc aag ggg ctg       192
Ser Ser Tyr Gly Met His Trp Val Arg Gln Ala Pro Gly Lys Gly Leu
        50                  55                  60 gag tgg gtg gca gtt ata tgg tat gat gga agt aat aaa tac tat gca       240
Glu Trp Val Ala Val Ile Trp Tyr Asp Gly Ser Asn Lys Tyr Tyr Ala
65                  70                  75                  80 gac tcc gtg aag ggg cga ttc acc atc tcc aga gac aat tcc aag aac       288
Asp Ser Val Lys Gly Arg Phe Thr Ile Ser Arg Asp Asn Ser Lys Asn
                85                  90                  95 acg ctg tat ctg caa ang aac agc ctg aga gcc gag gac acg gct atg       336
Thr Leu Tyr Leu Gln Xaa Asn Ser Leu Arg Ala Glu Asp Thr Ala Met
                100                 105                 110 tat ttc tgt gcg aga gaa ggg ttt tat tac gat att ttg act gct tat       384
Tyr Phe Cys Ala Arg Glu Gly Phe Tyr Tyr Asp Ile Leu Thr Ala Tyr
            115                 120                 125 tcc ctt gaa tac ttc cag cac tgg ggc cag ggc acc ctg gtc acc gtc       432
Ser Leu Glu Tyr Phe Gln His Trp Gly Gln Gly Thr Leu Val Thr Val
        130                 135                 140 tcc tca                                                                438
Ser Ser
145

<210> SEQ ID NO 26
<211> LENGTH: 146
<212> TYPE: PRT
<213> ORGANISM: Homo sapiens
<220> FEATURE:
<221> NAME/KEY: misc_feature
<222> LOCATION: (102)..(102)
<223> OTHER INFORMATION: The 'Xaa' at location 102 stands for Lys, Arg,
      Thr, or Met.

<400> SEQUENCE: 26

Met Glu Phe Gly Leu Thr Trp Val Phe Leu Val Ala Leu Leu Arg Gly
1               5                   10                  15

Val Gln Cys Gln Val Gln Leu Val Glu Ser Gly Gly Gly Val Val Gln
                20                  25                  30

Pro Gly Arg Ser Leu Arg Leu Ser Cys Ala Ala Ser Gly Phe Thr Phe
            35                  40                  45

Ser Ser Tyr Gly Met His Trp Val Arg Gln Ala Pro Gly Lys Gly Leu
        50                  55                  60

Glu Trp Val Ala Val Ile Trp Tyr Asp Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Xaa Asn Ser Leu Arg Ala Glu Asp Thr Ala Met
                100                 105                 110

Tyr Phe Cys Ala Arg Glu Gly Phe Tyr Tyr Asp Ile Leu Thr Ala Tyr
            115                 120                 125
```

Ser Leu Glu Tyr Phe Gln His Trp Gly Gln Gly Thr Leu Val Thr Val
    130                 135                 140

Ser Ser
145

<210> SEQ ID NO 27
<211> LENGTH: 378
<212> TYPE: DNA
<213> ORGANISM: Homo sapiens
<220> FEATURE:
<221> NAME/KEY: CDS
<222> LOCATION: (1)..(378)
<220> FEATURE:
<221> NAME/KEY: misc_binding
<222> LOCATION: (127)..(159)
<220> FEATURE:
<221> NAME/KEY: misc_binding
<222> LOCATION: (205)..(225)
<220> FEATURE:
<221> NAME/KEY: misc_binding
<222> LOCATION: (322)..(342)

<400> SEQUENCE: 27

```
atg tcg cca tca caa ctc att ggg ttt ctg ctg ctc tgg gtt cca gcc     48
Met Ser Pro Ser Gln Leu Ile Gly Phe Leu Leu Leu Trp Val Pro Ala
1               5                   10                  15 tcc agg ggt gaa att gtg ctg act cag tct cca gac ttt cag tct gtg    96
Ser Arg Gly Glu Ile Val Leu Thr Gln Ser Pro Asp Phe Gln Ser Val
            20                  25                  30 act cca aag gag aag gtc acc atc acc tgc cgg gcc agt cag agc att   144
Thr Pro Lys Glu Lys Val Thr Ile Thr Cys Arg Ala Ser Gln Ser Ile
        35                  40                  45 ggt agt agc tta cac tgg tac cag cag aaa cca gat cag tct cca aag   192
Gly Ser Ser Leu His Trp Tyr Gln Gln Lys Pro Asp Gln Ser Pro Lys
    50                  55                  60 ctc ctc atc aag tat gct tcc cag tcc ttc tca ggg gtc ccc tcg agg   240
Leu Leu Ile Lys Tyr Ala Ser Gln Ser Phe Ser Gly Val Pro Ser Arg
65                  70                  75                  80 ttc agt ggc agt gga tct ggg aca gat ttc acc ctc acc atc aat agc   288
Phe Ser Gly Ser Gly Ser Gly Thr Asp Phe Thr Leu Thr Ile Asn Ser
                85                  90                  95 ctg gaa gct gaa gat gct gca gcg tat tac tgt cat cag agt agt agt   336
Leu Glu Ala Glu Asp Ala Ala Ala Tyr Tyr Cys His Gln Ser Ser Ser
            100                 105                 110 tta ccg tac act ttt ggc cag ggg acc aag ctg gag atc aaa           378
Leu Pro Tyr Thr Phe Gly Gln Gly Thr Lys Leu Glu Ile Lys
        115                 120                 125
```

<210> SEQ ID NO 28
<211> LENGTH: 126
<212> TYPE: PRT
<213> ORGANISM: Homo sapiens

<400> SEQUENCE: 28

Met Ser Pro Ser Gln Leu Ile Gly Phe Leu Leu Leu Trp Val Pro Ala
1               5                   10                  15

Ser Arg Gly Glu Ile Val Leu Thr Gln Ser Pro Asp Phe Gln Ser Val
            20                  25                  30

Thr Pro Lys Glu Lys Val Thr Ile Thr Cys Arg Ala Ser Gln Ser Ile
        35                  40                  45

Gly Ser Ser Leu His Trp Tyr Gln Gln Lys Pro Asp Gln Ser Pro Lys
    50                  55                  60

```
Leu Leu Ile Lys Tyr Ala Ser Gln Ser Phe Ser Gly Val Pro Ser Arg
 65                  70                  75                  80

Phe Ser Gly Ser Gly Ser Gly Thr Asp Phe Thr Leu Thr Ile Asn Ser
                 85                  90                  95

Leu Glu Ala Glu Asp Ala Ala Tyr Tyr Cys His Gln Ser Ser Ser
            100                 105                 110

Leu Pro Tyr Thr Phe Gly Gln Gly Thr Lys Leu Glu Ile Lys
        115                 120                 125
```

<210> SEQ ID NO 29
<211> LENGTH: 6
<212> TYPE: PRT
<213> ORGANISM: Homo sapiens

<400> SEQUENCE: 29

```
Ser Tyr Gly Met His Trp
1               5
```

<210> SEQ ID NO 30
<211> LENGTH: 12
<212> TYPE: PRT
<213> ORGANISM: Homo sapiens

<400> SEQUENCE: 30

```
Val Ile Trp Tyr Asp Gly Ser Asn Lys Tyr Tyr Ala
1               5                   10
```

<210> SEQ ID NO 31
<211> LENGTH: 10
<212> TYPE: PRT
<213> ORGANISM: LC CDR1

<400> SEQUENCE: 31

```
Arg Ala Gln Ser Ile Gly Ser Ser Leu His
1               5                   10
```

<210> SEQ ID NO 32
<211> LENGTH: 11
<212> TYPE: PRT
<213> ORGANISM: Homo sapiens

<400> SEQUENCE: 32

```
Arg Ala Ser Gln Ser Ile Gly Ser Ser Leu His
1               5                   10
```

<210> SEQ ID NO 33
<211> LENGTH: 7
<212> TYPE: PRT
<213> ORGANISM: Homo sapiens

<400> SEQUENCE: 33

```
Tyr Ala Ser Gln Ser Phe Ser
1               5
```

<210> SEQ ID NO 34
<211> LENGTH: 7
<212> TYPE: PRT
<213> ORGANISM: Homo sapiens

<400> SEQUENCE: 34

```
His Gln Ser Ser Ser Leu Pro
1               5
```

-continued

```
<210> SEQ ID NO 35
<211> LENGTH: 21
<212> TYPE: DNA
<213> ORGANISM: Homo sapiens

<400> SEQUENCE: 35
agtctacgcc tgcgaagtca c                                              21

<210> SEQ ID NO 36
<211> LENGTH: 27
<212> TYPE: DNA
<213> ORGANISM: Homo sapiens

<400> SEQUENCE: 36
tggtggtgga cgtgagccac gaagacc                                        27

<210> SEQ ID NO 37
<211> LENGTH: 12
<212> TYPE: PRT
<213> ORGANISM: Homo sapiens

<400> SEQUENCE: 37

Ile Ala Val Ala Gly Asp Leu Phe Gln Pro Glu Arg
1               5                   10

<210> SEQ ID NO 38
<211> LENGTH: 15
<212> TYPE: PRT
<213> ORGANISM: Homo sapiens

<400> SEQUENCE: 38

Ala Val Pro Leu Ser Val Ala Leu Val Asp Tyr His Ser Thr Lys
1               5                   10                  15
```

GROWTH ARREST SPECIFIC GENE 6 PEPTIDES, ANTIBODIES, COMPOSITIONS, METHODS AND USES

CROSS REFERENCE TO RELATED APPLICATION

This application is a divisional of U.S. application Ser. No. 10/671,019 filed Sep. 24, 2003 now abandoned, which claims priority of U.S. provisional application Ser. No. 60/413,250, filed Sep. 24, 2002, now abandoned.

BACKGROUND OF THE INVENTION

A. Field of the Invention

The present invention relates to novel proteins and peptides from the putative receptor binding region of human Growth Arrest Specific Gene 6 (Gas6) and to antibodies, including specified portions or variants, specific for at least one such Gas6 peptide or fragment thereof, as well as nucleic acids encoding such anti-Gas6 antibodies, complementary nucleic acids, vectors, host cells, and methods of making and using thereof, including therapeutic formulations, administration and devices.

B. Related Art

Gas6 was first identified among a set of genes that are highly expressed during serum starvation of NIH 3T3 cells [1]. It was later classified as a new member of a vitamin K-dependent protein family closely related to the coagulation factor Protein S [2] [U.S. Pat. No. 5,538,861]. Gas6 and Protein S share common structure features with ~40% sequence homology. Both proteins contain a γ-carboxyglutamic acid-rich domain (Gla domain) at the N-terminus followed by four Epidermal Growth Factor-like (EGF) repeats and a tandem globular domain (G domain). However, Gas6 lacks the thrombin recognition sites that are important for the coagulation activity of Protein S. The G domain of Gas6 belongs to a superfamily of proteins including basement membrane proteins laminin and agrin and human steroid hormone-binding globulin (or androgen-binding protein) [3].

Gas6 is a putative ligand for the Axl family of receptor tyrosine kinases including Axl (Ark, Ufo, Tro7) [4, 5, and U.S. Pat. No. 5,538,861], Mer (Eyk, Nyk) [6] and Sky (Rse, Tyro3, DtK, Brt, Tif) [7, 8]. Gas6 binds to the receptors with nanomolar affinity and causes receptor auto-phosphorylation. The ability of Gas6 to bind to and activate the receptors requires vitamin K-dependent γ-carboxylation [9, 10]. However, truncated Gas6 or a splice variant of Gas6 containing the G domain is sufficient to activate the Rse receptor [11, 12] [U.S. Pat. No. 6,211,142]. It seems that the G domain is masked without γ-carboxylation. This "mask" can be removed by a properly modified Gla domain or removal of sequence upstream of the G domain. Gas6 is often found to be associated with the cell membrane due to Gla-mediated calcium-dependent binding to membrane phospholipids [13]. In most systems, secreted Gas6 or soluble recombinant Gas6 has full biological activity, although it is unknown if Gas6 is anchored to the membrane during receptor activation. One exception is that 3T3 cells transfected with Gas6, but not soluble Gas6, support growth of hematopoietic progenitor cells [14]. The hematopoietic effect of the transfected cells is not dependent on vitamin K and the nature of membrane association of Gas6 and the mechanism of action is unexplained.

Gas6 is expressed in the lung, intestine and terminally differentiated cells of most organs including capillary endothelial cells, vascular smooth muscle cells (VSMC) and neurons [2, 15]. It is also found in the alpha granules of platelets that are secreted or transported to the cell surface upon activation [16, 17]. Gas6 is not detected in plasma, macrophages, basophils, neutrophils, or lymphocytes. Under pathological conditions, Gas6 is up regulated at sites of inflammation, vessel injury, and in VSMCs of atherosclerotic plaques [18-20]. Axl is expressed by vascular endothelial cells, CD34+ progenitor cells, bone marrow stromal cells, monocytes and macrophages, but not in granulocytes or lymphocytes [5, 21-23]. Neuronal cells and many peripheral cells also express Axl. Mer is expressed in lung, kidney, ovary, prostate, mononuclear cells, monocytes, and macrophages, but not in granulocytes or peripheral blood B or T cells [24, 25]. While Sky is mainly expressed in adult brain, it is also found in gonadal tissues, kidney, and in regions of lymphoid tissues that exclude B or T cells [26, 27]. All three receptors are found in human platelets [17].

Over the past decade, Gas6 has been implicated in many cellular functions such as cell growth, apoptosis, cell adhesion and migration, phagocytosis, and possibly hematopoiesis. Gas6 is a potent mitogen for human Schwann cells [28]. It has been disclosed that Gas6 can be used to support cultured Schwann cells for the treatment of neuronal injury [U.S. Pat. No. 5,721,139]. Purified Gas6 also induces proliferation of serum-depleted NIH 3T3 cells [29] and density-inhibited C57 mammary cells [30]. Mesangial cell proliferation, a hallmark of glomerular sclerosis, can be stimulated by Gas6 [31]. In a model of glomerulonephritis induced by Thy 1.1 antibody, Gas6 and Axl levels are dramatically increased in mesangial cells. Injection of wafarin, an inhibitor of γ-carboxylation, or an extracellular portion of Axl suppresses mesangial cell proliferation in this disease model, suggesting that Gas6 plays a role in glomerular disease. Proliferation of VSMC and mesangial cells is also a feature of chronic rejection after kidney transplant. Moreover, Gas6 and Sky are highly expressed in normal kidney and the level of Gas6 is significantly higher in kidney tissues of allografts and isografts [32]. Thus, it is possible that Gas6 contributes to the pathogenesis of chronic rejection. In addition, Gas6 can stimulate GnRH neuronal cell migration [33], suggesting a role of Gas6 in the central nervous system.

Under certain conditions, Gas6 prevents cell death. Gas6 rescues human umbilical vein endothelial cells from apoptosis induced by serum-deprivation or tumor necrosis factor α [18]. Gas6 is also a survival factor for several other types of cells under serum deprivation, including NIH 3T3 fibroblast cells [29, 34, 35], cancer cells [36, 37], Gonadoptropin-releasing hormone (GnRH) neuronal cells [38] and hippocampal neuronal cells [39]. In contrast, endothelial cells from Gas6 knockout mice are protected from cell death induced by cytokines and anti-Fas antibodies [WO Patent No. 00/76309]. Also, the lack of Gas6 in mice suppresses angiogenesis induced by VEGF-matrigel. Since the ability of activated endothelial cells to secrete cytokines and growth factors has been greatly compromised in Gas6 knockout mice, Gas6 may contribute to endothelial cell apoptosis and angiogenic by regulating local levels of cytokines and growth factors.

The Axl family of receptors is present in many different types of tumor cells and is implicated in neoplasia. Axl, cloned from patients with chronic myelogenous leukemia (CMA), was the first of the family to be identified [Liu, 1988 #205] [40]. Elevated levels of Axl are associated with metastatic colon cancer and lunch cancer [41, 42]. Although none of the receptors or Gas6 are expressed in B and T cells [27], both Axl and Sky are expressed in myeloid leukemic blasts, while Mer is found in neoplastic T- and B-cell lines [21, 24, 43]. Mammary tumors but not non-tumorigenic progenitors express elevated levels of Sky [44]. Axl, Mer, and Sky are all capable of inducing transformation of fibroblasts [40, 45, 46]. Although a high level of Gas6 is found in multiple myeloma [47], the potential neoplastic effects of the receptors may be mediated by other ligand(s) as well. The most convincing evidence for other ligands for these receptors comes from studies of receptor and Gas6 knockout mice. The phenotype in the receptor triple knockout mice is more severe than that in Gas6 knockouts. Mice lacking all three receptors have multiple organ failure, adult blindness, lack of sperm in males and develop severe autoimmunity [27, 48]. Gas6 knockout mice do not show any obvious phenotype unless challenged under pathological conditions such as thrombosis and endothelial activation [17] [WO Patent No. 00/76309]. Given the similarity of Gas6 to Protein S, it is possible that protein S may have a role in activation of Axl, Mer, and Sky under certain physiological conditions. Protein S appears to bind to Sky in vitro. However, bovine and human Protein S bind well to murine Sky but not to their homologous receptor [4, 7].

Through interaction with Mer, Gas6 seems to play a role in outer segment phagocytosis by retinal pigment epithelial cells. Vertebrate photoreceptors undergo daily phagocytosis of photoreceptor outer segments by the adjacent retinal pigment epithelium (RPE). The Royal College of Surgeons (RCS) rat, with inherited homozygous deletion of Mer, suffers from retinal degeneration due to an inability of RPE cells to clear the outer segment [49]. Phagocytosis of outer segment by cultured rat RPE cells can be stimulated by Gas6 [50]. Mer is also reported to play a role in phagocytosis of apoptotic cells by macrophages, an important process to prevent inflammation and autoimmunity against intracellular antigens [51]. Mutant mice expressing kinase-deleted Mer have increased autoantibodies, and macrophages from the mutant fail to clear apoptotic thymocytes. The phenotype of autoimmune response is more severe in the receptor triple knockout [27]. It is unclear whether Gas6 mediates any of these latter responses through Mer since Gas6 knockout mice are not reported to develop autoimmunity.

Gas6 is expressed in hematopoetic tissues and seems to regulate erythropoiesis under pathological condition [52, 53]. Gas6 knockout mice have a reduced erythrocyte count and fewer cells of erythroid lineage in bone marrow, spleen, and fetal liver. The hematocrit in the blood is, however, normal in the mutant mice. Gas6 deficient mice are more susceptible to acute hemolytic anemia induced by phenylhydrazine or autoimmune hemolytic anemia induced by NZB-derived 4C8 IgG2a anti-red cell antibody. Even though bone marrow erythroid precursors do not express Gas6, the erythropoietic effect of Gas6 may be mediated through Sky as it is found in erythroid precursors.

Vascular neointima formation, a process involving VSMC proliferation and migration, contributes to the formation and progression of lesions of restenosis and atherosclerosis. Treatment of VSMC with Gas6 causes enhancement of the growth response to thrombin and angiotensin II [54], induction of cell migration [55] and prevention of serum-deprivation-induced cell death [56]. Upon balloon injury, the level of Gas6 and Axl rises dramatically in the rat carotid artery [19]. This up-regulation of Gas6 and Axl parallels the time course of migration of the VSMC from media to intima, suggesting a role of Gas6 in the pathogenesis of restenosis and atherosclerosis. In fact, arterial stenosis induced by carotid artery ligation is reduced in Gas6 deficient mice [WO Patent No. 00/76309].

One of the common features of all cardiovascular disorders is activation of endothelium, which induces inflammatory responses causing severe damage in affected tissues. Gas6 may be involved directly or indirectly in the inflammatory response. A role of Gas6 in leukocyte adhesion during inflammatory response is controversial. In murine myeloid progentitor 32D cells, Gas6 promotes Axl-mediated cell adhesion [57]. A high concentration of Gas6, on the other hand, inhibits granulocyte adhesion to endothelial cells [58]. Interestingly, endothelial cells lacking Gas6 fail to induce expression of cytokines, adhesion molecules and tissue factor upon TNFα or endotoxin stimulation [WO Patent No. 00/76309], indicating a pro-inflammatory role of Gas6. Leukocyte adhesion to the arterial wall upon endotoxin challenge is markedly reduced in Gas6 deficient mice. In an ischemic stroke model, the infarction size in the Gas6 knockout mice is significantly reduced, possibly as a result of suppression of the inflammatory response [WO Patent No. 00/76309].

Studies from Gas6 deficient mice have revealed a surprising function of Gas6 in thrombosis [17]. Platelet aggregation and secretion stimulated by other aganonists are impaired in Gas6 knockout mice. Platelet aggregates induced by thrombin from the mutant are loosely packed, suggesting the possibility that lack of Gas6 might prevent formation of stable platelet plaque in vivo. Indeed, Gas6 contributes to thrombus generation in vivo. Gas6 mutant mice or wild type mice treated with neutralizing polyclonal antibodies are protected from lethal challenge of pulmonary thrombosis, a platelet dependent thrombosis model. Gas6 may also contribute to fibrin dependent thrombus formation due to its effect on tissue factor expression in endothelial cells. This is supported by the result from other thrombosis models in which the role of platelet is less prominent [17]. The thrombus size in Gas6 mutant mice is 60-85% smaller than wild type after carotid artery injury- or ligation of inferior vena cava.

There is a controversial role of Gas6 in diabetes, particularly in the development of noninsulin-dependent diabetes mellitus (NIDDM) and insulin-resistant disorders. Transgenic mice ectopically expressing Axl or the extracellular domain of Axl in myeloid cells develop phenotypes similar to NIDDM [59]. These animals display hyperglycemia, hyperinsulinemia, severe insulin resistance, progressive obesity, hepatic lipidsis and pancreatic islet dysplasia, but do not exhibit hyperphagia. These animals express an elevated level of TNFα in serum, which may cause insulin resistance in these mice. Addition of Gas6 to blood samples eliminates LPS-induced TNFα induction. Transgenic mice systemically expressing Gas6, on the other hand, do not show diabetic phenotype. In a different set of experiments, administration of Gas6 in combination with insulin causes higher insulin level than mice treated with insulin alone [WO Patent No. 99/49894]. Further study is required to support a role of Gas6 in diabetes under physiological condition.

Gas6 and Sky are expressed in osteoclasts and seem to be involved in osteoclastic bone resorption [60]. Treatment with Gas6 doubles the amount of pit area on a denite slice resorbed by osteoclast cells. Coincidentally, the level of Gas6 is up regulated in ovariectomized mice receiving estrogen. Ovariectomized mice is a model of postmenopausal osteoporosis caused by estrogen withdrawal. Osteoclast bone resorption is also observed in rheumatoid arthritis and ostoarthritis, which is accompanied by an elevated level of Gas6 [18]. Thus, it is possible that Gas6 contributes to bone loss in patients suffering from osteoporosis and arthritis.

Overall, Gas6 plays an important role in multiple pathophysiological processes, many of which lead to life threatening diseases. Development of Gas6 antibodies will be useful for a variety of diagnostic applications and a broad spectrum of therapeutic applications. In particular, neutralizing monoclonal antibodies or antagonists of human Gas6 can be applied to prevent or treat thromboembolic disease or thrombotic pathologic condition such as ischemic disease (ischemic stroke, ischemic cerebral infarction, acute myocardial infarction, and chronic ischemic heart disease), venous thromboembolism, arterial or venous thrombosis, pulmonary embolism, restenosis following coronary artery bypass surgery or following percutaneous transluminal angioplasty of a coronary artery, diabetic angiopathy and allograft arteriosclerosis. Gas6 antagonists may also be beneficial for preventing or treating other disease conditions such as cancer, atherosclerosis, sepsis, glomerular sclerosis, diabetes, rheumatoid arthritis, osteoarthritis and osteoporosis.

The only reported antibodies to Gas6 are polyclonal preparations, primarily generated by immunizing animals with purified native protein or recombinant full-length protein. Two polyclonal antibodies marketed by Santa Cruz Biotechnology, Inc. are from animals immunized with undisclosed peptide sequences derived from the N- and C-termini of the human Gas6 protein. These disclosed antibodies are not suitable as therapeutic agents and unproven for diagnostic applications.

Accordingly, there is a need for a novel method for generating anti-Gas6 antibodies (also termed Gas6 antibodies) based on structural information for the Gas6 protein.

SUMMARY OF THE INVENTION

The present invention provides novel peptide sequences identified as the putative receptor binding region of human Gas6. These peptides correspond to the putative receptor binding regions other than the N and C termini of human Gas6 protein. The peptides generated from the sequences are useful for generating and characterizing human, primate, rodent, mammalian, chimeric, single chain, humanized and/or CDR-grafted anti-Gas6 antibodies, immunoglobulins, cleavage products and other specified portions and variants thereof. This invention thus relates to such anti-Gas6 antibodies as well as to anti-Gas6 antibody compositions, the amino acid sequences of the antibodies, the nucleic acid sequences encoding the amino acid sequences, complementary nucleic acids, vectors, host cells, compositions, formulations, devices, transgenic animals, and transgenic plants, as described and enabled herein, in combination with what is known in the art.

The present invention provides at least one human Gas6 peptide sequence as described herein. In one aspect of the invention, the sequence information of human Gas6 was used to create a simulated structure model of Gas6 on the computer which was then used to design a series of peptides and/or polypeptides that are implicated in Gas6 interaction with its receptors. Another aspect of the invention provides the amino acid sequences of these novel peptides and/or polypeptides, which are antigenic and which offer a method for the generation of anti-Gas6 antibodies. This invention further provides that this new class of Gas6 antigens contains critical epitopes for diagnostic and therapeutic Gas6 antibodies.

The present invention provides, in one aspect, isolated amino acid sequences that correspond to the putative region in which human Gas6 binds its receptor. These sequences are useful in the generation and characterization of antibodies against Gas6. The present invention further provides for the synthesis of peptides based on the amino acid sequence.

The invention also relates to isolated polypeptides comprised of human Gas6 peptide sequences having at least 80% amino acid sequence identity to an amino acid sequence of SEQ ID NO. 2 to 15.

The invention also relates to isolated polypeptides comprised of human Gas6 peptide sequences having at least 80% amino acid sequence identity to an amino acid sequence of SEQ ID NO. 16, 17, and 18.

The present invention provides, in one aspect, isolated ESTs (expressed sequence tags) that code for protein domains that encompass regions predicted to contribute to receptor binding or that can be used to raise antibodies that inhibit Gas6 activity. The present invention further provides for the production of said EST proteins.

In one aspect, the present invention relates to anti-Gas6 antibodies. Thus, the present invention provides an antibody capable of binding to a polypeptide having at least 80% amino acid sequence identity to an amino acid sequence of SEQ ID NO. 2 to 15.

In another aspect, the present invention provides an antibody capable of binding to a polypeptide having at least 80% amino acid sequence identity to an amino acid sequence of SEQ ID NO. 16, 17, and 18.

In another aspect, the present invention provides an antibody comprising a chimeric molecule comprising a polypeptide capable of binding to a polypeptide, which has at least 80% amino acid sequence identity to an amino acid sequence of SEQ ID NO. 2 to 15 or 16, 17, and 18, fused to a heterologous amino acid sequence.

An antibody of the invention can include or be derived from any mammal, such as but not limited to a human, a mouse, a rabbit, a rat, a rodent, a primate, or any combination thereof, and the like.

The present invention provides, in one aspect, isolated nucleic acid molecules comprising, complementary, or hybridizing to, a polynucleotide encoding specific Gas6 peptides and/or anti-Gas6 antibodies, comprising at least one specified sequence, domain, portion or variant thereof. The present invention further provides recombinant vectors comprising said Gas6 peptides and/or anti-Gas6 antibody nucleic acid molecules, host cells containing such nucleic acids and/or recombinant vectors, as well as methods of making and/or using such antibody nucleic acids, vectors and/or host cells.

At least one antibody of the invention binds at least one specified epitope specific to at least one Gas6 protein, subunit, fragment, portion of the invention or any combination thereof. The at least one epitope can comprise at least one antibody binding region that comprises at least one portion of said protein, which epitope is preferably comprised of at least 1-5 amino acids of at least one portion thereof, such as but not limited to, at least one functional, or structural domain of said protein, or any portion thereof.

The at least one antibody can optionally comprise at least one specified portion of at least one complementarity determining region (CDR) (e.g., CDR1, CDR2 or CDR3 of the heavy or light chain variable region) and optionally further comprising at least one constant or variable framework region or any portion thereof. The at least one antibody amino acid sequence can further optionally comprise at least one specified substitution, insertion or deletion as described herein or as known in the art.

The present invention also provides at least one isolated anti-Gas6 antibody as described herein, wherein the antibody has at least one activity, such as, but not limited to neutralizing Gas6-dependent receptor phosphorylation, receptor internalization, cell proliferation, prevention of cell apoptosis, and induction of signaling molecules or adaptation of cell markers. An anti-Gas6 antibody can thus be screened for a corresponding activity according to known methods, such as but not limited to, at least one biological activity of Gas6 towards an Axl, Mer, or Sky receptor.

The present invention further provides at least one Gas6 anti-idiotype antibody to at least one Gas6 antibody of the present invention. The anti-idiotype antibody includes any protein or peptide containing molecule that comprises at least a portion of an immunoglobulin molecule, such as but not limited to at least one ligand binding portion (LBP), such as but not limited to a complementarity determining region (CDR) of a heavy or light chain, or a ligand binding portion thereof, a heavy chain or light chain variable region, a heavy chain or light chain constant region, a framework region, or any portion thereof, that can be incorporated into an antibody of the present invention. An antibody of the invention can include or be derived from any mammal, such as but not limited to a human, a mouse, a rabbit, a rat, a rodent, a primate, and the like.

The present invention provides, in one aspect, isolated nucleic acid molecules comprising, complementary, or hybridizing to, a polynucleotide encoding at least one Gas6 anti-idiotype antibody, comprising at least one specified sequence, domain, portion or variant thereof. The present invention further provides recombinant vectors comprising said Gas6 anti-idiotype antibody encoding nucleic acid molecules, host cells containing such nucleic acids and/or recombinant vectors, as well as methods of making and/or using such anti-idiotype antibody nucleic acids, vectors and/or host cells.

The present invention also provides at least one method for expressing at least one anti-Gas6 antibody, or Gas6 anti-idiotype antibody, in a host cell, comprising culturing a host cell as described herein under conditions wherein at least one anti-Gas6 antibody is expressed in detectable and/or recoverable amounts.

The present invention also provides at least one composition comprising (a) an isolated anti-Gas6 antibody encoding nucleic acid and/or antibody as described herein; and (b) a suitable carrier or diluent. The carrier or diluent can optionally be pharmaceutically acceptable, according to known carriers or diluents. The composition can optionally further comprise at least one further compound, protein or composition.

The present invention further provides at least one anti-Gas6 antibody method or composition, for administering a therapeutically effective amount to modulate or treat at least one Gas6 related condition in a cell, tissue, organ, animal or patient and/or, prior to, subsequent to, or during a related condition, as known in the art and/or as described herein.

The present invention also provides at least one composition, device and/or method of delivery of a therapeutically or prophylactically effective amount of at least one anti-Gas6 antibody, according to the present invention.

The present invention further provides at least one anti-Gas6 antibody method or composition, for diagnosing at least one Gas6 related condition in a cell, tissue, organ, animal or patient and/or, prior to, subsequent to, or during a related condition, as known in the art and/or as described herein.

The present invention also provides at least one composition, device and/or method of delivery for diagnosing of at least one anti-Gas6 antibody, according to the present invention.

Also provided is a composition comprising at least one isolated mammalian anti-Gas6 antibody as described herein and at least one pharmaceutically acceptable carrier or diluent. The composition can optionally further comprise an effective amount of at least one compound or protein selected from at least one of a detectable label or reporter, a TNF antagonist, an antirheumatic, a muscle relaxant, a narcotic, a non-steroid anti-inflammatory drug (NTHE), an analgesic, an anesthetic, a sedative, a local anesthetic, a neuromuscular blocker, an antimicrobial, an antipsoriatic, a corticosteriod, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog, a cytokine, or a cytokine antagonist.

The present invention further provides an anti-idiotype antibody or fragment that specifically binds at least one isolated mammalian anti-Gas6 antibody of the present invention.

Also provided is a method for diagnosing or treating a Gas6-related condition in a cell, tissue, organ or animal, comprising (a) contacting or administering a composition comprising an effective amount of at least one isolated mammalian anti-Gas6 antibody of the invention with, or to, the cell, tissue, organ or animal. The method can optionally further comprise using an effective amount of 0.001-50 mg/kilogram of the antibody. The method can optionally further comprise treating the Gas6-related condition with the antibody by administering the antibody by at least one mode selected from parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal.

Also provided is a medical device, comprising at least one isolated mammalian anti-Gas6 antibody of the invention, wherein the device is suitable for contacting or administering the at least one anti-Gas6 antibody by at least one mode selected from parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal.

Also provided is an article of manufacture for human pharmaceutical or diagnostic use, comprising packaging material and a container comprising a solution or a lyophilized form of at least one isolated mammalian anti-Gas6 antibody of the present invention. The article of manufacture can optionally comprise having the container as a component of a parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal delivery device or system.

The present invention further provides an antibody for the use in preventing and/or treating a large spectrum of disorders, including, but not limited to: stroke, heart attack, atherosclerosis, restenosis, sepsis, cancers, glomerular sclerosis, osteoporosis, rheumatoid arthritis, osteoarthritis, diabetes, and other thrombotic or inflammatory complications.

Also provided is a method for producing at least one isolated mammalian anti-Gas6 antibody of the present invention, comprising providing a host cell or transgenic animal or transgenic plant or plant cell capable of expressing in recoverable amounts the antibody. Further provided in the present invention is at least one anti-Gas6 antibody produced by the above method.

The present invention further provides any invention described herein.

DESCRIPTION OF THE FIGURES

FIG. 3A shows the O.D. results. FIG. 3B shows the % inhibition of Gas 6 binding.

DESCRIPTION OF THE INVENTION

Figure 1:
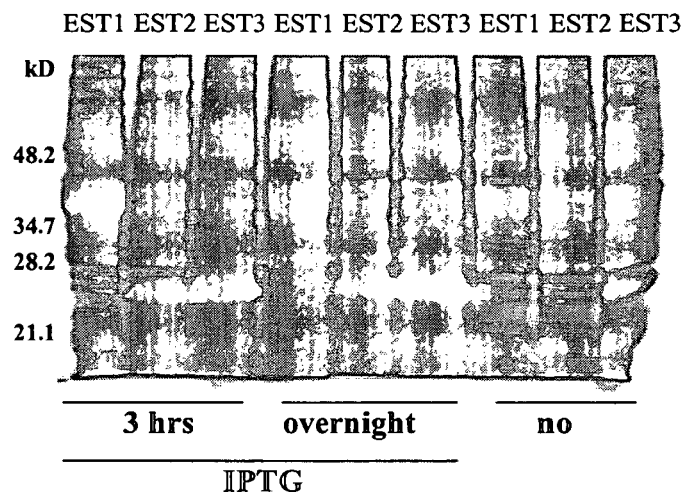
FIG. 1. is a photograph of a SDS-PAGE stained for protein on which expressed and purified Gas6 ESTs were separated. A. Bacteria cells transformed with pRSET vector expressing His-ESTs were treated with 1 mM IPTG as indicated and protein staining of total cell lysate on a SDS-PAGE is shown. B. Total cell lysate of bacteria cells treated with IPTG for 4 hours was purified by a ProBond resin. Eluted samples were desalted and analyzed by SDS-PAGE.
Figure 1:
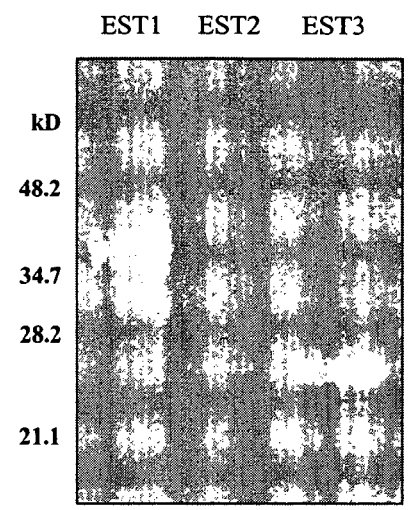

The present invention provides for novel proteins and peptides from Gas6's receptor binding region that can be used to generate anti-Gas6 antibodies and fragments thereof. In the first five parts of the invention, the methods of identifying, isolating, and creating the novel peptides are discussed. In the remaining six parts, the generation of antibodies, applications, formulations, and therapeutic treatments are presented.

All publications or patents cited herein are entirely incorporated herein by reference as they show the state of the art at the time of the present invention and/or to provide description and enablement of the present invention. Publications refer to any scientific or patent publications, or any other information available in any media format, including all recorded, electronic or printed formats. The following references are entirely incorporated herein by reference: Ausubel, et al., ed., Current Protocols in Molecular Biology, John Wiley & Sons, Inc., NY, N.Y. (1987-2001); Sambrook, et al., Molecular Cloning: A Laboratory Manual, 2nd Edition, Cold Spring Harbor, N.Y. (1989); Harlow and Lane, antibodies, a Laboratory Manual, Cold Spring Harbor, N.Y. (1989); Colligan, et al., eds., Current Protocols in Immunology, John Wiley & Sons, Inc., NY (1994-2001); Colligan et al., Current Protocols in Protein Science, John Wiley & Sons, NY, N.Y., (1997-2001).

A. Identifying and Synthesizing Novel Peptides from Receptor Binding Region of Gas6

Novel peptides that from the receptor binding region of human Gas6 were identified and synthesized. Using the crystal structure of laminin alpha 2 chain as a base, a homology model of the G domain of Gas6 can be constructed by the skilled artisan with the help of computer software. Once the simulated structure model is created, specific amino acid sequences from Gas6 can be identified depending on their location and lipophilicity.

Peptides, encoded by the amino acid sequences, may be synthesized using standard Boc or FMOC chemistry. The resulting peptides can be injected as is, cross-linked, or conjugated to a carrier molecule. To facilitate conjugation to carriers, an N-terminal N-acetyl-cysteine or C-terminal amides can be formed and the C-terminal amino acid can be amidated. A variety of linking groups may be interspaced between the peptide and the carrier molecule to allow for proper conformational folding and presentation of the antigenic peptide.

These novel peptide constructs can be used as immunogens or as binding partners to generate, select, or characterize anti-Gas6 antibodies, immunoglobulins, cleavage products and other specified portions and variants thereof.

B. Isolating and Producing Gas6 ESTs

From the simulated structure model, novel Gas6 derivatives (ESTs) which form polypeptides having three-dimensional structure and that are predicted to contribute to receptor binding are identified and isolated. Once the nucleic acid sequences are defined, the ESTs can be cloned by a variety of methods.

In one method, the nucleic acid sequences can be cloned using RT-PCR amplification of RNA samples from CHFR cell line and then the ESTs can be produced by bacteria. First, the DNA sequences must be PCR amplified using oligonucleotide primers and then cloned in-frame into the BAMHI-EcoRI sit of a pRSET vector. Second, the vector must be inserted into a host cell; e.g., bacteria where, under the control of an IPTG inducible promoter, the EST can be produced. In such an example, the N-terminus of the EST can be ligated in-frame with a poly-histidine tag so that purification is easier. Upon IPTG induction, the host cell can begin expressing the ESTs reaching a maximum expression in 3-4 hours. Finally, the cells can be harvested, lysed and the protein purified per the instruction manual for the given purification system. (comment: pRSET vector with IPTG induction only works in bacteria)

In an alternative method for isolating and producing ESTs, the nucleic acid encoding the Gas6 polypeptide can be obtained through DNA synthesis, from any cDNA library, or from a genomic DNA library. Once the DNA has been identified, it can be cloned using PCR amplification or by another other traditional method of DNA hybridization and expression cloning. The cloned DNA can be ligated in-frame to a vector that is used to transform a cell thereby allowing the cell to express the desired polypeptide.

B.1. Amino Acid Codes

The amino acid sequences that make up the Gas6 polypeptides and anti-Gas6 antibodies of the present invention are often abbreviated. The amino acid designations as used herein are indicated by designating the amino acid by its single letter code, its three letter code, name, or three nucleotide codon(s) as is well understood in the art (see Alberts, B., et al., Molecular Biology of The Cell, Third Ed., Garland Publishing, Inc., New York, 1994):

TABLE 1

Amino Acid Abbreviations, Codes, and Codons

| Single Letter Code | Three Letter Code | Name | Three Nucleotide Codon(s) |
|---|---|---|---|
| A | Ala | Alanine | GCA, GCC, GCG, GCU |
| C | Cys | Cysteine | UGC, UGU |
| D | Asp | Aspartic acid | GAC, GAU |
| E | Glu | Glutamic acid | GAA, GAG |
| F | Phe | Phenylanine | UUC, UUU |
| G | Gly | Glycine | GGA, GGC, GGG, GGU |
| H | His | Histidine | CAC, CAU |
| I | Ile | Isoleucine | AUA, AUC, AUU |
| K | Lys | Lysine | AAA, AAG |
| L | Leu | Leucine | UUA, UUG, CUA, CUC, CUG, CUU |
| M | Met | Methionine | AUG |
| N | Asn | Asparagine | AAC, AAU |
| P | Pro | Proline | CCA, CCC, CCG, CCU |
| Q | Gln | Glutamine | CAA, CAG |
| R | Arg | Arginine | AGA, AGG, CGA, CGC, CGG, CGU |
| S | Ser | Serine | AGC, AGU, UCA, UCC, UCG, UCU |
| T | Thr | Threonine | ACA, ACC, ACG, ACU |
| V | Val | Valine | GUA, GUC, GUG, GUU |
| W | Trp | Tryptophan | UGG |
| Y | Tyr | Tyrosine | UAC, UAU |

A human Gas6 protein, peptide, or EST sequence of the present invention can include one or more amino acid substitutions, deletions or additions, either from natural mutations or human manipulation, as specified herein. Such mutations or substitutions result in muteins, whose mutations can be significant enough to alter the properties of the peptide.

Of course, the number of amino acid substitutions a skilled artisan would make depends on many factors, including those described above. Generally speaking, the number of amino acid substitutions, insertions or deletions for any given Gas6 polypeptide, fragment or variant will not be more than 40, 30, 20, 19, 18, 17, 16, 15, 14, 13, 12, 11, 10, 9, 8, 7, 6, 5, 4, 3, 2, 1, such as 1-30 or any range or value therein, as specified herein.

Amino acids in a Gas6 peptide of the present invention that are essential for function can be identified by methods known in the art, such as site-directed mutagenesis or alanine-scanning mutagenesis (e.g., Ausubel, supra, Chapters 8, 15; Cunningham and Wells, Science 244:1081-1085 (1989)). The latter procedure introduces single alanine mutations at every residue in the molecule. The resulting mutant molecules are then tested for biological activity, such as, but not limited to at least one Gas6 neutralizing activity.

C. Synthesis of Peptides from Gas6 G Domains

Although these peptides were synthesized with N-terminal N-acetylated cysteines, it is envisioned that C-terminal amides would work equally well. Likewise, while these peptides were acetylated and amidated, it is envisioned that peptides with free N-terminal amino groups and/or free C-terminal carboxylic acids would work equally well. Other embodiments including the use of linkers between the cysteine and the peptide sequence of interest, substituted amides, acyl groups other than acetyl, and substitution of amino acids not surface exposed in the Gas6 G domain are also envisioned. Also envisioned are moieties other than cysteine which can be used to conjugate or immobilize the peptides.

D. Nucleic Acid Molecules

Nucleic acid sequence of human Gas6 (SEQ ID NO. 1) was cloned by RT-PCR amplification of RNA samples. Alternatively, the DNA encoding Gas6 EST polypeptide may be obtained by DNA synthesis or from any cDNA library prepared from tissues believed to possess the Gas6 mRNA or from a genomic DNA library. The nucleic acid sequences can be cloned by PCR amplification or by traditional method of DNA hybridization and expression cloning.

D.1. Nucleic Acids Encoding Novel Peptides

Using the information provided herein, such as the nucleotide sequences encoding at least 80-100% of the contiguous amino acids of at least one of SEQ ID NOS: 2, 3, 4, 5, 6, 7, 8, 9, 10, 11, 12, 13, 14, 15, 16, 17, or 18 specified fragments, variants or consensus sequences thereof, or a deposited vector comprising at least one of these sequences, a nucleic acid molecule of the present invention encoding at least one Gas6 polypeptide or anti-Gas6 antibody can be obtained using methods described herein or as known in the art.

Nucleic acid molecules of the present invention can be in the form of RNA, such as mRNA, hnRNA, or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

Isolated nucleic acid molecules of the present invention can include nucleic acid molecules comprising an open reading frame (ORF), optionally with one or more introns, e.g., but not limited to, at least one specified portion of at least one CDR, as CDR1, CDR2 and/or CDR3 of at least one heavy chain or light chain; nucleic acid molecules comprising the coding sequence for an anti-Gas6 antibody or variable region; and nucleic acid molecules which comprise a nucleotide sequence substantially different from those described above but which, due to the degeneracy of the genetic code, still encode at least one anti-Gas6 antibody as described herein and/or as known in the art. Of course, the genetic code is well known in the art. Thus, it would be routine for one skilled in the art to generate such degenerate nucleic acid variants that code for specific anti-Gas6 antibodies of the present invention. See, e.g., Ausubel, et al., supra, and such nucleic acid variants are included in the present invention.

As indicated herein, nucleic acid molecules of the present invention which comprise a nucleic acid encoding a Gas6 polypeptide or anti-Gas6 antibody can include, but are not limited to, those encoding the amino acid sequence of a polypeptide or antibody fragment, by itself; the coding sequence for the entire polypeptide or antibody or a portion thereof; the coding sequence for a polypeptide or antibody, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example—ribosome binding and stability of mRNA); an additional coding sequence that codes for additional amino acids, such as those that provide additional functionalities. Thus, the sequence encoding a polypeptide or antibody can be fused to a marker sequence, such as a sequence encoding a peptide that facilitates purification of the fused antibody comprising an antibody fragment or portion.

D.2. Polynucleotides Which Selectively Hybridize to a Polynucleotide as Described The present invention provides isolated nucleic acids that hybridize under selective hybridization conditions to a polynucleotide disclosed herein. Thus, the polynucleotides of this embodiment can be used for isolating, detecting, and/or quantifying nucleic acids comprising such polynucleotides. For example, polynucleotides of the present invention can be used to identify, isolate, or amplify partial or full-length clones in a deposited library. In some embodiments, the polynucleotides are genomic or cDNA sequences isolated, or otherwise complementary to, a cDNA from a human or mammalian nucleic acid library.

Preferably, the cDNA library comprises at least 80% full-length sequences, preferably at least 85% or 90% full-length sequences, and more preferably at least 95% full-length sequences. The cDNA libraries can be normalized to increase the representation of rare sequences. Low or moderate stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

Optionally, polynucleotides of this invention will encode at least a portion of an antibody encoded by the polynucleotides described herein. The polynucleotides of this invention embrace nucleic acid sequences that can be employed for selective hybridization to a polynucleotide encoding an antibody of the present invention. See, e.g., Ausubel, supra; Colligan, supra, each entirely incorporated herein by reference.

D.3. Construction of Nucleic Acids

The isolated nucleic acids of the present invention can be made using (a) recombinant methods, (b) synthetic techniques, (c) purification techniques, or combinations thereof, as well known in the art.

The nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the present invention. For example, a hexa-histidine marker sequence provides a convenient means to purify the proteins of the present invention. The nucleic acid of the present invention—excluding the coding sequence—is optionally a vector, adapter, or linker for cloning and/or expression of a polynucleotide of the present invention.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra)

D.4. Recombinant Methods for Constructing Nucleic Acids

The isolated nucleic acid compositions of this invention, such as RNA, cDNA, genomic DNA, or any combination thereof, can be obtained from biological sources using any number of cloning methodologies known to those of skill in the art. In some embodiments, oligonucleotide probes that selectively hybridize, under stringent conditions, to the polynucleotides of the present invention are used to identify the desired sequence in a cDNA or genomic DNA library. The isolation of RNA, and construction of cDNA and genomic libraries, is well known to those of ordinary skill in the art. (See, e.g., Ausubel, supra; or Sambrook, supra)

D.5. Nucleic Acid Screening and Isolation Methods

A cDNA or genomic library can be screened using a probe based upon the sequence of a polynucleotide of the present invention, such as those disclosed herein. Probes can be used to hybridize with genomic DNA or cDNA sequences to isolate homologous genes in the same or different organisms. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by one or more of temperature, ionic strength, pH and the presence of a partially denaturing solvent such as formamide. For example, the stringency of hybridization is conveniently varied by changing the polarity of the reactant solution through, for example, manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100%, or 80-100%, or any range or value therein. However, it should be understood that minor sequence variations in the probes and primers can be compensated for by reducing the stringency of the hybridization and/or wash medium.

Methods of amplification of RNA or DNA are well known in the art and can be used according to the present invention without undue experimentation, based on the teaching and guidance presented herein. Known methods of DNA or RNA amplification include, but are not limited to, polymerase chain reaction (PCR) and related amplification processes (see, e.g., U.S. Pat. Nos. 4,683,195, 4,683,202, 4,800,159, 4,965,188, to Mullis, et al.; 4,795,699 and 4,921,794 to Tabor, et al; 5,142,033 to Innis; 5,122,464 to Wilson, et al.; 5,091,310 to Innis; 5,066,584 to Gyllensten, et al; 4,889,818 to Gelfand, et al; 4,994,370 to Silver, et al; 4,766,067 to Biswas; 4,656,134 to Ringold) and RNA mediated amplification that uses anti-sense RNA to the target sequence as a template for double-stranded DNA synthesis (U.S. Pat. No. 5,130,238 to Malek, et al, with the tradename NASBA), the entire contents of which references are incorporated herein by reference. (See, e.g., Ausubel, supra; or Sambrook, supra.)

For instance, polymerase chain reaction (PCR) technology can be used to amplify the sequences of polynucleotides of the present invention and related genes directly from genomic DNA or cDNA libraries. PCR and other in vitro amplification methods can also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, supra, Sambrook, supra, and Ausubel, supra, as well as Mullis, et al., U.S. Pat. No. 4,683,202 (1987); and Innis, et al., PCR Protocols A Guide to Methods and Applications, Eds., Academic Press Inc., San Diego, Calif. (1990). Commercially available kits for genomic PCR amplification are known in the art. See, e.g., Advantage-GC Genomic PCR Kit (Clontech). Additionally, e.g., the T4 gene 32 protein (Boehringer Mannheim) can be used to improve yield of long PCR products.

D.6. Synthetic Methods for Constructing Nucleic Acids

The isolated nucleic acids of the present invention can also be prepared by direct chemical synthesis by known methods (see, e.g., Ausubel, et al., supra). Chemical synthesis generally produces a single-stranded oligonucleotide, which can be converted into double-stranded DNA by hybridization with a complementary sequence, or by polymerization with a DNA polymerase using the single strand as a template. One of skill in the art will recognize that while chemical synthesis of DNA can be limited to sequences of about 100 or more bases, longer sequences can be obtained by the ligation of shorter sequences.

E. Production of EST Proteins

It is envisioned that the EST polypeptides of this invention may be produced by cell lines derived from bacteria, yeast, insect, or mammal. Recombinant expression cassettes comprising the nucleic acid of the novel polypeptides are also provided for in this invention. The recombinant expression cassette can be introduced into at least one host cell. Vectors containing necessary promoter elements may be used to express Gas6 ESTs. Nucleic acid sequences encoding a Gas6 EST in conjunction with a signal peptide and any other epitope may be included to facilitate secretion and purification of desired polypeptides. Those of ordinary skill in the art are knowledgeable in the numerous expression systems available for expression of a nucleic acid encoding a peptide of the present invention.

F. Generation of Polyclonal Antibodies

The isolated peptides and/or polypeptides of the present invention can be used for production of at least one anti-Gas6 antibody or specified variant thereof, which can be used to measure or effect in a cell, tissue, organ or animal (including mammals and humans), to diagnose, monitor, modulate, treat, alleviate, help prevent the incidence of, or reduce the symptoms of, at least one Gas6 condition, selected from, but not limited to, at least one of an immune disorder or disease, a cardiovascular disorder or disease, an infectious, malignant, and/or neurologic disorder or disease, or other known or specified Gas6 related condition.

The present invention provides isolated, recombinant and/or synthetic anti-Gas6 human, primate, rodent, mammalian, chimeric, humanized or CDR-grafted, antibodies and Gas6 anti-idiotype antibodies thereto, as well as compositions, encoding amino acid sequences, and encoding nucleic acid molecules comprising at least one polynucleotide encoding at least one anti-Gas6 antibody or anti-idiotype antibody. The present invention further includes, but is not limited to, methods of making and using such nucleic acids and antibodies and anti-idiotype antibodies, including diagnostic and therapeutic compositions, methods and devices.

F.1. Definition & Characterization of an Anti-Gas6 Antibody

As used herein, an "anti-Gas6 antibody," "anti-Gas6 antibody portion," or "anti-Gas6 antibody fragment" and/or "anti-Gas6 antibody variant" and the like include any protein or polypeptide containing molecule that comprises at least a portion of an immunoglobulin molecule, such as but not limited to at least one complementarity determining region (CDR) of a heavy or light chain or a ligand binding portion thereof, a heavy chain or light chain variable region, a heavy chain or light chain constant region, a framework region, or any portion thereof, or at least one portion of a Gas6 receptor or binding protein derived from a Gas6 protein or peptide of the invention, which can be incorporated into an antibody of the present invention. Such antibody optionally further affects a specific ligand, such as but not limited to where such antibody modulates, decreases, increases, antagonizes, angonizes, mitigates, alleviates, blocks, inhibits, abrogates and/or interferes with at least one Gas6 activity or binding, or with Gas6 receptor activity or binding, in vitro, in situ and/or in vivo. As a non-limiting example, a suitable anti-Gas6 antibody, specified portion or variant of the present invention can bind at least one Gas6 protein or peptide of the invention, or specified portions, variants or domains thereof. A suitable anti-Gas6 antibody, specified portion, or variant can also optionally affect at least one of Gas6 activity or function, such as but not limited to, RNA, DNA or protein synthesis, Gas6 release, Gas6 receptor signaling, Gas6 activity, Gas6 production and/or synthesis. The term "antibody" is further intended to encompass antibodies, digestion fragments, specified portions and variants thereof, including antibody mimetics or comprising portions of antibodies that mimic the structure and/or function of an antibody or specified fragment or portion thereof, including single chain antibodies and fragments thereof. Functional fragments include antigen-binding fragments that bind to a mammalian Gas6. For example, antibody fragments capable of binding to Gas6 or portions thereof, including, but not limited to Fab (e.g., by papain digestion), Fab' (e.g., by pepsin digestion and partial reduction) and F(ab')2 (e.g., by pepsin digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments, are encompassed by the invention (see, e.g., Colligan, Immunology, supra).

Such fragments can be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. For example, a combination gene encoding a F(ab')2 heavy chain portion can be designed to include DNA sequences encoding the CH1 domain and/or hinge region of the heavy chain. The various portions of antibodies can be joined together chemically by conventional techniques, or can be prepared as a contiguous protein using genetic engineering techniques.

As used herein, the term "human antibody" refers to an antibody in which substantially every part of the protein (e.g., CDR, framework, CL, CH domains (e.g., CH1, CH2, CH3), hinge, (VL, VH)) is substantially non-immunogenic in humans, with only minor sequence changes or variations. Similarly, antibodies designated primate (monkey, baboon, chimpanzee, etc.), rodent (mouse, rat, rabbit, guinea pig, hamster, and the like) and other mammals designate such species, sub-genus, genus, sub-family, family specific antibodies. Further, chimeric antibodies of the invention can include any combination of the above. Such changes or variations optionally and preferably retain or reduce the immunogenicity in humans or other species relative to non-modified antibodies. Thus, a human antibody is distinct from a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, a Fv can comprise a linker peptide, such as 2 to about 8 glycine or other amino acid residues, which connects the variable region of the heavy chain and the variable region of the light chain. Such linker peptides are considered to be of human origin.

Bispecific, heterospecific, heteroconjugate or similar antibodies can also be used that are monoclonal, preferably human or humanized, antibodies that have binding specificities for at least two different antigens. In the present case, one of the binding specificities is for at least one Gas6 protein of the invention, the other one is for any other antigen. Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, Nature 305:537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed, e.g., in WO 93/08829, U.S. Pat. Nos. 6,210,668, 6,193,967, 6,132,992, 6,106,833, 6,060,285, 6,037,453, 6,010,902, 5,989,530, 5,959,084, 5,959,083, 5,932,448, 5,833,985, 5,821,333, 5,807,706, 5,643,759, 5,601,819, 5,582,996, 5,496,549, 4,676,980, WO 91/00360, WO 92/00373, EP 03089, Traunecker et al., EMBO J. 10:3655 (1991), Suresh et al., Methods in Enzymology 121:210 (1986), each entirely incorporated herein by reference.

Anti-Gas6 antibodies useful in the methods and compositions of the present invention can optionally be characterized by high affinity binding to Gas6 and optionally and preferably having low toxicity. In particular, an antibody, specified fragment or variant of the invention, where the individual components, such as the variable region, constant region and framework, individually and/or collectively, optionally and preferably possess low immunogenicity, is useful in the present invention. The antibodies that can be used in the invention are optionally characterized by their ability to treat patients for extended periods with measurable alleviation of symptoms and low and/or acceptable toxicity. Low or acceptable immunogenicity and/or high affinity, as well as other suitable properties, can contribute to the therapeutic results achieved. "Low immunogenicity" is defined herein as raising significant HAHA, HACA or HAMA responses in less than about 75%, or preferably less than about 50% of the patients treated and/or raising low titres in the patient treated (less than about 300, preferably less than about 100 measured with a double antigen enzyme immunoassay) (Elliott et al., Lancet 344:1125-1127 (1994), entirely incorporated herein by reference).

Application of the anti-Gas6 antibody can comprise administering an effective amount of a composition or a pharmaceutical composition comprising at least one anti-Gas6 antibody to a cell, tissue, organ, animal or patient in need of such modulation, treatment, alleviation, prevention, or reduction in symptoms, effects or mechanisms. The effective amount can comprise an amount of about 0.001 to 500 mg/kg per single (e.g., bolus), multiple or continuous administration, or to achieve a serum concentration of 0.01-5000 µg/ml serum concentration per single, multiple, or continuous administration, or any effective range or value therein, as done and determined using known methods, as described herein or known in the relevant arts.

F.2. Amino Acid Codes for Anti-Gas6 Antibodies

As those of skill will appreciate, the present invention includes at least one biologically active antibody of the present invention. Biologically active antibodies have a specific activity at least 20%, 30%, or 40%, and preferably at least 50%, 60%, or 70%, and most preferably at least 80%, 90%, or 95%-100% of that of the native (non-synthetic), endogenous or related and known antibody. Methods of assaying and quantifying measures of enzymatic activity and substrate specificity are well known to those of skill in the art.

In another aspect, the invention relates to human antibodies and antigen-binding fragments, as described herein, which are modified by the covalent attachment of an organic moiety. Such modification can produce an antibody or antigen-binding fragment with improved pharmacokinetic properties (e.g., increased in vivo serum half-life). The organic moiety can be a linear or branched hydrophilic polymeric group, fatty acid group, fatty acid ester group. Lipid molecules such as a disteroylphosphatidyl ethanolamine moiety, either alone or covalently bonded to a hydrophilic polymer, are useful. In particular embodiments, the hydrophilic polymeric group can have a molecular weight of about 800 to about 120,000 Daltons and can be a polyalkane glycol (e.g., polyethylene glycol (PEG), polypropylene glycol (PPG)), carbohydrate polymer, amino acid polymer or polyvinyl pyrolidone, and the fatty acid or fatty acid ester group can comprise from about eight to about forty carbon atoms.

The modified antibodies and antigen-binding fragments of the invention can comprise one or more organic moieties that are covalently bonded, directly or indirectly, to the antibody. Each organic moiety that is bonded to an antibody or antigen-binding fragment of the invention can independently be a hydrophilic polymeric group, a fatty acid group or a fatty acid ester group. As used herein, the term "fatty acid" encompasses mono-carboxylic acids and di-carboxylic acids. A "hydrophilic polymeric group," as the term is used herein, refers to an organic polymer that is more soluble in water than in octane. For example, polylysine is more soluble in water than in octane. Thus, an antibody modified by the covalent attachment of polylysine is encompassed by the invention. Hydrophilic polymers suitable for modifying antibodies of the invention can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. Preferably, the hydrophilic polymer that modifies the antibody of the invention has a molecular weight of about 800 to about 150,000 Daltons as a separate molecular entity. For example PEG5000 and PEG20,000, wherein the subscript is the average molecular weight of the polymer in Daltons, can be used. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N,N-carbonyl diimidazole) on a fatty acid or fatty acid ester can be coupled to a hydroxyl group on a polymer.

Fatty acids and fatty acid esters suitable for modifying antibodies of the invention can be saturated or can contain one or more units of unsaturation. Fatty acids that are suitable for modifying antibodies of the invention include, for example, n-dodecanoate (C12, laurate), n-tetradecanoate (C14, myristate), n-octadecanoate (C18, stearate), n-eicosanoate (C20, arachidate), n-docosanoate (C22, behenate), n-triacontanoate (C30), n-tetracontanoate (C40), cis-$\Delta$9-octadecanoate (C18, oleate), all cis-$\Delta$5,8,11,14-eicosatetraenoate (C20, arachidonate), octanedioic acid, tetradecanedioic acid, octadecanedioic acid, docosanedioic acid, and the like. Suitable fatty acid esters include mono-esters of dicarboxylic acids that comprise a linear or branched lower alkyl group. The lower alkyl group can comprise from one to about twelve, preferably one to about six, carbon atoms.

The modified human antibodies and antigen-binding fragments can be prepared using suitable methods, such as by reaction with one or more modifying agents. A "modifying agent" as the term is used herein, refers to a suitable organic group (e.g., hydrophilic polymer, a fatty acid, a fatty acid ester) that comprises an activating group. An "activating group" is a chemical moiety or functional group that can, under appropriate conditions, react with a second chemical group thereby forming a covalent bond between the modifying agent and the second chemical group. For example, amine-reactive activating groups include electrophilic groups such as tosylate, mesylate, halo (chloro, bromo, fluoro, iodo), N-hydroxysuccinimidyl esters (NHS), and the like. Activating groups that can react with thiols include, for example, maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, Hermanson, G. T., Bioconjugate Techniques, Academic Press: San Diego, Calif. (1996)). An activating group can be bonded directly to the organic group (e.g., hydrophilic polymer, fatty acid, fatty acid ester), or through a linker moiety, for example a divalent C1-C12 group wherein one or more carbon atoms can be replaced by a heteroatom such as oxygen, nitrogen or sulfur. Suitable linker moieties include, for example, tetraethylene glycol, —(CH2)3-, —NH—(CH2)6-NH—, —(CH2)2-NH— and —CH2—O—CH2—CH2-O—CH2-CH2-O—CH—NH—. Modifying agents that comprise a linker moiety can be produced, for example, by reacting a mono-Boc-alkyldiamine (e.g., mono-Boc-ethylenediamine, mono-Boc-diaminohexane) with a fatty acid in the presence of 1-ethyl-3-(3-dimethylaminopropyl) carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate as described, or can be reacted with maleic anhydride and the resulting product cyclized to produce an activated maleimido derivative of the fatty acid. (See, for example, Thompson, et al., WO 92/16221 the entire teachings of which are incorporated herein by reference.)

The modified antibodies of the invention can be produced by reacting a human antibody or antigen binding fragment with a modifying agent. For example, the organic moieties can be bonded to the antibody in a non-site specific manner by employing an amine-reactive modifying agent, for example, a NHS ester of PEG. Modified human antibodies or antigen-binding fragments can also be prepared by reducing disulfide bonds (e.g., intra-chain disulfide bonds) of an antibody or antigen-binding fragment. The reduced antibody or antigen-binding fragment can then be reacted with a thiol-reactive modifying agent to produce the modified antibody of the invention. Modified human antibodies and antigen-binding fragments comprising an organic moiety that is bonded to specific sites of an antibody of the present invention can be prepared using suitable methods, such as reverse proteolysis (Fisch et al., Bioconjugate Chem., 3:147-153 (1992); Werlen et al., Bioconjugate Chem., 5:411-417 (1994); Kumaran et al., Protein Sci. 6(10):2233-2241 (1997); Itoh et al., Bioorg. Chem., 24(1): 59-68 (1996); Capellas et al., Biotechnol. Bioeng., 56(4):456-463 (1997)), and the methods described in Hermanson, G. T., Bioconjugate Techniques, Academic Press: San Diego, Calif. (1996).

F.3. Nucleic Acid Molecules

The present invention includes the detailed description of nucleic acid molecules as presented in section D.1. In addition, and as indicated herein, nucleic acid molecules of the present invention which comprise a nucleic acid encoding an anti-Gas6 antibody can include, but are not limited to, those encoding the amino acid sequence of an antibody fragment, by itself, the coding sequence for the entire antibody or a portion thereof; the coding sequence for an antibody, fragment or portion as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example—ribosome binding and stability of mRNA); an additional coding sequence that codes for additional amino acids, such as those that provide additional functionalities. Thus, the sequence encoding a polypeptide or antibody can be fused to a marker sequence, such as a sequence encoding a peptide that facilitates purification of the fused antibody comprising an antibody fragment or portion.

In addition and as stated in sections D.2., D.3., D.4., D.5., and D.6., the present invention provides for those nucleic acids that hybridize under selective hybridization conditions to a polynucleotide disclosed herein; the construction of nucleic acids using (a) recombinant methods, (b) synthetic techniques, (c) purification techniques, or combinations thereof, as well known in the art.

F.4. Recombinant Expression Cassettes

The present invention further provides recombinant expression cassettes comprising a nucleic acid of the present invention. A nucleic acid sequence of the present invention, for example a cDNA or a genomic sequence encoding an antibody of the present invention, can be used to construct a recombinant expression cassette that can be introduced into at least one desired host cell. A recombinant expression cassette will typically comprise a polynucleotide of the present invention operably linked to transcriptional initiation regulatory sequences that will direct the transcription of the polynucleotide in the intended host cell. Both heterologous and non-heterologous (i.e., endogenous) promoters can be employed to direct expression of the nucleic acids of the present invention.

In some embodiments, isolated nucleic acids that serve as promoter, enhancer, or other elements can be introduced in the appropriate position (upstream, downstream or in intron) of a non-heterologous form of a polynucleotide of the present invention so as to up or down regulate expression of a polynucleotide of the present invention. For example, endogenous promoters can be altered in vivo or in vitro by mutation, deletion and/or substitution.

F.5. Vectors and Host Cells

The present invention also relates to vectors that include isolated nucleic acid molecules of the present invention, host cells that are genetically engineered with the recombinant vectors, and the production of at least one anti-Gas6 antibody by recombinant techniques, as is well known in the art. See, e.g., Sambrook, et al., supra; Ausubel, et al., supra, each entirely incorporated herein by reference.

The polynucleotides can optionally be joined to a vector containing a selectable marker for propagation in a host. Generally, a plasmid vector is introduced in a precipitate, such as a calcium phosphate precipitate, or in a complex with a charged lipid. If the vector is a virus, it can be packaged in vitro using an appropriate packaging cell line and then transduced into host cells.

The DNA insert should be operatively linked to an appropriate promoter. The expression constructs will further contain sites for transcription initiation, termination and, in the transcribed region, a ribosome binding site for translation. The coding portion of the mature transcripts expressed by the constructs will preferably include a translation initiating at the beginning and a termination codon (e.g., UAA, UGA or UAG) appropriately positioned at the end of the mRNA to be translated, with UAA and UAG preferred for mammalian or eukaryotic cell expression.

Expression vectors will preferably but optionally include at least one selectable marker. Such markers include, e.g., but not limited to, methotrexate (MTX), dihydrofolate reductase (DHFR, U.S. Pat. Nos. 4,399,216; 4,634,665; 4,656,134; 4,956,288; 5,149,636; 5,179,017, ampicillin, neomycin (G418), mycophenolic acid, or glutamine synthetase (GS, U.S. Pat. Nos. 5,122,464; 5,770,359; 5,827,739) resistance for eukaryotic cell culture, and tetracycline or ampicillin resistance genes for culturing in *E. coli* and other bacteria or prokaryotics (the above patents are entirely incorporated hereby by reference). Appropriate culture mediums and conditions for the above-described host cells are known in the art. Suitable vectors will be readily apparent to the skilled artisan. Introduction of a vector construct into a host cell can be effected by calcium phosphate transfection, DEAE-dextran mediated transfection, cationic lipid-mediated transfection, electroporation, transduction, infection or other known methods. Such methods are described in the art, such as Sambrook, supra, Chapters 1-4 and 16-18; Ausubel, supra, Chapters 1, 9, 13, 15, 16.

At least one antibody of the present invention can be expressed in a modified form, such as a fusion protein, and can include not only secretion signals, but also additional heterologous functional regions. For instance, a region of additional amino acids, particularly charged amino acids, can be added to the N-terminus of an antibody to improve stability and persistence in the host cell, during purification, or during subsequent handling and storage. Also, peptide moieties can be added to an antibody of the present invention to facilitate purification. Such regions can be removed prior to final preparation of an antibody or at least one fragment thereof. Such methods are described in many standard laboratory manuals, such as Sambrook, supra, Chapters 17.29-17.42 and 18.1-18.74; Ausubel, supra, Chapters 16, 17 and 18.

Those of ordinary skill in the art are knowledgeable in the numerous expression systems available for expression of a nucleic acid encoding a protein of the present invention.

Alternatively, nucleic acids of the present invention can be expressed in a host cell by turning on (by manipulation) in a host cell that contains endogenous DNA encoding an antibody of the present invention. Such methods are well known in the art, e.g., as described in U.S. Pat. Nos. 5,580,734, 5,641,670, 5,733,746, and 5,733,761, entirely incorporated herein by reference.

Illustrative of cell cultures useful for the production of the antibodies, specified portions or variants thereof, are mammalian cells. Mammalian cell systems often will be in the form of monolayers of cells although mammalian cell suspensions or bioreactors can also be used. A number of suitable host cell lines capable of expressing intact glycosylated proteins have been developed in the art, and include the COS-1 (e.g., ATCC CRL 1650), COS-7 (e.g., ATCC CRL-1651), HEK293, BHK21 (e.g., ATCC CRL-10), CHO (e.g., ATCC CRL 1610) and BSC-1 (e.g., ATCC CRL-26) cell lines, Cos-7 cells, CHO cells, hep G2 cells, P3X63Ag8.653, SP2/0-Ag14, 293 cells, HeLa cells and the like, which are readily available from, for example, American Type Culture Collection, Manassas, Va. (www.atcc.org). Preferred host cells include cells of lymphoid origin such as myeloma and lymphoma cells. Particularly preferred host cells are P3X63Ag8.653 cells (ATCC Accession Number CRL-1580) and SP2/0-Ag14 cells (ATCC Accession Number CRL-1851). In a particularly preferred embodiment, the recombinant cell is a P3X63Ab8.653 or a SP2/0-Ag14 cell.

Expression vectors for these cells can include one or more of the following expression control sequences, such as, but not limited to an origin of replication; a promoter (e.g., late or early SV40 promoters, the CMV promoter (U.S. Pat. Nos. 5,168,062; 5,385,839), an HSV tk promoter, a pgk (phosphoglycerate kinase) promoter, an EF-1 alpha promoter (U.S. Pat. No. 5,266,491), at least one human immunoglobulin promoter; an enhancer, and/or processing information sites, such as ribosome binding sites, RNA splice sites, polyadenylation sites (e.g., an SV40 large T Ag poly A addition site), and transcriptional terminator sequences. See, e.g., Ausubel et al., supra; Sambrook, et al., supra. Other cells useful for production of nucleic acids or proteins of the present invention are known and/or available, for instance, from the American Type Culture Collection Catalogue of Cell Lines and Hybridomas (www.atcc.org) or other known or commercial sources.

When eukaryotic host cells are employed, polyadenlyation or transcription terminator sequences are typically incorporated into the vector. An example of a terminator sequence is the polyadenlyation sequence from the bovine growth hormone gene. Sequences for accurate splicing of the transcript can also be included. An example of a splicing sequence is the VP1 intron from SV40 (Sprague, et al., J. Virol. 45:773-781 (1983)). Additionally, gene sequences to control replication in the host cell can be incorporated into the vector, as known in the art.

G. Generation of Monoclonal Antibodies

Monoclonal antibodies of this invention may be raised by traditional immunization and hybridoma technology. After immunization of mice with human Gas6 antigens, spleen cells or lymphocytes from lymph node tissue from immunized animals are recovered and immortalized by fusion with myeloma cells or by Epstein-Barr (EB)-virus transformation. Monoclonal antibodies are obtained by screening for clones expressing the desired antibody. While mice are frequently employed as the test model, it is contemplated that any mammalian subject including human subjects or antibody-producing cells can be manipulated according to the processes of this invention to serve as the basis for production of mammalian, including human and hybrid cell lines. Techniques for cloning recombinant DNA of antibody molecule directly from an antibody-expressing B cell are within the scope of this invention. Such B cells can be isolated by the fluorescence activated cell sorter [63].

While routinely mouse monoclonal antibodies are generated, the invention is not so limited. For therapeutic applications, human antibodies are desired. Such antibodies can be obtained by using human hybridomas [64] or by generating humanized antibodies. Humanized antibodies can be developed by replacing the specific segments of a non-human antibody with corresponding segments of a human antibody gene. This process retains most or all of CDR regions of the light and heavy chain variable regions of parental antibody and largely replaces the framework regions with human sequences [EP Patent No. 184187; EP Patent No. 171496; EP Patent No. 173494 and WO Patent No. 8601533]. Human monoclonal antibodies are also generated in transgenic mice that contain genes or gene segments encoding human antibodies in their genome [U.S. Pat. No. 6,162,963; WO Patent No. 9312227; U.S. Pat. No. 5,877,5397; U.S. Pat. No. 5,874, 299; U.S. Pat. No. 5,814,318; U.S. Pat. No. 5,789,650; U.S. Pat. No. 5,770,429; U.S. Pat. No. 5,661,016; U.S. Pat. No. 5,625,126; U.S. Pat. No. 5,569,825; U.S. Pat. No. 5,545,806; and WO Patent No. 9110741].

Human monoclonal antibodies are also obtained from recombinant antibody libraries, generated in vitro or in vivo, using phage display, ribosome display, or related screening or selection techniques. Examples of procedures for generating antibody libraries, primarily of human origin are disclosed by A. Knappik and others [65] [U.S. Pat. No. 6,291,158; U.S. Pat. No. 6,291,159; U.S. Pat. No. 6,291,160 and U.S. Pat. No. 6,291,161]. Examples of methods for selections of human antibodies to specific antigens targets from such libraries are disclosed by B. Krebs and others [66] [U.S. Pat. No. 5,955, 341; U.S. Pat. No. 5,759,817; U.S. Pat. No. 5,658,727; U.S. Pat. No. 6,235,469; U.S. Pat. No. 5,969,108; U.S. Pat. No. 5,886,793].

G.1. Detailed Description of Methods to Generate Anti-Gas6 Antibodies

At least one anti-Gas6 antibody of the present invention can be optionally produced by a cell line, a mixed cell line, an immortalized cell or clonal population of immortalized cells, as well known in the art. See, e.g., Ausubel, et al., ed., Current Protocols in Molecular Biology, John Wiley & Sons, Inc., NY, N.Y. (1987-2001); Sambrook, et al., Molecular Cloning: A Laboratory Manual, 2nd Edition, Cold Spring Harbor, N.Y. (1989); Harlow and Lane, antibodies, a Laboratory Manual, Cold Spring Harbor, N.Y. (1989); Colligan, et al., eds., Current Protocols in Immunology, John Wiley & Sons, Inc., NY (1994-2001); Colligan et al., Current Protocols in Protein Science, John Wiley & Sons, NY, N.Y., (1997-2001), each entirely incorporated herein by reference.

Human antibodies that are specific for human Gas6 proteins or fragments thereof can be raised against an appropriate immunogenic antigen as described herein, such as the isolated and/or Gas6 proteins or portions thereof (including synthetic molecules, such as synthetic peptides) as described herein. Other specific or general mammalian antibodies can be similarly raised. Preparation of immunogenic antigens, and monoclonal antibody production can be performed using any suitable technique.

In one approach, a hybridoma is produced by fusing a suitable immortal cell line (e.g., a myeloma cell line such as, but not limited to, Sp2/0, Sp2/0-AG14, NSO, NS1, NS2, AE-1, L.5, >243, P3X63Ag8.653, Sp2 SA3, Sp2 MAI, Sp2 SS1, Sp2 SA5, U937, MLA 144, ACT IV, MOLT4, DA-1, JURKAT, WEHI, K-562, COS, RAJI, NIH 3T3, HL-60, MLA 144, NAMAIWA, NEURO 2A, or the like, or heteromylomas, fusion products thereof, or any cell or fusion cell derived therefrom, or any other suitable cell line as known in the art. See, e.g., www.atcc.org, www.lifetech.com., and the like, with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. See, e.g., Ausubel, supra, and Colligan, Immunology, supra, chapter 2, entirely incorporated herein by reference.

Antibody producing cells can also be obtained from the peripheral blood or, preferably the spleen or lymph nodes, of humans or other suitable animals that have been immunized with the antigen of interest. Any other suitable host cell can also be used for expressing heterologous or endogenous nucleic acid encoding an antibody, specified fragment or variant thereof, of the present invention. The fused cells (hybridomas) or recombinant cells can be isolated using selective culture conditions or other suitable known methods, and cloned by limiting dilution or cell sorting, or other known methods. Cells which produce antibodies with the desired specificity can be selected by a suitable assay (e.g., ELISA).

Other suitable methods of producing or isolating antibodies of the requisite specificity can be used, including, but not limited to, methods that select recombinant antibody from a peptide or protein display library (e.g., but not limited to, a bacteriophage, ribosome, oligonucleotide, RNA, cDNA, or the like, display library; e.g., as available from Cambridge antibody Technologies, Cambridgeshire, UK; MorphoSys, Martinsreid/Planegg, Del.; Biovation, Aberdeen, Scotland, UK; BioInvent, Lund, Sweden; Dyax Corp., Enzon, Affymax/Biosite; Xoma, Berkeley, Calif.; Ixsys. See, e.g., EP 368,684, PCT/GB91/01134; PCT/GB92/01755; PCT/GB92/002240; PCT/GB92/00883; PCT/GB93/00605; U.S. Ser. No. 08/350,260(May 12, 1994); PCT/GB94/01422; PCT/GB94/02662; PCT/GB97/01835; (CAT/MRC); WO90/14443; WO90/14424; WO90/14430; PCT/US94/1234; WO92/18619; WO96/07754; (Scripps); WO96/13583, WO97/08320 (MorphoSys); WO95/16027 (BioIvent); WO88/06630; WO90/3809 (Dyax); U.S. Pat. No. 4,704,692 (Enzon); PCT/US91/02989 (Affymax); WO89/06283; EP 371 998; EP 550 400; (Xoma); EP 229 046; PCT/US91/07149 (Ixsys); or stochastically generated peptides or proteins—U.S. Pat. Nos. 5,723,323, 5,763,192, 5,814,476, 5,817,483, 5,824,514, 5,976,862, WO 86/05803, EP 590 689 (Ixsys, now Applied Molecular Evolution (AME), each entirely incorporated herein by reference) or that rely upon immunization of transgenic animals (e.g., SCID mice, Nguyen et al., Microbiol. Immunol. 41:901-907 (1997); Sandhu et al., Crit. Rev. Biotechnol. 16:95-118 (1996); Eren et al., Immunol. 93:154-161 (1998), each entirely incorporated by reference as well as related patents and applications) that are capable of producing a repertoire of human antibodies, as known in the art and/or as described herein. Such techniques, include, but are not limited to, ribosome display (Hanes et al., Proc. Natl. Acad. Sci. USA, 94:4937-4942 (May 1997); Hanes et al., Proc. Natl. Acad. Sci. USA, 95:14130-14135 (November 1998)); single cell antibody producing technologies (e.g., selected lymphocyte antibody method ("SLAM") (U.S. Pat. No. 5,627,052, Wen et al., J. Immunol. 17:887-892 (1987); Babcook et al., Proc. Natl. Acad. Sci. USA 93:7843-7848 (1996)); gel microdroplet and flow cytometry (Powell et al., Biotechnol. 8:333-337 (1990); One Cell Systems, Cambridge, Mass.; Gray et al., J. Imm. Meth. 182:155-163 (1995); Kenny et al., Bio/Technol. 13:787-790 (1995)); B-cell selection (Steenbakkers et al., Molec. Biol. Reports 19:125-134 (1994); Jonak et al., Progress Biotech, Vol. 5, In Vitro Immunization in Hybridoma Technology, Borrebaeck, ed., Elsevier Science Publishers B.V., Amsterdam, Netherlands (1988)).

Methods for engineering or humanizing non-human or human antibodies can also be used and are well known in the art. Generally, a humanized or engineered antibody has one or more amino acid residues from a source which is non-human, e.g., but not limited to mouse, rat, rabbit, non-human primate or other mammal. These human amino acid residues are often referred to as "import" residues, which are typically taken from an "import" variable, constant or other domain of a known human sequence. Known human Ig sequences are disclosed, e.g.,
www._ ncbi.nlm.nih.gov/entrez/query.fcgi;
www._ atcc.org/phage/hdb.html; www._ sciquest.com/;
www._ abcam.com/; www._ antibodyresource.com/onlinecomp.html;www. www._ public.iastate.edu/~pedro/research_tools.html;
www._ mgen.uni-heidelberg.de/SD/IT/IT.html;
www._ whfreeman.com/immunology/CH05/kuby05.htm;
www._ library.thinkquest.org/12429/Immune/Antibody.html;
www._ hhmi.org/grants/lectures/1996/vlab/;
www._ path.cam.ac.uk/~mrc7/mikeimages.html;
www._ antibodyresource.com/;
mcb.harvard.edu/BioLinks/Immunology.html.
www._ immunologylink.com/; pathbox.wustl.edu/~hcenter/index.html;
www._ biotech.ufl.edu/~hcl/;
www._ pebio.com/pa/340913/340913.html;
www._ nal.usda.gov/awic/pubs/antibody/;
www._ m.ehime-u.acjp/~yasuhito/Elisa.html;
www._ biodesign.com/table.asp;
www._ icnet.uk/axp/facs/davies/links.html;
www._ biotech.ufl.edu/~fccl/protocol.html; www._ isacnet.org/sites_geo.html; aximt1.imt.uni-marburg.de/~rek/AEPStart.html; baserv.uci.kun.nl/~jraats/links1.html; www._ recab.uni -hd.de/immuno.bme.nwu.edu/; www._ mrc-cpe.cam.ac.uk/imt-doc/public/INTRO.html; www. ibt.unam.mx/vir/V_mice.html; imgt.cnusc.fr:8104/;
www._ biochem.ucl.ac.uk/~martin/abs/index.html; antibody.bath.ac.uk/;
abgen.cvm.tamu.edu/lab/wwwabgen.html;
www._ unizh.ch/~honegger/AHOseminar/Slide01.html;
www._ cryst.bbk.ac.uk/~ubcg07s/;
www._ nimr.mrc.ac.uk/CC/ccaewg/ccaewg.htm;
www._ path.cam.ac.uk/~mrc7/humanisation/TAHHP.html;
www._ ibt.unam.mx/vir/structure/stat_aim.html;
www._ biosci.missouri.edu/smithgp/index.html;
www._ cryst.bioc.cam.ac.uk/~fmolina/Web-pages/Pept/spottech.html;
www._ jerini.de/fr_products.htm; www._ patents.ibm.com/ibm.html.Kabat et al., Sequences of Proteins of Immunological Interest, U.S. Dept. Health (1983), each entirely incorporated herein by reference.

Such imported sequences can be used to reduce immunogenicity or reduce, enhance or modify binding, affinity, on-rate, off-rate, avidity, specificity, half-life, or any other suitable characteristic, as known in the art. Generally part or all of the non-human or human CDR sequences are maintained while the non-human sequences of the variable and constant regions are replaced with human or other amino acids antibodies can also optionally be humanized with retention of high affinity for the antigen and other favorable biological properties. To achieve this goal, humanized antibodies can be optionally prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Humanization or engineering of antibodies of the present invention can be performed using any known method, such as but not limited to those described in, Winter (Jones et al., Nature 321:522 (1986); Riechmann et al., Nature 332:323 (1988); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,723,323, 5,976,862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; 4,816,567, PCT/US98/16280, US96/18978, US91/09630, US91/05939, US94/01234, GB89/01334, GB91/01134, GB92/01755; WO90/14443, WO90/14424, WO90/14430, EP 229246, each entirely incorporated herein by reference, included references cited therein.

The anti-Gas6 antibody can also be optionally generated by immunization of a transgenic animal (e.g., mouse, rat, hamster, non-human primate, and the like) capable of producing a repertoire of human antibodies, as described herein and/or as known in the art. Cells that produce a human anti-Gas6 antibody can be isolated from such animals and immortalized using suitable methods, such as the methods described herein.

Transgenic mice that can produce a repertoire of human antibodies that bind to human antigens can be produced by known methods (e.g., but not limited to, U.S. Pat. Nos. 5,770,428, 5,569,825, 5,545,806, 5,625,126, 5,625,825, 5,633,425, 5,661,016 and 5,789,650 issued to Lonberg et al.; Jakobovits et al. WO 98/50433, Jakobovits et al. WO 98/24893, Lonberg et al. WO 98/24884, Lonberg et al. WO 97/13852, Lonberg et al. WO 94/25585, Kucherlapate et al. WO 96/34096, Kucherlapate et al. EP 0463 151 B1, Kucherlapate et al. EP 0710 719 A1, Surani et al. U.S. Pat. No. 5,545,807, Bruggemann et al. WO 90/04036, Bruggemann et al. EP 0438 474 B1, Lonberg et al. EP 0814 259 A2, Lonberg et al. GB 2 272 440 A, Lonberg et al. Nature 368:856-859 (1994), Taylor et al., Int. Immunol. 6(4)579-591 (1994), Green et al, Nature Genetics 7:13-21 (1994), Mendez et al., Nature Genetics 15:146-156 (1997), Taylor et al., Nucleic Acids Research 20(23):6287-6295 (1992), Tuaillon et al., Proc Natl Acad Sci USA 90(8)3720-3724 (1993), Lonberg et al., Int Rev Immunol 13(1):65-93 (1995) and Fishwald et al., Nat Biotechnol 14(7):845-851 (1996), which are each entirely incorporated herein by reference). Generally, these mice comprise at least one transgene comprising DNA from at least one human immunoglobulin locus that is functionally rearranged, or which can undergo functional rearrangement. The endogenous immunoglobulin loci in such mice can be disrupted or deleted to eliminate the capacity of the animal to produce antibodies encoded by endogenous genes.

Screening antibodies for specific binding to similar proteins or fragments can be conveniently achieved using peptide display libraries. This method involves the screening of large collections of peptides for individual members having the desired function or structure. Antibody screening of peptide display libraries is well known in the art. The displayed peptide sequences can be from 3 to 5000 or more amino acids in length, frequently from 5-100 amino acids long, and often from about 8 to 25 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT Patent Publication Nos. 91/17271, 91/18980, 91/19818, and 93/08278. Other systems for generating libraries of peptides have aspects of both in vitro chemical synthesis and recombinant methods. See, PCT Patent Publication Nos. 92/05258, 92/14843, and 96/19256. See also, U.S. Pat. Nos. 5,658,754; and 5,643,768. Peptide display libraries, vector, and screening kits are commercially available from such suppliers as Invitrogen (Carlsbad, Calif.), and Cambridge antibody Technologies (Cambridgeshire, UK). See, e.g., U.S. Pat. Nos. 4,704,692, 4,939,666, 4,946,778, 5,260,203, 5,455,030, 5,518,889, 5,534,621, 5,656,730, 5,763,733, 5,767,260, 5,856,456, assigned to Enzon; 5,223,409, 5,403,484, 5,571, 698, 5,837,500, assigned to Dyax, 5,427,908, 5,580,717, assigned to Affymax; 5885793, assigned to Cambridge antibody Technologies; U.S. Pat. No. 5,750,373, assigned to Genentech, U.S. Pat. Nos. 5,618,920, 5,595,898, 5,576,195, 5,698,435, 5,693,493, 5,698,417, assigned to Xoma, Colligan, supra; Ausubel, supra; or Sambrook, supra, each of the above patents and publications entirely incorporated herein by reference.

Antibodies of the present invention can also be prepared using at least one anti-Gas6 antibody encoding nucleic acid to provide transgenic animals or mammals, such as goats, cows, horses, sheep, and the like, that produce such antibodies in their milk. Such animals can be provided using known methods. See, e.g., but not limited to, U.S. Pat. Nos. 5,827,690; 5,849,992; 4,873,316; 5,849,992; 5,994,616; 5,565,362; 5,304,489, and the like, each of which is entirely incorporated herein by reference.

Antibodies of the present invention can additionally be prepared using at least one anti-Gas6 antibody encoding nucleic acid to provide transgenic plants and cultured plant cells (e.g., but not limited to tobacco and maize) that produce such antibodies, specified portions or variants in the plant parts or in cells cultured therefrom. As a non-limiting example, transgenic tobacco leaves expressing recombinant proteins have been successfully used to provide large amounts of recombinant proteins, e.g., using an inducible promoter. See, e.g., Cramer et al., Curr. Top. Microbol. Immunol. 240:95-118 (1999) and references cited therein. Also, transgenic maize have been used to express mammalian proteins at commercial production levels, with biological activities equivalent to those produced in other recombinant systems or purified from natural sources. See, e.g., Hood et al., Adv. Exp. Med. Biol. 464:127-147 (1999) and references cited therein. Antibodies have also been produced in large amounts from transgenic plant seeds including antibody fragments, such as single chain antibodies (scFv's), including tobacco seeds and potato tubers. See, e.g., Conrad et al., Plant Mol. Biol. 38: 101-109 (1998) and reference cited therein. Thus, antibodies of the present invention can also be produced using transgenic plants, according to know methods. See also, e.g., Fischer et al., Biotechnol. Appl. Biochem. 30:99-108 (October, 1999), Ma et al., Trends Biotechnol. 13:522-7 (1995); Ma et al., Plant Physiol. 109:341-6 (1995); Whitelam et al., Biochem. Soc. Trans. 22:940-944 (1994); and references cited therein. See, also generally for plant expression of antibodies, but not limited to, Each of the above references is entirely incorporated herein by reference.

The antibodies of the invention can bind human Gas6 with a wide range of affinities (KD). In a preferred embodiment, at least one human mAb of the present invention can optionally bind human Gas6 with high affinity. For example, a human mAb can bind human Gas6 with a KD equal to or less than about $10^{-7}$ M, such as but not limited to, 0.1-9.9 (or any range or value therein) X $10^{-7}$, $10^{-8}$, $10^{-9}$, $10^{-10}$, $10^{-11}$, $10^{-12}$, $10^{-13}$ or any range or value therein.

The affinity or avidity of an antibody for an antigen can be determined experimentally using any suitable method. (See, for example, Berzofsky, et al., "Antibody-Antigen Interactions," In Fundamental Immunology, Paul, W. E., Ed., Raven Press: New York, N.Y. (1984); Kuby, Janis Immunology, W. H. Freeman and Company: New York, N.Y. (1992); and methods described herein). The measured affinity of a particular antibody-antigen interaction can vary if measured under different conditions (e.g., salt concentration, pH). Thus, measurements of affinity and other antigen-binding parameters (e.g., KD, Ka, Kd) are preferably made with standardized solutions of antibody and antigen, and a standardized buffer, such as the buffer described herein.

G.2. Purification of an Antibody

An anti-Gas6 antibody can be recovered and purified from recombinant cell cultures by well-known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, N.Y., (1997-2001), e.g., Chapters 1, 4, 6, 8, 9, 10, each entirely incorporated herein by reference.

Antibodies of the present invention include naturally purified products, products of chemical synthetic procedures, and products produced by recombinant techniques from a eukaryotic host, including, for example, yeast, higher plant, insect and mammalian cells. Depending upon the host employed in a recombinant production procedure, the antibody of the present invention can be glycosylated or can be non-glycosylated, with glycosylated preferred. Such methods are described in many standard laboratory manuals, such as Sambrook, supra, Sections 17.37-17.42; Ausubel, supra, Chapters 10, 12, 13, 16, 18 and 20, Colligan, Protein Science, supra, Chapters 12-14, all entirely incorporated herein by reference.

G.3. Anti-Gas6 Antibodies

The isolated antibodies of the present invention comprise any isolated or prepared antibody prepared as described herein. Preferably, the human antibody or antigen-binding fragment binds human Gas6 and, thereby partially or substantially neutralizes at least one biological activity of the protein. An antibody, or specified portion or variant thereof, that partially or preferably substantially neutralizes at least one biological activity of at least one Gas6 protein or fragment can bind the protein or fragment and thereby inhibit activities mediated through the binding of Gas6 to the Gas6 receptor or through other Gas6-dependent or mediated mechanisms. As used herein, the term "neutralizing antibody" refers to an antibody that can inhibit an Gas6-dependent activity by about 20-120%, preferably by at least about 10, 20, 30, 40, 50, 55, 60, 65, 70, 75, 80, 85, 90, 91, 92, 93, 94, 95, 96, 97, 98, 99, 100% or more depending on the assay. The capacity of an anti-Gas6 antibody to inhibit an Gas6-dependent activity is preferably assessed by at least one suitable Gas6 protein or receptor assay, as described herein and/or as known in the art.

A human antibody of the invention can be of any class (IgG, IgA, IgM, IgE, IgD, etc.) or isotype and can comprise a kappa or lambda light chain. In one embodiment, the human antibody comprises an IgG heavy chain or defined fragment, for example, at least one of isotypes, IgG1, IgG2, IgG3 or IgG4. Antibodies of this type can be prepared by employing a transgenic mouse or other transgenic non-human mammal comprising at least one human light chain (e.g., IgG, IgA and IgM (e.g., γ1, γ2, γ3, γ4) transgenes as described herein and/or as known in the art. In another embodiment, the anti-human Gas6 human antibody comprises an IgG1 heavy chain and an IgG1 light chain.

At least one antibody of the invention binds at least one specified epitope specific to at least one Gas6 protein, subunit, fragment, portion or any combination thereof as described herein. The at least one epitope can comprise at least one antibody binding region that comprises at least one portion of the protein sequences corresponding to the peptide sequences from the receptor binding region of human Gas6 as described herein, which epitope is preferably comprised of at least one extracellular, soluble, hydrophilic, external or cytoplasmic portion of the protein.

Generally, the human antibody or antigen-binding fragment of the present invention will comprise an antigen-binding region that comprises at least one human complementarity determining region (CDR1, CDR2 and CDR3) or variant of at least one heavy chain variable region and at least one human complementarity determining region (CDR1, CDR2 and CDR3) or variant of at least one light chain variable region. As a non-limiting example, the antibody or antigen-binding portion or variant can comprise at least one of the heavy chain CDR3 and/or a light chain. In a particular embodiment, the antibody or antigen-binding fragment can have an antigen-binding region that comprises at least a portion of at least one heavy chain CDR (i.e., CDR1, CDR2 and/or CDR3) having the amino acid sequence of the corresponding CDRs 1, 2 and/or 3. In another particular embodiment, the antibody or antigen-binding portion or variant can have an antigen-binding region that comprises at least a portion of at least one light chain CDR (i.e., CDR1, CDR2 and/or CDR3) having the amino acid sequence of the corresponding CDRs 1, 2 and/or 3. In a preferred embodiment the three heavy chain CDRs and the three light chain CDRs of the antibody or antigen-binding fragment have the amino acid sequence of the corresponding CDR of at least one of mAb, as described herein. Such antibodies can be prepared by chemically joining together the various portions (e.g., CDRs, framework) of the antibody using conventional techniques, by preparing and expressing a (i.e., one or more) nucleic acid molecule that encodes the antibody using conventional techniques of recombinant DNA technology or by using any other suitable method.

The anti-Gas6 antibody can comprise at least one of a heavy or light chain variable region having a defined amino acid sequence. Antibodies that bind to human Gas6 and that comprise a defined heavy or light chain variable region can be prepared using suitable methods, such as phage display (Katsube, Y., et al., Int J. Mol. Med, 1(5):863-868 (1998)) or methods that employ transgenic animals, as known in the art and/or as described herein. For example, a transgenic mouse, comprising a functionally rearranged human immunoglobulin heavy chain transgene and a transgene comprising DNA from a human immunoglobulin light chain locus that can undergo functional rearrangement, can be immunized with human Gas6 or a fragment thereof to elicit the production of antibodies. If desired, the antibody producing cells can be isolated and hybridomas or other immortalized antibody-producing cells can be prepared as described herein and/or as known in the art. Alternatively, the antibody, specified portion or variant can be expressed using the encoding nucleic acid or portion thereof in a suitable host cell.

Cloning and Expression of Anti-Gas6 Antibody in Mammalian Cells

A typical mammalian expression vector contains at least one promoter element, which mediates the initiation of transcription of mRNA, the antibody coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRS) from Retroviruses, e.g., GAS-6, HTLVI, HIVI and the early promoter of the cytomegalovirus (CMV). However, cellular elements can also be used (e.g., the human actin promoter). Suitable expression vectors for use in practicing the present invention include, for example, vectors such as pIRES1neo, pRetro-Off, pRetro-On, PLXSN, or pLNCX (Clonetech Labs, Palo Alto, Calif.), pcDNA3.1 (+/−), pcDNA/Zeo (+/−) or pcDNA3.1/Hygro (+/−) (Invitrogen), PSVL and PMSG (Pharmacia, Uppsala, Sweden), pGAS-6cat (ATCC 37152), pSV2dhfr (ATCC 37146) and pBC12MI (ATCC 67109). Mammalian host cells that could be used include human Hela 293, H9 and Jurkat cells, mouse NIH3T3 and C127 cells, Cos 1, Cos 7 and CV 1, quail QC1-3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, or hygromycin allows the identification and isolation of the transfected cells.

The transfected gene can also be amplified to express large amounts of the encoded antibody. The DHFR (dihydrofolate reductase) marker is useful to develop cell lines that carry several hundred or even several thousand copies of the gene of interest. Another useful selection marker is the enzyme glutamine synthase (GS) (Murphy, et al., Biochem. J. 227: 277-279 (1991); Bebbington, et al., Bio/Technology 10:169-175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of antibodies.

The expression vectors pC1 and pC4 contain the strong promoter (LTR) of the Rous Sarcoma Virus (Cullen, et al., Molec. Cell. Biol. 5:438-447 (1985)) plus a fragment of the CMV-enhancer (Boshart, et al., Cell 41:521-530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

Cloning and Expression in CHO Cells

The vector pC4 is used for the expression of anti-Gas6 antibody. Plasmid pC4 is a derivative of the plasmid pSV2-dhfr (ATCC Accession No. 37146). The plasmid contains the mouse DHFR gene under control of the SV40 early promoter. Chinese hamster ovary—or other cells lacking dihydrofolate activity that are transfected with these plasmids can be selected by growing the cells in a selective medium (e.g., alpha minus MEM, Life Technologies, Gaithersburg, Md.)

supplemented with the chemotherapeutic agent methotrexate. The amplification of the DHFR genes in cells resistant to methotrexate (MTX) has been well documented (see, e.g., F. W. Alt, et al., J. Biol. Chem. 253:1357-1370 (1978); J. L. Hamlin and C. Ma, Biochem. et Biophys. Acta 1097:107-143 (1990);

and M. J. Page and M. A. Sydenham, Biotechnology 9:64-68 (1991)). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach can be used to develop cell lines carrying more than 1,000 copies of the amplified gene(s). Subsequently, when the methotrexate is withdrawn, cell lines are obtained that contain the amplified gene integrated into one or more chromosome(s) of the host cell.

Plasmid pC4 contains for expressing the gene of interest the strong promoter of the long terminal repeat (LTR) of the Rous Sarcoma Virus (Cullen, et al., Molec. Cell. Biol. 5:438-447 (1985)) plus a fragment isolated from the enhancer of the immediate early gene of human cytomegalovirus (CMV) (Boshart, et al., Cell 41:521-530 (1985)). Downstream of the promoter are BamHI, XbaI, and Asp718 restriction enzyme cleavage sites that allow integration of the genes. Behind these cloning sites the plasmid contains the 3' intron and polyadenylation site of the rat preproinsulin gene. Other high efficiency promoters can also be used for the expression, e.g., the human b-actin promoter, the SV40 early or late promoters or the long terminal repeats from other retroviruses, e.g., HIV and HTLVI. Clontech's Tet-Off and Tet-On gene expression systems and similar systems can be used to express the Gas6 in a regulated way in mammalian cells (M. Gossen, and H. Bujard, Proc. Natl. Acad. Sci. USA 89: 5547-5551 (1992)). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with restriction enzymes and then dephosphorylated using calf intestinal phosphatase by procedures known in the art. The vector is then isolated from a 1% agarose gel.

The DNA sequence encoding the complete anti-Gas6 antibody is used according to known method steps. Isolated nucleic acid encoding a suitable human constant region (i.e., HC and LC regions) is also used in this construct.

The isolated variable and constant region encoding DNA and the dephosphorylated vector are then ligated with T4 DNA ligase. *E. coli* HB101 or XL-1 Blue cells are then transformed and bacteria are identified that contain the fragment inserted into plasmid pC4 using, for instance, restriction enzyme analysis.

Chinese hamster ovary (CHO) cells lacking an active DHFR gene are used for transfection. 5 μg of the expression plasmid pC4 is cotransfected with 0.5 μg of the plasmid pSV2-neo using lipofectin. The plasmid pSV2neo contains a dominant selectable marker, the neo gene from Tn5 encoding an enzyme that confers resistance to a group of antibiotics including G418. The cells are seeded in alpha minus MEM supplemented with 1 μg/ml G418. After 2 days, the cells are trypsinized and seeded in hybridoma cloning plates (Greiner, Germany) in alpha minus MEM supplemented with 10, 25, or 50 ng/ml of methotrexate plus 1 μg/ml G418. After about 10-14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 mM, 2 mM, 5 mM, 10 mM, 20 mM). The same procedure is repeated until clones are obtained that grow at a concentration of 100-200 mM. Expression of the desired gene product is analyzed, for instance, by SDS-PAGE and Western blot or by reverse phase HPLC analysis.

The invention also relates to antibodies, antigen-binding fragments, immunoglobulin chains and CDRs comprising amino acids in a sequence that is substantially the same as an amino acid sequence described herein. Preferably, such antibodies or antigen-binding fragments and antibodies comprising such chains or CDRs can bind human Gas6 with high affinity (e.g., KD less than or equal to about 10-9 M). Amino acid sequences that are substantially the same as the sequences described herein include sequences comprising conservative amino acid substitutions, as well as amino acid deletions and/or insertions. A conservative amino acid substitution refers to the replacement of a first amino acid by a second amino acid that has chemical and/or physical properties (e.g, charge, structure, polarity, hydrophobicity/hydrophilicity) that are similar to those of the first amino acid. Conservative substitutions include replacement of one amino acid by another within the following groups: lysine (K), arginine (R) and histidine (H); aspartate (D) and glutamate (E); asparagine (N), glutamine (O), serine (S), threonine (T), tyrosine (Y), K, R, H, D and E; alanine (A), valine (V), leucine (L), isoleucine (I), proline (P), phenylalanine (F), tryptophan (W), methionine (M), cysteine (C) and glycine (G); F, W and Y; C, S and T.

G.4. Anti-Idiotype Antibodies to Anti-Gas6 Antibody Compositions

In addition to monoclonal or chimeric anti-Gas6 antibodies, the present invention is also directed to an anti-idiotypic (anti-Id) antibody specific for such antibodies of the invention. An anti-Id antibody is an antibody which recognizes unique determinants generally associated with the antigen-binding region of another antibody. The anti-Id can be prepared by immunizing an animal of the same species and genetic type (e.g. mouse strain) as the source of the Id antibody with the antibody or a CDR containing region thereof. The immunized animal will recognize and respond to the idiotypic determinants of the immunizing antibody and produce an anti-Id antibody. The anti-Id antibody may also be used as an "immunogen" to induce an immune response in yet another animal, producing a so-called anti-anti-Id antibody.

G.5. Anti-Gas6 Antibody Compositions

The present invention also provides at least one anti-Gas6 antibody composition comprising at least one, at least two, at least three, at least four, at least five, at least six or more anti-Gas6 antibodies thereof, as described herein and/or as known in the art that are provided in a non-naturally occurring composition, mixture or form. Such compositions comprise non-naturally occurring compositions comprising at least one or two full length, C- and/or N-terminally deleted variants, domains, fragments, or specified variants, of the anti-Gas6 antibody amino acid sequence selected from the group consisting of 80-100% of the contiguous amino acids of SEQ ID NOS 26 and 28, or specified fragments, domains or variants thereof. Preferred anti-Gas6 antibody compositions include at least one or two full length, fragments, domains or variants as at least one CDR or LBP containing portions of the anti-Gas6 antibody sequence of 80-100% of SEQ ID NOS: 29-34, or specified fragments, domains or variants thereof. Further preferred compositions comprise 40-99% of at least one of 70-100% of SEQ ID NOS: 26 or 28, or specified fragments, domains or variants thereof. Such composition percentages are by weight, volume, concentration, molarity, or morality as liquid or dry solutions, mixtures, suspension, emulsions, particles, powder, or colloids, as known in the art or as described herein.

Anti-Gas6 antibody compositions of the present invention can further comprise at least one of any suitable and effective amount of a composition or pharmaceutical composition comprising at least one anti-Gas6 antibody to a cell, tissue, organ, animal or patient in need of such modulation, treatment or therapy, optionally further comprising at least one selected from at least one TNF antagonist (e.g., but not limited to a TNF antibody or fragment, a soluble TNF receptor or fragment, fusion proteins thereof, or a small molecule TNF antagonist), an antirheumatic (e.g., methotrexate, auranofin, aurothioglucose, azathioprine, etanercept, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anesthetic, a neuromuscular blocker, an antimicrobial (e.g., aminoglycoside, an antifungal, an antiparasitic, an antiviral, a carbapenem, cephalosporin, a flurorquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropieitin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine or a cytokine antagonist. Non-limiting examples of such cytokines include, but are not limited to, any of IL-1 to IL-23. Suitable dosages are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

Such anti-cancer or anti-infectives can also include toxin molecules that are associated, bound, co-formulated or co-administered with at least one antibody of the present invention. The toxin can optionally act to selectively kill the pathologic cell or tissue. The pathologic cell can be a cancer or other cell. Such toxins can be, but are not limited to, purified or recombinant toxin or toxin fragment comprising at least one functional cytotoxic domain of toxin, e.g., selected from at least one of ricin, diphtheria toxin, a venom toxin, or a bacterial toxin. The term toxin also includes both endotoxins and exotoxins produced by any naturally occurring, mutant or recombinant bacteria or viruses which may cause any pathological condition in humans and other mammals, including toxin shock, which can result in death. Such toxins may include, but are not limited to, enterotoxigenic E. coli heat-labile enterotoxin (LT), heat-stable enterotoxin (ST), Shigella cytotoxin, Aeromonas enterotoxins, toxic shock syndrome toxin-1 (TSST-1), Staphylococcal enterotoxin A (SEA), B (SEB), or C (SEC), Streptococcal enterotoxins and the like. Such bacteria include, but are not limited to, strains of a species of enterotoxigenic E. coli (ETEC), enterohemorrhagic E. coli (e.g., strains of serotype 0157:H7), Staphylococcus species (e.g., Staphylococcus aureus, Staphylococcus pyogenes), Shigella species (e.g., Shigella dysenteriae, Shigella flexneri, Shigella boydii, and Shigella sonnei), Salmonella species (e.g., Salmonella typhi, Salmonella cholerasuis, Salmonella enteritidis), Clostridium species (e.g., Clostridium perfringens, Clostridium dificile, Clostridium botulinum), Camphlobacter species (e.g., Camphlobacter jejuni, Camphlobacter fetus), Heliobacter species, (e.g., Heliobacter pylori), Aeromonas species (e.g., Aeromonas sobria, Aeromonas hydrophila, Aeromonas caviae), Pleisomonas shigelloides, Yersina enterocolitica, Vibrios species (e.g., Vibrios cholerae, Vibrios parahemolyticus), Klebsiella species, Pseudomonas aeruginosa, and Streptococci. See, e.g., Stein, ed., INTERNAL MEDICINE, 3rd ed., pp 1-13, Little, Brown and Co., Boston, (1990); Evans et al., eds., Bacterial Infections of Humans: Epidemiology and Control, 2d. Ed., pp 239-254, Plenum Medical Book Co., New York (1991); Mandell et al, Principles and Practice of Infectious Diseases, 3d. Ed., Churchill Livingstone, New York (1990); Berkow et al, eds., The Merck Manual, 16th edition, Merck and Co., Rahway, N.J., 1992; Wood et al, FEMS Microbiology Immunology, 76:121-134 (1991); Marrack et al, Science, 248:705-711 (1990), the contents of which references are incorporated entirely herein by reference.

Anti-Gas6 antibody compounds, compositions or combinations of the present invention can further comprise at least one of any suitable auxiliary, such as, but not limited to, diluent, binder, stabilizer, buffers, salts, lipophilic solvents, preservative, adjuvant or the like. Pharmaceutically acceptable auxiliaries are preferred. Non-limiting examples of, and methods of preparing such sterile solutions are well known in the art, such as, but limited to, Gennaro, Ed., Remington's Pharmaceutical Sciences, 18th Edition, Mack Publishing Co. (Easton, Pa.) 1990.

Pharmaceutically acceptable carriers can be routinely selected that are suitable for the mode of administration, solubility and/or stability of the anti-Gas6 antibody, fragment or variant composition as well known in the art or as described herein. Pharmaceutical excipients and additives useful in the present composition include but are not limited to proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. One preferred amino acid is glycine.

Carbohydrate excipients suitable for use in the invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. Preferred carbohydrate excipients for use in the present invention are mannitol, trehalose, and raffinose.

Anti-Gas6 antibody compositions can also include a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. Preferred buffers for use in the present compositions are organic acid salts such as citrate.

Additionally, anti-Gas6 antibody compositions of the invention can include polymeric excipients/additives such as polyvinylpyrrolidones, ficolls (a polymeric sugar), dextrates (e.g., cyclodextrins, such as 2-hydroxypropyl-$\alpha$-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents (e.g., EDTA).

These and additional known pharmaceutical excipients and/or additives suitable for use in the anti-Gas6 antibody, portion or variant compositions according to the invention are known in the art, e.g., as listed in "Remington: The Science & Practice of Pharmacy", 19th ed., Williams & Williams, (1995), and in the "Physician's Desk Reference", 52nd ed., Medical Economics, Montvale, N.J. (1998), the disclosures of which are entirely incorporated herein by reference. Preferred carrier or excipient materials are carbohydrates (e.g., saccharides and alditols) and buffers (e.g., citrate) or polymeric agents.

H. Antibody Evaluation

Figure 2:
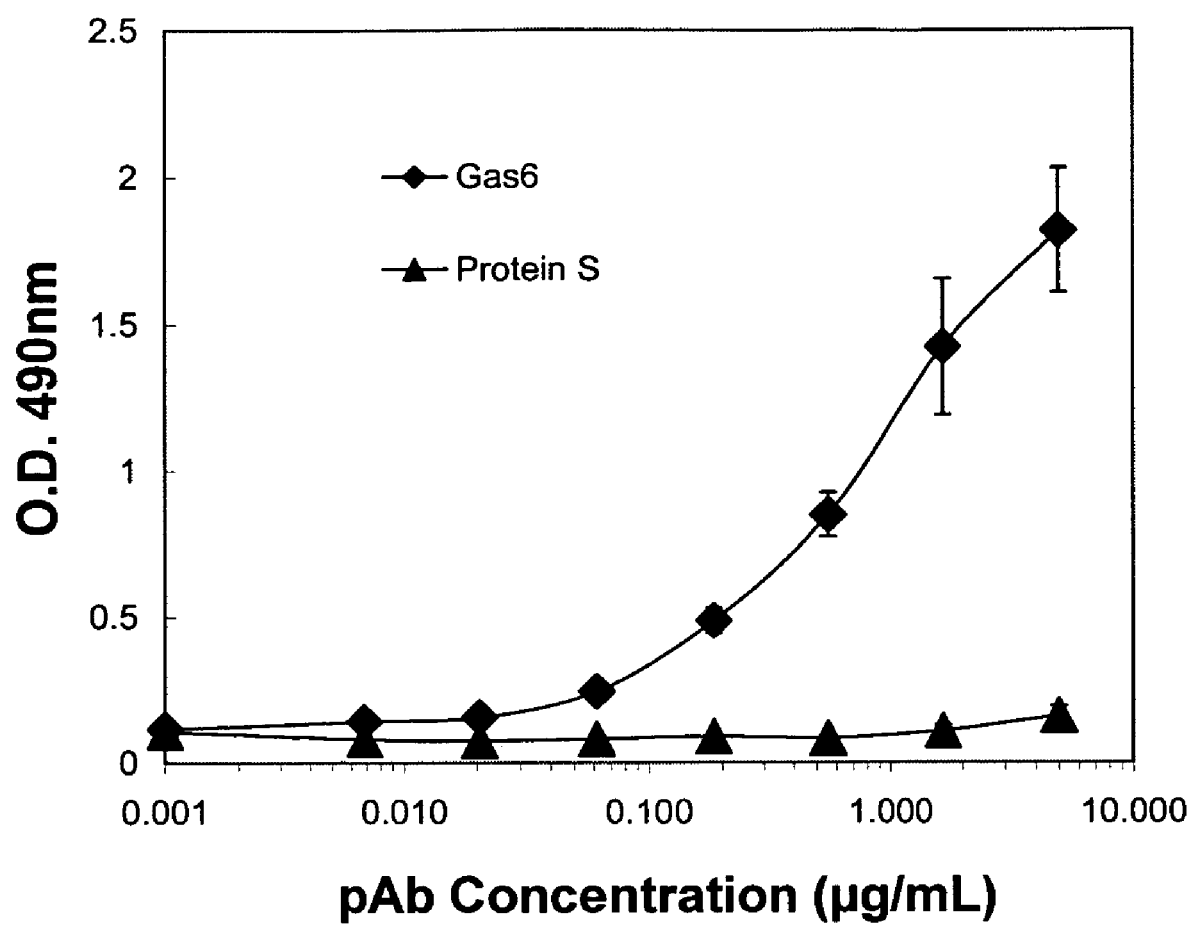
FIG. 2. is a graph showing the binding of a rabbit anti-EST3 IgG to Gas6.

Sera from immunized animals were detected using an EIA. Briefly, 96 well plates coated with 0.5 µg/ml full-length recombinant human Gas6, incubated with a serial dilution of the sera and probed with HRP labeled secondary antibodies. After treatment with substrate solution, the signals at 490 nm were detected using an automated plate spectrometer. Sera or hybridoma supernatants were also simultaneously assayed for cross-reactivity with Protein S. Antibodies that bind to Gas6 selectively are preferred. FIG. 2 shows an example of a rabbit anti-EST3 polyclonal antibody that selectively binds to Gas6.

Antibody reactivity to Gas6 may also be assessed using a RIA. Hybridoma supernatants are incubated on IgG captured plates and probed with $^{125}$I-Gas6, and bound signals were quantified using a gamma counter. Binding characteristics for all antibodies can be measured by a Gas6 capture EIA and BIAcore technology.

Figure 3:
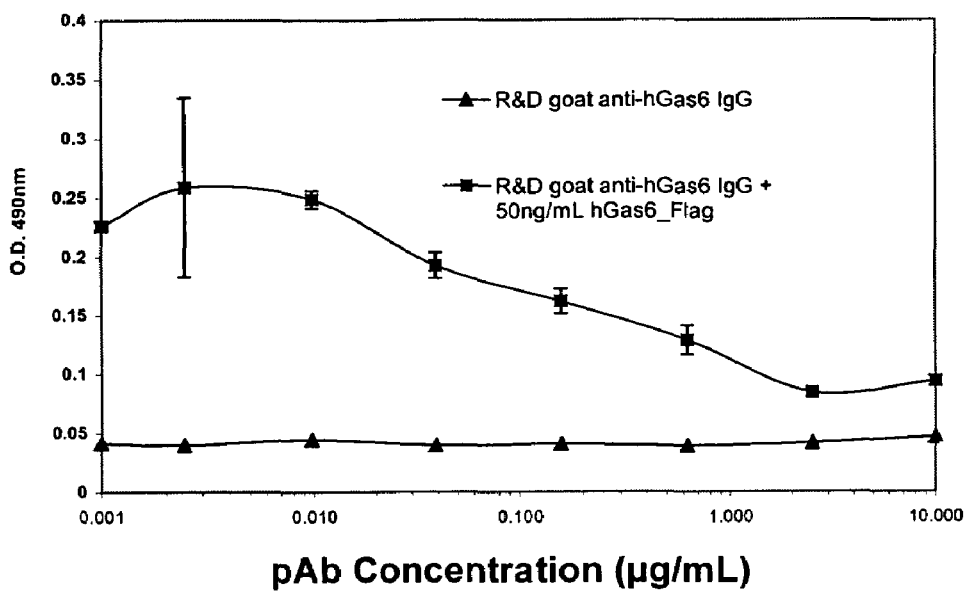
FIG. 3. is a series of graphs showing the ability of a neutralizing anti-Gas6 antibody (goat anti-Gas6 antibody was obtained from R&D Systems) to inhibit binding of Gas6 to Axl-Fc receptor.
Figure 3:
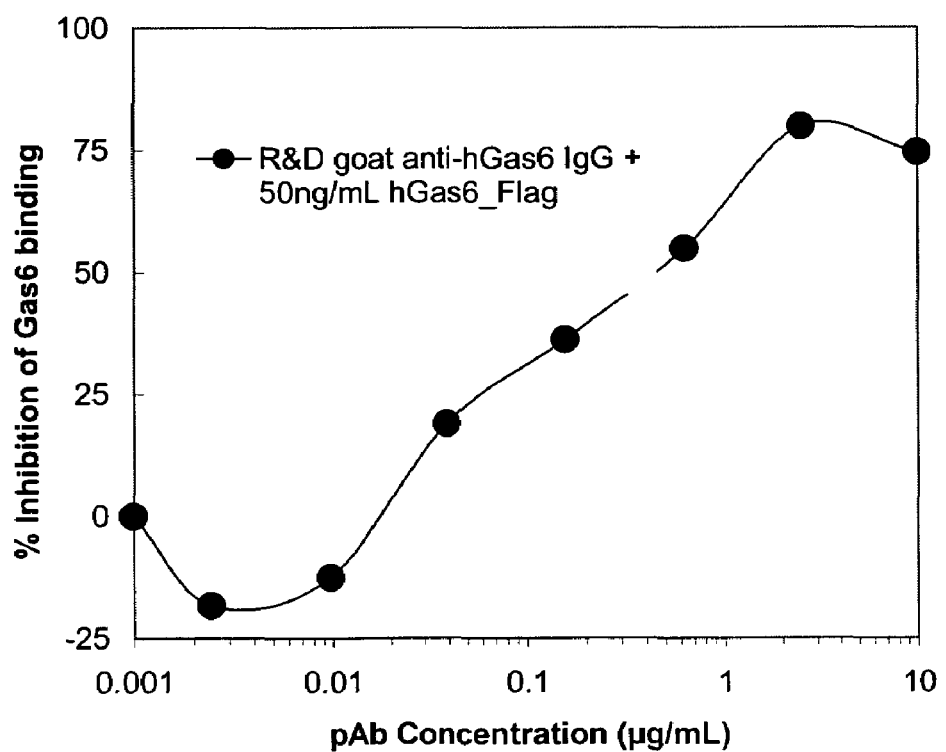

An initial screen for neutralization anti-Gas6 antibodies was based on a receptor binding EIA. Briefly, 96 well plates were coated with receptor or Fc-receptor chimera (R&D System, Minneapolis, Minn.) and incubated with recombinant Gas6 that was pre-treated with a serial dilution of the candidate antagonists. The plates were then probed with an anti-Gas6 detecting antibody (preferably HRP-conjugated). FIG. 3 shows an example of a goat anti-Gas6 polyclonal antibody that inhibits Gas6 binding to Axl receptor.

While Gas6 binding to its receptor (Axl, Mer, or Sky) is routinely used for screening antagonists, the invention is not so limited. Other assays including, but not limited to, Gas6-dependent receptor phosphorylation, receptor internalization, cell proliferation, prevention of cell apoptosis, and induction of signaling molecules or cell markers may be adapted.

I. Applications

The Gas6 antibodies preferably do not cross-react with Protein S. Gas6 selective antibodies may be used for diagnostic assays for Gas6; e.g., detecting its expression in specific cells, tissues, or serum. The antibodies can be labeled and/or immobilized on an insoluble matrix. The antibodies of this invention are also useful for the affinity purification of Gas6 from recombinant cell culture or natural sources.

The present invention also provides a method for modulating or treating at least one Gas6 related disease, in a cell, tissue, organ, animal, or patient, as known in the art or as described herein, using at least one Gas6 antibody of the present invention Compositions of anti-Gas6 antibody or polypeptide antagonist may find therapeutic use in treatment of thromboembolic disease or thrombotic pathologic condition such as ischemic disease (ischemic stroke, ischemic cerebral infarction, acute myocardial infarction, and chronic ischemic heart disease), venous thromboembolism, arterial or venous thrombosis, pulmonary embolism, restenosis following coronary artery bypass surgery or following percutaneous transluminal angioplasty of coronary artery, diabetic angiopathy and allograft arteriosclerosis. Gas6 antagonists should also be beneficial for preventing other disease conditions such as cancer, atherosclerosis, sepsis, glomerular sclerosis, diabetes, rheumatoid arthritis, osteoarthritis, and osteoporosis.

I.1. Detailed Therapeutic Applications

The present invention provides a method for modulating or treating at least one Gas6 related disease, in a cell, tissue, organ, animal, or patient including, but not limited to, at least one of obesity, an immune related disease, a cardiovascular disease, an infectious disease, a malignant disease or a neurologic disease.

The present invention also provides a method for modulating or treating at least one immune related disease, in a cell, tissue, organ, animal, or patient including, but not limited to, at least one of rheumatoid arthritis, juvenile rheumatoid arthritis, systemic onset juvenile rheumatoid arthritis, psoriatic arthritis, ankylosing spondilitis, gastric ulcer, seronegative arthropathies, osteoarthritis, inflammatory bowel disease, ulcerative colitis, systemic lupus erythematosis, antiphospholipid syndrome, iridocyclitis/uveitis/optic neuritis, idiopathic pulmonary fibrosis, systemic vasculitis/wegener's granulomatosis, sarcoidosis, orchitis/vasectomy reversal procedures, allergic/atopic diseases, asthma, allergic rhinitis, eczema, allergic contact dermatitis, allergic conjunctivitis, hypersensitivity pneumonitis, transplants, organ transplant rejection, graft-versus-host disease, systemic inflammatory response syndrome, sepsis syndrome, gram positive sepsis, gram negative sepsis, culture negative sepsis, fungal sepsis, neutropenic fever, urosepsis, meningococcemia, trauma/hemorrhage, burns, ionizing radiation exposure, acute pancreatitis, adult respiratory distress syndrome, rheumatoid arthritis, alcohol-induced hepatitis, chronic inflammatory pathologies, sarcoidosis, Crohn's pathology, sickle cell anemia, diabetes, nephrosis, atopic diseases, hypersensitity reactions, allergic rhinitis, hay fever, perennial rhinitis, conjunctivitis, endometriosis, asthma, urticaria, systemic anaphalaxis, dermatitis, pernicious anemia, hemolytic disease, thrombocytopenia, graft rejection of any organ or tissue, kidney transplant rejection, heart transplant rejection, liver transplant rejection, pancreas transplant rejection, lung transplant rejection, bone marrow transplant (BMT) rejection, skin allograft rejection, cartilage transplant rejection, bone graft rejection, small bowel transplant rejection, fetal thymus implant rejection, parathyroid transplant rejection, xenograft rejection of any organ or tissue, allograft rejection, anti-receptor hypersensitivity reactions, Graves disease, Raynoud's disease, type B insulin-resistant diabetes, asthma, myasthenia gravis, antibody-mediated cytotoxicity, type III hypersensitivity reactions, systemic lupus erythematosus, POEMS syndrome (polyneuropathy, organomegaly, endocrinopathy, monoclonal gammopathy, and skin changes syndrome), polyneuropathy, organomegaly, endocrinopathy, monoclonal gammopathy, skin changes syndrome, antiphospholipid syndrome, pemphigus, scleroderma, mixed connective tissue disease, idiopathic Addison's disease, diabetes mellitus, chronic active hepatitis, primary billiary cirrhosis, vitiligo, vasculitis, post-MI cardiotomy syndrome, type IV hypersensitivity, contact dermatitis, hypersensitivity pneumonitis, allograft rejection, granulomas due to intracellular organisms, drug sensitivity, metabolic/idiopathic, Wilson's disease, hemachromatosis, alpha-1-antitrypsin deficiency, diabetic retinopathy, hashimoto's thyroiditis, osteoporosis, hypothalamic-pituitary-adrenal axis evaluation, primary biliary cirrhosis, thyroiditis, encephalomyelitis, cachexia, cystic fibrosis, neonatal chronic lung disease, chronic obstructive pulmonary disease (COPD), familial hematophagocytic lymphohistiocytosis, dermatologic conditions, psoriasis, alopecia, nephrotic syndrome, nephritis, glomerular nephritis, acute renal failure, hemodialysis, uremia, toxicity, preeclampsia, okt3 therapy, anti-cd3 therapy, cytokine therapy, chemotherapy, radiation therapy (e.g., including but not limited toasthenia, anemia, cachexia, and the like), chronic salicylate intoxication, and the like. See, e.g., the Merck Manual, 12th-17th Editions, Merck & Company, Rahway, N.J. (1972, 1977, 1982, 1987, 1992, 1999), Pharmacotherapy Handbook, Wells et al., eds., Second Edition, Appleton and Lange, Stamford, Conn. (1998, 2000), each entirely incorporated by reference.

The present invention also provides a method for modulating or treating at least one cardiovascular disease in a cell, tissue, organ, animal, or patient, including, but not limited to, at least one of cardiac stun syndrome, myocardial infarction, congestive heart failure, stroke, ischemic stroke, hemorrhage, arteriosclerosis, atherosclerosis, restenosis, diabetic aterio-sclerotic disease, hypertension, arterial hypertension, renovascular hypertension, syncope, shock, syphilis of the cardiovascular system, heart failure, cor pulmonale, primary pulmonary hypertension, cardiac arrhythmias, atrial ectopic beats, atrial flutter, atrial fibrillation (sustained or paroxysmal), post perfusion syndrome, cardiopulmonary bypass inflammation response, chaotic or multifocal atrial tachycardia, regular narrow QRS tachycardia, specific arrythmias, ventricular fibrillation, His bundle arrythmias, atrioventricular block, bundle branch block, myocardial ischemic disorders, coronary artery disease, angina pectoris, myocardial infarction, cardiomyopathy, dilated congestive cardiomyopathy, restrictive cardiomyopathy, valvular heart diseases, endocarditis, pericardial disease, cardiac tumors, aordic and peripheral aneuryisms, aortic dissection, inflammation of the aorta, occulsion of the abdominal aorta and its branches, peripheral vascular disorders, occulsive arterial disorders, peripheral atherlosclerotic disease, thromboangitis obliterans, functional peripheral arterial disorders, Raynaud's phenomenon and disease, acrocyanosis, erythromelalgia, venous diseases, venous thromibosis, varicose veins, arteriovenous fistula, lymphederma, lipedema, unstable angina, reperfusion injury, post pump syndrome, ischemia-reperfusion injury, and the like. Such a method can optionally comprise administering an effective amount of a composition or pharmaceutical composition comprising at least one anti-Gas6 antibody to a cell, tissue, organ, animal or patient in need of such modulation, treatment or therapy.

The present invention also provides a method for modulating or treating at least one infectious disease in a cell, tissue, organ, animal or patient, including, but not limited to, at least one of: acute or chronic bacterial infection, acute and chronic parasitic or infectious processes, including bacterial, viral and fungal infections, HIV infection/HIV neuropathy, meningitis, hepatitis (e.g., A, B or C, or the like), septic arthritis, peritonitis, pneumonia, epiglottitis, *e. coli* 0157:h7, hemolytic uremic syndrome/thrombolytic thrombocytopenic purpura, malaria, dengue hemorrhagic fever, leishmaniasis, leprosy, toxic shock syndrome, streptococcal myositis, gas gangrene, *mycobacterium tuberculosis, mycobacterium avium* intracellulare, *pneumocystis carinii* pneumonia, pelvic inflammatory disease, orchitis/epidydimitis, *legionella*, lyme disease, influenza a, epstein-barr virus, vital-associated hemaphagocytic syndrome, vital encephalitis/aseptic meningitis, and the like;

The present invention also provides a method for modulating or treating at least one malignant disease in a cell, tissue, organ, animal or patient, including, but not limited to, at least one of: leukemia, acute leukemia, acute lymphoblastic leukemia (ALL), B-cell, T-cell or FAB ALL, acute myeloid leukemia (AML), chromic myelocytic leukemia (CML), chronic lymphocytic leukemia (CLL), hairy cell leukemia, myelodyplastic syndrome (MDS), a lymphoma, Hodgkin's disease, a malignamt lymphoma, non-hodgkin's lymphoma, Burkitt's lymphoma, multiple myeloma, Kaposi's sarcoma, colorectal carcinoma, pancreatic carcinoma, nasopharyngeal carcinoma, malignant histiocytosis, paraneoplastic syndrome/hypercalcemia of malignancy, solid tumors, adenocarcinomas, sarcomas, malignant melanoma, hemangioma, metastatic disease, cancer related bone resorption, cancer related bone pain, and the like.

The present invention also provides a method for modulating or treating at least one neurologic disease in a cell, tissue, organ, animal or patient, including, but not limited to, at least one of: neurodegenerative diseases, multiple sclerosis, migraine headache, AIDS dementia complex, demyelinating diseases, such as multiple sclerosis and acute transverse myelitis; extrapyramidal and cerebellar disorders' such as lesions of the corticospinal system; disorders of the basal ganglia or cerebellar disorders; hyperkinetic movement disorders such as Huntington's Chorea and senile chorea; drug-induced movement disorders, such as those induced by drugs which block CNS dopamine receptors; hypokinetic movement disorders, such as Parkinson's disease; Progressive supra-nucleo Palsy; structural lesions of the cerebellum; spinocerebellar degenerations, such as spinal ataxia, Friedreich's ataxia, cerebellar cortical degenerations, multiple systems degenerations (Mencel, Dejerine-Thomas, Shi-Drager, and Machado-Joseph); systemic disorders (Refsum's disease, abetalipoprotemia, ataxia, telangiectasia, and mitochondrial multi.system disorder); demyelinating core disorders, such as multiple sclerosis, acute transverse myelitis; and disorders of the motor unit' such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Dementia of Lewy body type; Wernicke-Korsakoff syndrome; chronic alcoholism; Creutzfeldt-Jakob disease; Subacute sclerosing panencephalitis, Hallerrorden-Spatz disease; and Dementia pugilistica, and the like. Such a method can optionally comprise administering an effective amount of a composition or pharmaceutical composition comprising at least one TNF antibody or specified portion or variant to a cell, tissue, organ, animal or patient in need of such modulation, treatment or therapy. See, e.g., the Merck Manual, 16th Edition, Merck & Company, Rahway, N.J. (1992)

Any method of the present invention can comprise administering an effective amount of a composition or pharmaceutical composition comprising at least one anti-Gas6 antibody to a cell, tissue, organ, animal or patient in need of such modulation, treatment or therapy. Such a method can optionally further comprise co-administration or combination therapy for treating such immune diseases, wherein the administering of said at least one anti-Gas6 antibody, specified portion or variant thereof, further comprises administering, before concurrently, and/or after, at least one selected from at least one TNF antagonist (e.g., but not limited to a TNF antibody or fragment, a soluble TNF receptor or fragment, fusion proteins thereof, or a small molecule TNF antagonist), an antirheumatic (e.g., methotrexate, auranofin, aurothioglucose, azathioprine, etanercept, gold sodium thiomalate, hydroxychloroquine sulfate, leflunomide, sulfasalzine), a muscle relaxant, a narcotic, a non-steroid antiinflammatory drug (NSAID), an analgesic, an anesthetic, a sedative, a local anesthetic, a neuromuscular blocker, an antimicrobial (e.g., aminoglycoside, an antifungal, an antiparasitic, an antiviral, a carbapenem, cephalosporin, a flurorquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropieitin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine or a cytokine antagonist. Suitable dosages are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

J. Formulations

As noted above, the invention provides for stable formulations, which is preferably a phosphate buffer with saline or a chosen salt, as well as preserved solutions and formulations containing a preservative as well as multi-use preserved formulations suitable for pharmaceutical or veterinary use, comprising at least one anti-Gas6 antibody in a pharmaceutically acceptable formulation. Preserved formulations contain at least one known preservative or optionally selected from the group consisting of at least one phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1-2% m-cresol (e.g., 0.2, 0.3. 0.4, 0.5, 0.9, 1.0%), 0.1-3% benzyl alcohol (e.g., 0.5, 0.9, 1.1, 1.5, 1.9, 2.0, 2.5%), 0.001-0.5% thimerosal (e.g., 0.005, 0.01), 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, 1.0%), and the like.

As noted above, the invention provides an article of manufacture, comprising packaging material and at least one vial comprising a solution of at least one anti-Gas6 antibody with the prescribed buffers and/or preservatives, optionally in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater. The invention further comprises an article of manufacture, comprising packaging material, a first vial comprising lyophilized at least one anti-Gas6 antibody, and a second vial comprising an aqueous diluent of prescribed buffer or preservative, wherein said packaging material comprises a label that instructs a patient to reconstitute the at least one anti-Gas6 antibody in the aqueous diluent to form a solution that can be held over a period of twenty-four hours or greater.

The at least one anti-Gas6 antibody used in accordance with the present invention can be produced by recombinant means, including from mammalian cell or transgenic preparations, or can be purified from other biological sources, as described herein or as known in the art.

The range of at least one anti-Gas6 antibody in the product of the present invention includes amounts yielding upon reconstitution, if in a wet/dry system, concentrations from about 1.0 µg/ml to about 1000 mg/ml, although lower and higher concentrations are operable and are dependent on the intended delivery vehicle, e.g., solution formulations will differ from transdermal patch, pulmonary, transmucosal, or osmotic or micro pump methods.

Preferably, the aqueous diluent optionally further comprises a pharmaceutically acceptable preservative. Preferred preservatives include those selected from the group consisting of phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof. The concentration of preservative used in the formulation is a concentration sufficient to yield an anti-microbial effect. Such concentrations are dependent on the preservative selected and are readily determined by the skilled artisan.

Other excipients, e.g. isotonicity agents, buffers, antioxidants, preservative enhancers, can be optionally and preferably added to the diluent. An isotonicity agent, such as glycerin, is commonly used at known concentrations. A physiologically tolerated buffer is preferably added to provide improved pH control. The formulations can cover a wide range of pHs, such as from about pH 4 to about pH 10, and preferred ranges from about pH 5 to about pH 9, and a most preferred range of about 6.0 to about 8.0. Preferably the formulations of the present invention have pH between about 6.8 and about 7.8. Preferred buffers include phosphate buffers, most preferably sodium phosphate, particularly phosphate buffered saline (PBS).

Other additives, such as a pharmaceutically acceptable solubilizers like Tween 20 (polyoxyethylene (20) sorbitan monolaurate), Tween 40 (polyoxyethylene (20) sorbitan monopalmitate), Tween 80 (polyoxyethylene (20) sorbitan monooleate), Pluronic F68 (polyoxyethylene polyoxypropylene block copolymers), and PEG (polyethylene glycol) or non-Ionic surfactants such as polysorbate 20 or 80 or poloxamer 184 or 188, Pluronic® polyls, other block co-polymers, and chelators such as EDTA and EGTA can optionally be added to the formulations or compositions to reduce aggregation. These additives are particularly useful if a pump or plastic container is used to administer the formulation. The presence of pharmaceutically acceptable surfactant mitigates the propensity for the protein to aggregate.

The formulations of the present invention can be prepared by a process which comprises mixing at least one anti-Gas6 antibody and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing the at least one anti-Gas6 antibody and preservative in an aqueous diluent is carried out using conventional dissolution and mixing procedures. To prepare a suitable formulation, for example, a measured amount of at least one anti-Gas6 antibody in buffered solution is combined with the desired preservative in a buffered solution in quantities sufficient to provide the protein and preservative at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed formulations can be provided to patients as clear solutions or as dual vials comprising a vial of lyophilized at least one anti-Gas6 antibody that is reconstituted with a second vial containing water, a preservative and/or excipients, preferably a phosphate buffer and/or saline and a chosen salt, in an aqueous diluent. Either a single solution vial or dual vial requiring reconstitution can be reused multiple times and can suffice for a single or multiple cycles of patient treatment and thus can provide a more convenient treatment regimen than currently available.

The present claimed articles of manufacture are useful for administration over a period of immediately to twenty-four hours or greater. Accordingly, the presently claimed articles of manufacture offer significant advantages to the patient. Formulations of the invention can optionally be safely stored at temperatures of from about 2 to about 40° C. and retain the biologically activity of the protein for extended periods of time, thus, allowing a package label indicating that the solution can be held and/or used over a period of 6, 12, 18, 24, 36, 48, 72, or 96 hours or greater. If preserved diluent is used, such label can include use up to 1-12 months, one-half, one and a half, and/or two years.

The solutions of at least one anti-Gas6 antibody in the invention can be prepared by a process that comprises mixing at least one antibody in an aqueous diluent. Mixing is carried out using conventional dissolution and mixing procedures. To prepare a suitable diluent, for example, a measured amount of at least one antibody in water or buffer is combined in quantities sufficient to provide the protein and optionally a preservative or buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed products can be provided to patients as clear solutions or as dual vials comprising a vial of lyophilized at least one anti-Gas6 antibody that is reconstituted with a second vial containing the aqueous diluent. Either a single solution vial or dual vial requiring reconstitution can be reused multiple times and can suffice for a single or multiple cycles of patient treatment and thus provides a more convenient treatment regimen than currently available.

The claimed products can be provided indirectly to patients by providing to pharmacies, clinics, or other such institutions and facilities, clear solutions or dual vials comprising a vial of lyophilized at least one anti-Gas6 antibody that is reconstituted with a second vial containing the aqueous diluent. The clear solution in this case can be up to one liter or even larger in size, providing a large reservoir from which smaller portions of the at least one antibody solution can be retrieved one or multiple times for transfer into smaller vials and provided by the pharmacy or clinic to their customers and/or patients.

Recognized devices comprising these single vial systems include those pen-injector devices for delivery of a solution such as BD Pens, BD Autojector®, Humaject®, NovoPen®, B-D®Pen®, AutoPen®, and OptiPen®, GenotropinPen®, Genotronorm Pen®, Humatro Pen®, Reco-Pen®, Roferon Pen®, Biojector®, Iject®, J-tip Needle-Free Injectors, Intraject®, Medi-Ject®, e.g., as made or developed by Becton Dickensen (Franklin Lakes, N.J., www.bectondickenson-.com), Disetronic (Burgdorf, Switzerland, www.disetronic-.com; Bioject, Portland, Oreg. (www.bioject.com); National Medical Products, Weston Medical (Peterborough, UK, www.weston-medical.com), Medi-Ject Corp (Minneapolis, Minn., www.mediject.com). Recognized devices comprising a dual vial system include those pen-injector systems for reconstituting a lyophilized drug in a cartridge for delivery of the reconstituted solution such as the HumatroPen®.

The products presently claimed include packaging material. The packaging material provides, in addition to the information required by the regulatory agencies, the conditions under which the product can be used. The packaging material of the present invention provides instructions to the patient to reconstitute the at least one anti-Gas6 antibody in the aqueous diluent to form a solution and to use the solution over a period of 2-24 hours or greater for the two vial, wet/dry, product. For the single vial, solution product, the label indicates that such solution can be used over a period of 2-24 hours or greater. The presently claimed products are useful for human pharmaceutical product use.

The formulations of the present invention can be prepared by a process that comprises mixing at least one anti-Gas6 antibody and a selected buffer, preferably a phosphate buffer containing saline or a chosen salt. Mixing the at least one anti-Gas6 antibody and buffer in an aqueous diluent is carried out using conventional dissolution and mixing procedures. To prepare a suitable formulation, for example, a measured amount of at least one antibody in water or buffer is combined with the desired buffering agent in water in quantities sufficient to provide the protein and buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed stable or preserved formulations can be provided to patients as clear solutions or as dual vials comprising a vial of lyophilized at least one anti-Gas6 antibody that is reconstituted with a second vial containing a preservative or buffer and excipients in an aqueous diluent. Either a single solution vial or dual vial requiring reconstitution can be reused multiple times and can suffice for a single or multiple cycles of patient treatment and thus provides a more convenient treatment regimen than currently available.

Other formulations or methods of stabilizing the anti-Gas6 antibody may result in other than a clear solution of lyophilized powder comprising said antibody. Among non-clear solutions are formulations comprising particulate suspensions, said particulates being a composition containing the anti-Gas6 antibody in a structure of variable dimension and known variously as a microspheres, microparticle, nanoparticle, nanospheres, or liposome. Such relatively homogenous essentially spherical particulate formulations containing an active agent can be formed by contacting an aqueous phase containing the active and a polymer and a nonaqueous phase followed by evaporation of the nonaqueous phase to cause the coalescence of particles from the aqueous phase as taught in U.S. Pat. No. 4,589,330. Porous microparticles can be prepared using a first phase containing active and a polymer dispersed in a continuous solvent and removing said solvent from the suspension by freeze-drying or dilution-extraction-precipitation as taught in U.S. Pat. No. 4,818,542. Preferred polymers for such preparations are natural or synthetic copolymers or polymer selected from the group consisting of gelatin agar, starch, arabinogalactan, albumin, collagen, polyglycolic acid, polylactic aced, glycolide-L(-) lactide poly(episilon-caprolactone, poly(epsilon-caprolactone-CO-lactic acid), poly(epsilon-caprolactone-CO-glycolic acid), poly(B-hydroxy butyric acid), polyethylene oxide, polyethylene, poly(alkyl-2-cyanoacrylate), poly(hydroxyethyl methacrylate), polyamides, poly(amino acids), poly(2-hydroxyethyl DL-aspartamide), poly(ester urea), poly(L-phenylalanine/ethylene glycol/1,6-diisocyanatohexane) and poly(methyl methacrylate). Particularly preferred polymers are polyesters such as polyglycolic acid, polylactic aced, glycolide-L(-) lactide poly(episilon-caprolactone, poly(epsilon-caprolactone-CO-lactic acid), and poly(epsilon-caprolactone-CO-glycolic acid. Solvents useful for dissolving the polymer and/or the active include: water, hexafluoroisopropanol, methylenechloride, tetrahydrofuran, hexane, benzene, or hexafluoroacetone sesquihydrate. The process of dispersing the active containing phase with a second phase may include pressure forcing said first phase through an orifice in a nozzle to affect droplet formation.

Dry powder formulations may result from processes other than lyophilization such as by spray drying or solvent extraction by evaporation or by precipitation of a crystalline composition followed by one or more steps to remove aqueous or nonaqueous solvent. Preparation of a spray-dried antibody preparation is taught in U.S. Pat. No. 6,019,968. The antibody-based dry powder compositions may be produced by spray drying solutions or slurries of the antibody and, optionally, excipients, in a solvent under conditions to provide a respirable dry powder. Solvents may include polar compounds such as water and ethanol, which may be readily dried. Antibody stability may be enhanced by performing the spray drying procedures in the absence of oxygen, such as under a nitrogen blanket or by using nitrogen as the drying gas. Another relatively dry formulation is a dispersion of a plurality of perforated microstructures dispersed in a suspension medium that typically comprises a hydrofluoroalkane propellant as taught in WO 9916419. The stabilized dispersions may be administered to the lung of a patient using a metered dose inhaler. Equipment useful in the commercial manufacture of spray dried medicaments are manufactured by Buchi Ltd. or Niro Corp.

At least one anti-Gas6 antibody in either the stable or preserved formulations or solutions described herein, can be administered to a patient in accordance with the present invention via a variety of delivery methods including SC or IM injection; transdermal, pulmonary, transmucosal, implant, osmotic pump, cartridge, micro pump, or other means appreciated by the skilled artisan, as well-known in the art.

J.1. Alternative Administration

Many known and developed modes of can be used according to the present invention for administering pharmaceutically effective amounts of at least one anti-Gas6 antibody according to the present invention. While pulmonary administration is used in the following description, other modes of administration can be used according to the present invention with suitable results.

Gas6 antibodies of the present invention can be delivered in a carrier, as a solution, emulsion, colloid, or suspension, or as a dry powder, using any of a variety of devices and methods suitable for administration by inhalation or other modes described here within or known in the art.

J.2. Parenteral Formulations and Administration

Formulations for parenteral administration can contain as common excipients sterile water or saline, polyalkylene glycols such as polyethylene glycol, oils of vegetable origin, hydrogenated naphthalenes and the like. Aqueous or oily suspensions for injection can be prepared by using an appropriate emulsifier or humidifier and a suspending agent, according to known methods. Agents for injection can be a non-toxic, non-orally administrable diluting agent such as aquous solution or a sterile injectable solution or suspension in a solvent. As the usable vehicle or solvent, water, Ringer's solution, isotonic saline, etc. are allowed; as an ordinary solvent, or suspending solvent, sterile involatile oil can be used. For these purposes, any kind of involatile oil and fatty acid can be used, including natural or synthetic or semisynthetic fatty oils or fatty acids; natural or synthetic or semisynthetic mono- or di- or tri-glycerides. Parental administration is known in the art and includes, but is not limited to, conventional means of injections, a gas pressured needle-less injection device as described in U.S. Pat. No. 5,851,198, and a laser perforator device as described in U.S. Pat. No. 5,839,446 entirely incorporated herein by reference.

J.3. Alternative Delivery

The invention further relates to the administration of at least one anti-Gas6 antibody by parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal means. At least one anti-Gas6 antibody composition can be prepared for use for parenteral (subcutaneous, intramuscular or intravenous) or any other administration particularly in the form of liquid solutions or suspensions; for use in vaginal or rectal administration particularly in semisolid forms such as, but not limited to, creams and suppositories; for buccal, or sublingual administration such as, but not limited to, in the form of tablets or capsules; or intranasally such as, but not limited to, the form of powders, nasal drops or aerosols or certain agents;

or transdermally such as not limited to a gel, ointment, lotion, suspension or patch delivery system with chemical enhancers such as dimethyl sulfoxide to either modify the skin structure or to increase the drug concentration in the transdermal patch (Junginger, et al. In "Drug Permeation Enhancement"; Hsieh, D. S., Eds., pp. 59-90 (Marcel Dekker, Inc. New York 1994, entirely incorporated herein by reference), or with oxidizing agents that enable the application of formulations containing proteins and peptides onto the skin (WO 98/53847), or applications of electric fields to create transient transport pathways such as electroporation, or to increase the mobility of charged drugs through the skin such as iontophoresis, or application of ultrasound such as sonophoresis (U.S. Pat. Nos. 4,309,989 and 4,767,402) (the above publications and patents being entirely incorporated herein by reference).

J.4. Pulmonary/Nasal Administration

For pulmonary administration, preferably at least one anti-Gas6 antibody composition is delivered in a particle size effective for reaching the lower airways of the lung or sinuses. According to the invention, at least one anti-Gas6 antibody can be delivered by any of a variety of inhalation or nasal devices known in the art for administration of a therapeutic agent by inhalation. These devices capable of depositing aerosolized formulations in the sinus cavity or alveoli of a patient include metered dose inhalers, nebulizers, dry powder generators, sprayers, and the like. Other devices suitable for directing the pulmonary or nasal administration of antibodies are also known in the art. All such devices can use of formulations suitable for the administration for the dispensing of antibody in an aerosol. Such aerosols can be comprised of either solutions (both aqueous and non aqueous) or solid particles. Metered dose inhalers like the Ventolin® metered dose inhaler, typically use a propellent gas and require actuation during inspiration (See, e.g., WO 94/16970, WO 98/35888). Dry powder inhalers like Turbuhaler™ (Astra), Rotahaler® (Glaxo), Diskus® (Glaxo), Spiros™ inhaler (Dura), devices marketed by Inhale Therapeutics, and the Spinhaler® powder inhaler (Fisons), use breath-actuation of a mixed powder (U.S. Pat. No. 4,668,218 Astra, EP 237507 Astra, WO 97/25086 Glaxo, WO 94/08552 Dura, U.S. Pat. No. 5,458,135 Inhale, WO 94/06498 Fisons, entirely incorporated herein by reference). Nebulizers like AERx™ Aradigm, the Ultravent® nebulizer (Mallinckrodt), and the Acorn II® nebulizer (Marquest Medical Products) (U.S. Pat. No. 5,404,871 Aradigm, WO 97/22376), the above references entirely incorporated herein by reference, produce aerosols from solutions, while metered dose inhalers, dry powder inhalers, etc. generate small particle aerosols. These specific examples of commercially available inhalation devices are intended to be a representative of specific devices suitable for the practice of this invention, and are not intended as limiting the scope of the invention. Preferably, a composition comprising at least one anti-Gas6 antibody is delivered by a dry powder inhaler or a sprayer. There are a several desirable features of an inhalation device for administering at least one antibody of the present invention. For example, delivery by the inhalation device is advantageously reliable, reproducible, and accurate. The inhalation device can optionally deliver small dry particles, e.g. less than about 10 µm, preferably about 1-5 µm, for good respirability.

J.5. Administration of Gas6 Antibody Compositions as a Spray

A spray including Gas6 antibody composition can be produced by forcing a suspension or solution of at least one anti-Gas6 antibody through a nozzle under pressure. The nozzle size and configuration, the applied pressure, and the liquid feed rate can be chosen to achieve the desired output and particle size. An electrospray can be produced, for example, by an electric field in connection with a capillary or nozzle feed. Advantageously, particles of at least one anti-Gas6 antibody composition delivered by a sprayer have a particle size less than about 10 µm, preferably in the range of about 1 µm to about 5 µm, and most preferably about 2 µm to about 3 µm.

Formulations of at least one anti-Gas6 antibody composition suitable for use with a sprayer typically include antibody composition in an aqueous solution at a concentration of about 0.1 mg to about 100 mg of at least one anti-Gas6 antibody composition per ml of solution or mg/gm, or any range or value therein, e.g., but not limited to, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/ml or mg/gm. The formulation can include agents such as an excipient, a buffer, an isotonicity agent, a preservative, a surfactant, and, preferably, zinc. The formulation can also include an excipient or agent for stabilization of the antibody composition, such as a buffer, a reducing agent, a bulk protein, or a carbohydrate. Bulk proteins useful in formulating antibody compositions include albumin, protamine, or the like. Typical carbohydrates useful in formulating antibody compositions include sucrose, mannitol, lactose, trehalose, glucose, or the like. The antibody composition formulation can also include a surfactant, which can reduce or prevent surface-induced aggregation of the antibody composition caused by atomization of the solution in forming an aerosol. Various conventional surfactants can be employed, such as polyoxyethylene fatty acid esters and alcohols, and polyoxyethylene sorbitol fatty acid esters. Amounts will generally range between 0.001 and 14% by weight of the formulation. Especially preferred surfactants for purposes of this invention are polyoxyethylene sorbitan monooleate, polysorbate 80, polysorbate 20, or the like. Additional agents known in the art for formulation of a protein such as Gas6 antibodies, or specified portions or variants, can also be included in the formulation.

J.6. Administration of Gas6 Antibody Compositions by a Nebulizer

Antibody composition can be administered by a nebulizer, such as jet nebulizer or an ultrasonic nebulizer. Typically, in a jet nebulizer, a compressed air source is used to create a high-velocity air jet through an orifice. As the gas expands beyond the nozzle, a low-pressure region is created, which draws a solution of antibody composition through a capillary tube connected to a liquid reservoir. The liquid stream from the capillary tube is sheared into unstable filaments and droplets as it exits the tube, creating the aerosol. A range of configurations, flow rates, and baffle types can be employed to achieve the desired performance characteristics from a given jet nebulizer. In an ultrasonic nebulizer, high-frequency electrical energy is used to create vibrational, mechanical energy, typically employing a piezoelectric transducer. This energy is transmitted to the formulation of antibody composition either directly or through a coupling fluid, creating an aerosol including the antibody composition. Advantageously, particles of antibody composition delivered by a nebulizer have a particle size less than about 10 µm, preferably in the range of about 1 µm to about 5 µm, and most preferably about 2 µm to about 3 µm.

Formulations of at least one anti-Gas6 antibody suitable for use with a nebulizer, either jet or ultrasonic, typically include a concentration of about 0.1 mg to about 100 mg of at least one anti-Gas6 antibody protein per ml of solution. The formulation can include agents such as an excipient, a buffer, an isotonicity agent, a preservative, a surfactant, and, preferably, zinc. The formulation can also include an excipient or agent for stabilization of the at least one anti-Gas6 antibody composition, such as a buffer, a reducing agent, a bulk protein, or a carbohydrate. Bulk proteins useful in formulating at least one anti-Gas6 antibody compositions include albumin, protamine, or the like. Typical carbohydrates useful in formulating at least one anti-Gas6 antibody include sucrose, mannitol, lactose, trehalose, glucose, or the like. The at least one anti-Gas6 antibody formulation can also include a surfactant, which can reduce or prevent surface-induced aggregation of the at least one anti-Gas6 antibody caused by atomization of the solution in forming an aerosol. Various conventional surfactants can be employed, such as polyoxyethylene fatty acid esters and alcohols, and polyoxyethylene sorbital fatty acid esters. Amounts will generally range between 0.001 and 4% by weight of the formulation. Especially preferred surfactants for purposes of this invention are polyoxyethylene sorbitan mono-oleate, polysorbate 80, polysorbate 20, or the like. Additional agents known in the art for formulation of a protein such as antibody protein can also be included in the formulation.

J.7. Administration of Gas6 Antibody Compositions by a Metered Dose Inhaler

In a metered dose inhaler (MDI), a propellant, at least one anti-Gas6 antibody, and any excipients or other additives are contained in a canister as a mixture including a liquefied compressed gas. Actuation of the metering valve releases the mixture as an aerosol, preferably containing particles in the size range of less than about 10 μm, preferably about 1 μm to about 5 μm, and most preferably about 2 μm to about 3 μm. The desired aerosol particle size can be obtained by employing a formulation of antibody composition produced by various methods known to those of skill in the art, including jet-milling, spray drying, critical point condensation, or the like. Preferred metered dose inhalers include those manufactured by 3M or Glaxo and employing a hydrofluorocarbon propellant.

Formulations of at least one anti-Gas6 antibody for use with a metered-dose inhaler device will generally include a finely divided powder containing at least one anti-Gas6 antibody as a suspension in a non-aqueous medium, for example, suspended in a propellant with the aid of a surfactant. The propellant can be any conventional material employed for this purpose, such as chlorofluorocarbon, a hydrochlorofluorocarbon, a hydrofluorocarbon, or a hydrocarbon, including trichlorofluoromethane, dichlorodifluoromethane, dichlorotetrafluoroethanol and 1,1,1,2-tetrafluoroethane, HFA-134a (hydrofluroalkane-134a), HFA-227 (hydrofluroalkane-227), or the like.

Preferably the propellant is a hydrofluorocarbon. The surfactant can be chosen to stabilize the at least one anti-Gas6 antibody as a suspension in the propellant, to protect the active agent against chemical degradation, and the like. Suitable surfactants include sorbitan trioleate, soya lecithin, oleic acid, or the like. In some cases solution aerosols are preferred using solvents such as ethanol. Additional agents known in the art for formulation of a protein such as protein can also be included in the formulation.

One of ordinary skill in the art will recognize that the methods of the current invention can be achieved by pulmonary administration of at least one anti-Gas6 antibody compositions via devices not described herein.

J.8. Oral Formulations and Administration

Formulations for oral rely on the co-administration of adjuvants (e.g., resorcinols and nonionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. Formulations for delivery of hydrophilic agents including proteins and antibodies and a combination of at least two surfactants intended for oral, buccal, mucosal, nasal, pulmonary, vaginal transmembrane, or rectal administration are taught in U.S. Pat. No. 6,309,663. The active constituent compound of the solid-type dosage form for oral administration can be mixed with at least one additive, including sucrose, lactose, cellulose, mannitol, trehalose, raffinose, maltitol, dextran, starches, agar, arginates, chitins, chitosans, pectins, gum tragacanth, gum arabic, gelatin, collagen, casein, albumin, synthetic or semisynthetic polymer, and glyceride. These dosage forms can also contain other type(s) of additives, e.g., inactive diluting agent, lubricant such as magnesium stearate, paraben, preserving agent such as sorbic acid, ascorbic acid, alpha.-tocopherol, antioxidant such as cysteine, disintegrator, binder, thickener, buffering agent, sweetening agent, flavoring agent, perfuming agent, etc.

Tablets and pills can be further processed into enteric-coated preparations. The liquid preparations for oral administration include emulsion, syrup, elixir, suspension and solution preparations allowable for medical use. These preparations can contain inactive diluting agents ordinarily used in said field, e.g., water. Liposomes have also been described as drug delivery systems for insulin and heparin (U.S. Pat. No. 4,239,754). More recently, microspheres of artificial polymers of mixed amino acids (proteinoids) have been used to deliver pharmaceuticals (U.S. Pat. No. 4,925,673). Furthermore, carrier compounds described in U.S. Pat. No. 5,879,681 and U.S. Pat. No. 5,871,753 are used to deliver biologically active agents orally are known in the art.

J.9. Mucosal Formulations and Administration

A formulation for orally administering a bioactive agent encapsulated in one or more biocompatible polymer or copolymer excipients, preferably a biodegradable polymer or copolymer, affording microcapsules which due to the proper size of the resultant microcapsules results in the agent reaching and being taken up by the folliculi lymphatic aggregati, otherwise known as the “Peyer's patch,” or “GALT” of the animal without loss of effectiveness due to the agent having passed through the gastrointestinal tract. Similar folliculi lymphatic aggregati can be found in the bronchei tubes (BALT) and the large intestine. The above-described tissues are referred to in general as mucosally associated lymphoreticular tissues (MALT). For absorption through mucosal surfaces, compositions and methods of administering at least one anti-Gas6 antibody include an emulsion comprising a plurality of submicron particles, a mucoadhesive macromolecule, a bioactive peptide, and an aqueous continuous phase, which promotes absorption through mucosal surfaces by achieving mucoadhesion of the emulsion particles (U.S. Pat. No. 5,514,670). Mucous surfaces suitable for application of the emulsions of the present invention can include corneal, conjunctival, buccal, sublingual, nasal, vaginal, pulmonary, stomachic, intestinal, and rectal routes of administration. Formulations for vaginal or rectal administration, e.g. suppositories, can contain as excipients, for example, polyalkyleneglycols, vaseline, cocoa butter, and the like. Formulations for intranasal administration can be solid and contain as excipients, for example, lactose or can be aqueous or oily solutions of nasal drops. For buccal administration excipients include sugars, calcium stearate, magnesium stearate, pregelinatined starch, and the like (U.S. Pat. No. 5,849,695).

J.10. Transdermal Formulations and Administration

For transdermal administration, the at least one anti-Gas6 antibody is encapsulated in a delivery device such as a liposome or polymeric nanoparticles, microparticle, microcapsule, or microspheres (referred to collectively as microparticles unless otherwise stated). A number of suitable devices are known, including microparticles made of synthetic polymers such as polyhydroxy acids such as polylactic acid, polyglycolic acid and copolymers thereof, polyorthoesters, polyanhydrides, and polyphosphazenes, and natural polymers such as collagen, polyamino acids, albumin and other proteins, alginate and other polysaccharides, and combinations thereof (U.S. Pat. Nos. 5,814,599).

J.11. Prolonged Administration and Formulations

It can be sometimes desirable to deliver the compounds of the present invention to the subject over prolonged periods of time, for example, for periods of one week to one year from a single administration. Various slow release, depot or implant dosage forms can be utilized. For example, a dosage form can contain a pharmaceutically acceptable non-toxic salt of the compounds that has a low degree of solubility in body fluids, for example, (a) an acid addition salt with a polybasic acid such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation such as zinc, calcium, bismuth, barium, magnesium, aluminum, copper, cobalt, nickel, cadmium and the like, or with an organic cation formed from e.g., N,N'-dibenzyl-ethylenediamine or ethylenediamine; or (c) combinations of (a) and (b) e.g. a zinc tannate salt.

Additionally, the compounds of the present invention or, preferably, a relatively insoluble salt such as those just described, can be formulated in a gel, for example, an aluminum monostearate gel with, e.g. sesame oil, suitable for injection. Particularly preferred salts are zinc salts, zinc tannate salts, pamoate salts, and the like. Another type of slow release depot formulation for injection would contain the compound or salt dispersed for encapsulated in a slow degrading, non-toxic, non-antigenic polymer such as a polylactic acid/polyglycolic acid polymer for example as described in U.S. Pat. No. 3,773,919. The compounds or, preferably, relatively insoluble salts such as those described above can also be formulated in cholesterol matrix silastic pellets, particularly for use in animals. Additional slow release, depot or implant formulations, e.g. gas or liquid liposomes are known in the literature (U.S. Pat. No. 5,770,222 and "Sustained and Controlled Release Drug Delivery Systems", J. R. Robinson ed., Marcel Dekker, Inc., N.Y., 1978).

K. Therapeutic Treatments

Any method of the present invention can comprise a method for treating a Gas6 mediated disorder, comprising administering an effective amount of a composition or pharmaceutical composition comprising at least one anti-Gas6 antibody to a cell, tissue, organ, animal or patient in need of such modulation, treatment or therapy. Such a method can optionally further comprise co-administration or combination therapy for treating such immune diseases, wherein the administering of said at least one anti-Gas6 antibody, specified portion or variant thereof, further comprises administering, before concurrently, and/or after, at least one selected from at least one at least one selected from at least one TNF antagonist (e.g., but not limited to a TNF antibody or fragment, a soluble TNF receptor or fragment, fusion proteins thereof, or a small molecule TNF antagonist), an antirheumatic (e.g., methotrexate, auranofin, aurothioglucose, azathioprine, etanercept, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anesthetic, a neuromuscular blocker, an antimicrobial (e.g., aminoglycoside, an antifungal, an antiparasitic, an antiviral, a carbapenem, cephalosporin, a flurorquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropieitin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine or a cytokine antagonist.

Typically, treatment of pathologic conditions is effected by administering an effective amount or dosage of at least one anti-Gas6 antibody composition that total, on average, a range from at least about 0.01 to 500 milligrams of at least one anti-Gas6 antibody per kilogram of patient per dose, and preferably from at least about 0.1 to 100 milligrams antibody/kilogram of patient per single or multiple administration, depending upon the specific activity of contained in the composition. Alternatively, the effective serum concentration can comprise 0.1-5000 µg/ml serum concentration per single or multiple administration. Suitable dosages are known to medical practitioners and will, of course, depend upon the particular disease state, specific activity of the composition being administered, and the particular patient undergoing treatment. In some instances, to achieve the desired therapeutic amount, it can be necessary to provide for repeated administration, i.e., repeated individual administrations of a particular monitored or metered dose, where the individual administrations are repeated until the desired daily dose or effect is achieved.

Preferred doses can optionally include 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100-500 mg/kg/administration, or any range, value or fraction thereof, or to achieve a serum concentration of 0.1, 0.5, 0.9, 1.0, 1.1, 1.2, 1.5, 1.9, 2.0, 2.5, 2.9, 3.0, 3.5, 3.9, 4.0, 4.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 20, 12.5, 12.9, 13.0, 13.5, 13.9, 14.0, 14.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 12, 12.5, 12.9, 13.0, 13.5, 13.9, 14, 14.5, 15, 15.5, 15.9, 16, 16.5, 16.9, 17, 17.5, 17.9, 18, 18.5, 18.9, 19, 19.5, 19.9, 20, 20.5, 20.9, 21, 22, 23, 24, 25, 26, 27, 28, 29, 30, 35, 40, 45, 50, 55, 60, 65, 70, 75, 80, 85, 90, 96, 100, 200, 300, 400, 500, 600, 700, 800, 900, 1000, 1500, 2000, 2500, 3000, 3500, 4000, 4500, and/or 5000 µg/ml serum concentration per single or multiple administration, or any range, value or fraction thereof.

Alternatively, the dosage administered can vary depending upon known factors, such as the pharmacodynamic characteristics of the particular agent, and its mode and route of administration;

age, health, and weight of the recipient; nature and extent of symptoms, kind of concurrent treatment, frequency of treatment, and the effect desired. Usually a dosage of active ingredient can be about 0.1 to 100 milligrams per kilogram of body weight. Ordinarily 0.1 to 50, and preferably 0.1 to 10 milligrams per kilogram per administration or in sustained release form is effective to obtain desired results.

As a non-limiting example, treatment of humans or animals can be provided as a one-time or periodic dosage of at least one antibody of the present invention 0.1 to 100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively or additionally, at least one of week 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, or alternatively or additionally, at least one of 1, 2, 3, 4, 5, 6, 7, 8, 9, 10, 11, 12, 13, 14, 15, 16, 17, 18, 19, or 20 years, or any combination thereof, using single, infusion or repeated doses.

Dosage forms (composition) suitable for internal administration generally contain from about 0.1 milligram to about 500 milligrams of active ingredient per unit or container. In these pharmaceutical compositions the active ingredient will ordinarily be present in an amount of about 0.5-99.999% by weight based on the total weight of the composition.

For parenteral administration, the antibody can be formulated as a solution, suspension, emulsion, particle, powder, or lyophilized powder in association, or separately provided, with a pharmaceutically acceptable parenteral vehicle. Examples of such vehicles are water, saline, Ringer's solution, dextrose solution, and 1-10% human serum albumin. Liposomes and nonaqueous vehicles such as fixed oils can also be used. The vehicle or lyophilized powder can contain additives that maintain isotonicity (e.g., sodium chloride, mannitol) and chemical stability (e.g., buffers and preservatives). The formulation is sterilized by known or suitable techniques.

Suitable pharmaceutical carriers are described in the most recent edition of Remington's Pharmaceutical Sciences, A. Osol, a standard reference text in this field.

EXAMPLES OF INVENTION

Having generally described the invention, the same will be more readily understood by reference to the following examples, which are provided by way of illustration and are not intended as limiting.

It will be clear that the invention can be practiced otherwise than as particularly described in the foregoing description and examples.

Numerous modifications and variations of the present invention are possible in light of the above teachings and, therefore, are within the scope of the appended claims.

Example 1

Preparation of a Molecular Model of Gas6 G Domain

In the present invention, a homology model of the G domain of Gas6 was constructed based on the crystal structure of the laminin alpha 2 chain [61] found in the Protein Data Bank [62] as 1DYK. To prepare the model, ICM-Pro from Molsoft was employed. The alignment used for the construction of the model encompasses residues 280-672 of human Gas6 NCBI record NP_000811 which includes the G domains:

```
Gas6a  ILPCVPFSVAKSVKSLYLGRM---FSGTPVIRLRFKRLQ-PTRLVAEFDFRTFDPEGILLF
1DYK   HGPCV----AESEPALLTGSKQFGLSRNSHIAIAFDDTKVKNRLTIELEVRTEAESGLLFY

AGGHQDSTWIVLALRAGRLELQLRYN-GVGRVTSSGPV-INHGMWQTISVEELARNLVIKV
       MARINHADFATVQLRNG-FPY-FSYDLGSGDTSTMIPTKINDGQWHKIKIVRVKQEGILYV

NRDAVMKIA-VAGDLFQPERGLYHLNLTVGGIPF-HEKDLVQPINPRLDGCMRSWNWLNGE
       DDASSQTISPKKADILDVVGILY-----VGGLPINYTTRRIGPVTYSLDGCVRNLH-MEQA

DTTIQETVKVNTRMQCFSVTERGSFYPGSGFAFYSLDYMRTPLDVGTESTWEVEVVAHIRP
       PVDLDQPTSSFHVGTCFANAESGTYFDGTGFA-KAVGGFKVGLDLLVEFEFRTT-----RP

AADTGVLFALWAPDLRAVPLSVALVD----YHSTKKLKKQLVVLAVEHTALALMEIKVCDG
       ---TGVLLGVSSQKMDG--MGIEMIDEKLMFHVDNGAGRFTAIYDAEIPG------HMCNG

QEHVVTVSLRDGEATLEVDGTRGQSEVSAAQLQERLAVLERHLRSPVLT--FAGGLPDVPV
       QWHKVTAKKIKNRLELVVDGNQVDAQSPNS------ASTSADTNDPVFVGGFPGGLNQFGL

TSAPVTAFYRGCM-TLEVNR---RLLDLD-EAAYKHSDITAHSCPP
       TT---NIRFRGCIRSLKLTKGTGKPLEVNFAKALELRGVQPVSCPT
```

Based on location and liphophilicity, amino acid sequences from the G domain of Gas6 that may be involved in the binding or that could be used to raise antibodies against Gas6 were identified.

These sequences are provided in Table 2.

TABLE 2

| Peptide | SEQ ID NO. | Location | Sequence |
|---|---|---|---|
| 1 | 2 | Gas6(284-298) | VPFSVAKSVKSLYLG |
| 2 | 3 | Gas6(309-323) | LRFKRLQPTRLVAEF |
| 3 | 4 | Gas6(393-410) | IKVNRDAVMKIAVAGDLF |
| 4 | 5 | Gas6(400-415) | VMKIAVAGDLFQPERG |
| 5 | 6 | Gas6(483-497) | SGFAFYSLDYMRTPL |
| 6 | 7 | Gas6(492-503) | YMRTPLDVGTES |
| 7 | 8 | Gas6(521-535) | VLFALWAPDLRAVPL |
| 8 | 9 | Gas6(585-597) | EATLEVDGTRGQS |
| 9 | 10 | Gas6(598-615) | EVSAAQLQERLAVLERHL |

TABLE 2-continued

| Peptide | SEQ ID NO. | Location | Sequence |
|---|---|---|---|
| 10 | 11 | Gas6(614-629) | LRSPVLTFAGGLPDV |
| 11 | 12 | Gas6(629-642) | HVPVTSAPVTAFYRG |
| 12 | 13 | Gas6(646-666) | LEVNRRLLDLDEAAYKHSDIT |
| 13 | 14 | Gas6(639-658) | FYRGCMTLEVNRRLLDLDEA |
| 14 | 15 | Gas6(659-678) | AYKHSDITAHSCPPVEPAAA |

Peptides from the Gas6 G domain were synthesized so that they could be used in the identification and/or generation of anti-Gas6 antibodies.

Using standard Boc or FMOC chemistry, the peptide sequences defined in Table 3 were synthesized. An N-terminal N-acetyl-cysteine was added to all peptides except the last two to allow conjugation to carriers and the C-terminal amino acid was amidated. To avoid conjugation through internal cysteine in the last two peptides, an N-terminal lysine was added to peptide 13 and the internal lysine in peptide 14 was used to allow conjugation to carrier.

TABLE 3

| PEPTIDE FROM TABLE 2 | COMPOSITION PREPARED SYNTHETICALLY | RELATION TO HUMAN GAS6 |
|---|---|---|
| 1 | Ac-CVPFSVAKSVKSLYLG-$NH_2$ | N-acetyl-Cys-Gas6(284-298) amide |
| 2 | Ac-CLRFKRLQPTRLVAEF-$NH_2$ | N-acetyl-Cys-Gas6(309-323) amide |
| 3 | Ac-CIKVNRDAVMKIAVAGDLF-$NH_2$ | N-acetyl-Cys-Gas6(400-415) amide |
| 4 | Ac-CVMKIAVAGDLFQPERG-$NH_2$ | N-acetyl-Cys-Gas6(400-415) amide |
| 5 | Ac-CSGFAFYSLDYMRTPL-$NH_2$ | N-acetyl-Cys-Gas6(483-497) amide |
| 6 | Ac-CYMRTPLDVGTES-$NH_2$ | N-acetyl-Cys-Gas6(492-503) amide |
| 7 | Ac-CVLFALWAPDLRAVPL-$NH_2$ | N-acetyl-Cys-Gas6(521-535) amide |
| 8 | Ac-CEATLEVDGTRGQS-$NH_2$ | N-acetyl-Cys-Gas6(585-597) amide |
| 9 | Ac-CEVSAAQLQERLAVLERHL-$NH_2$ | N-acetyl-Cys-Gas6(598-615) amide |
| 10 | Ac-CHLRSPVLTFAGGLPDV-$NH_2$ | N-acetyl-Cys-Gas6(614-629) amide |
| 11 | Ac-CVPVTSAPVTAFYRG-$NH_2$ | N-acetyl-Cys-Gas6(629-642) amide |
| 12 | Ac-CLEVNRRLLDLDEAAYKHSDIT-$NH_2$ | N-acetyl-Cys-Gas6(646-666) amide |
| 13 | [H]-KFYRGCMTLEVNRRLLDLDEA-[OH] | [H]-Lys-Gas6(639-658)-[OH] |
| 14 | [H]-AYKHSDITAHSCPPVEPAAA-[OH] | [H]-Gas6(659-678)-[OH] |

Example 2

Isolation of DNA Encoding Gas6 Polypeptides and Expression in Bacterial Cells The present invention further identified three "ESTs" or derivatives of Gas6 that encompass regions predicted to contribute to receptor binding or that can be used to raise antibodies that inhibit Gas6 activity. The sequences are listed in Table 4.

Nucleic acid sequence of human Gas6 (SEQ ID NO. 1) was cloned by RT-PCR amplification of RNA samples from CHFR cell line. DNA sequences encoding the three ESTs were subsequently RCA amplified using oligonucleotide primers 5'BamHI-CCAAGATACTTAGACTGCATCAA3' (5'BamHI-SEQ ID NO: 19) and 5'EcoRI-CCTCT-TGAAGCGCAGTCGGA3'(5'EcoRI-SEQ ID NO: 20) for EST1 (SEQ ID NO. 16), oligonucleotide primers 5'BamHI-CCAGGCTGGTAGCTGAGTTTG3' (5'BamHI-SEQ ID NO: 21) and 5'EcoRI-TCCGTTCAGCCAGTTCCAGCT3' (5'EcoRI-SEQ ID NO: 22) for EST2 (SEQ ID NO. 17), and oligonucleotide primers 5'BamHI-ATCCGCCCAGCCGCA-GACA3' (5'BamHI-SEQ ID NO: 23) and 5'EcoRI-CAGTGT-CATGCAGCCGCGGT3' (5'EcoRI-SEQ ID NO: 24) for EST3 (SEQ ID NO. 18). The PCR products were cloned in-frame into the BamHI-EcoRI site of pRSET expression vector (Invitrogen Life Technologies, Carlsbad, Calif.).

TABLE 4

| EST | SEQ ID NO. | SEQUENCE |
|---|---|---|
| EST 1 Gas6 90-316 | 16 | P RYLDCINKYG SPYTKNSGFA TCVQNLPDQC TPNPCDRKGT QACQDLMGNF FCLCKAGWGG RLCDKDVNEC SQENGGCLQI CHNKPGSFHC SCHSGFELSS DGRTCQDIDE CADSEACGEA RCKNLPGSYS CLCDEGFAYS SQEKACRDVD ECLQGRCEQV CVNSPGSYTC HCDGRGGLKL SQDMDTCEDI LPCVPFSVAK SVKSLYLGRM FSGTPVIRLR FKRLQP |
| EST 2 Gas6 317-451 | 17 | TRLV AEFDFRTFDP EGILLFAGGH QDSTWIVLAL RAGRLELQLR YNGVGRVTSS GPVINHGMWQ TISVEELARN LVIKVNRDAV MKIAVAGDLF QPERGLYHLN LTVGGIPFHE KDLVQPINPR LDGCMRSWNW L |
| EST3 Gas6 503-646 | 18 | STWEVEVV AHIRPAADTG VLFALWAPDL RAVPLSVALV DYHSTKKLKK QLVVLAVEHT ALALMEIKVC DGQEHVVTVS LRDGEATLEV DGTRGQSEVS AAQLQERLAV LERHLRSPVL TFAGGLPDVP VTSAPVTAFY RGCMTL |

The three Gas6 ESTs were produced by bacteria transformed with a pRSET vector containing EST nucleic acid under the control of an IPTG inducible promoter. The N-terminus of EST was ligated in-frame with a poly-histidine tag (His-tag) to facilitate purification. Briefly, bacteria cell line BL21(DE3)pLysS was transformed with the expression vector and treated with IPTG. Maximum expression of ESTs was achieved at 3-4 hours after IPTG induction (FIG. 1). The cells were harvested, lysed, and the protein of interest was affinity purified according to the instruction manual for the ProBond Purification System (Invitrogen Life Technologies, Carlsbad, Calif.). Eluted proteins were desalted and the sequences were confirmed by tryptic peptide mapping.

Example 3

Generation and Characterization of Polyclonal Antibodies

Polyclonal antibodies of this invention were raised in animals by multiple subcutaneous (sc) or intraperitoneal (ip) injections of Gas6 peptides or polypeptides and an adjuvant according to established conventional protocols. The peptide antigens were used directly or conjugated to a carrier protein, KLH (keyhole limpet hemocyanin), prior to the injection. Other carrier proteins such as serum albumin, bovine thyroglobulin, or soybean trypsin inhibitor that are immunogenic in the species to be immunized may also be used. Animals were boosted until the titer plateaued.

The initial screen for neutralizing anti-Gas6 antibodies used binding the rhGas6 in a EIA format. A second criteria for selection of an antibody is preferential binding to Gas6 relative to the structurally related but functionally apposing Protein S. The ability of purified IgG to bind to full length Gas6 or a structural related molecule protein S is tested by an EIA. Briefly, a 96 well plate was coated with 0.5 μg/ml Gas6 or Protein S, blocked with 1% BSA, incubated with either serial diluted serum from injected animals or purified rabbit anti-EST IgG and followed by an HRP-conjugated secondary antibody and HRP substrate and readout was $OD_{490}$ (N=3). The reactivity of sera to a full length Gas6 recombinant protein is listed in Table 5.

TABLE 5

| Antigen | Host | Binding to Gas6 |
|---|---|---|
| EST1 | mouse | + |
| EST2 | mouse | ND |
| EST3 | Mouse, rabbit | + |
| Peptide 1 | mouse | + |
| Peptide 1 + 9 | mouse | + |
| Peptide 2* | ND | ND |
| Peptide 2 + 3 | mouse | + |
| Peptide 4 | mouse | ND |
| Peptide 5* | ND | ND |
| Peptide 6 | mouse | + |
| Peptide 7* | ND | ND |
| Peptide 8 | mouse | ND |
| Peptide 9 | mouse | ND |
| Peptide 11 | mouse | + |
| Peptide 11 + 12 | mouse | + |
| Peptide 13 | Rabbit | + |
| Peptide 14 | Rabbit | + |

Note:
*is insoluble.
ND indicates not done.

Serum from a rabbit immunized with EST3 was purified by a protein A column and the ability of purified IgG to bind to full length Gas6 or a structural related molecule protein S was tested by an EIA as shown in FIG. 2. A 96 well plate was coated with 0.5 μg/ml Gas6 or Protein S, blocked with 1% BSA, incubated with rabbit anti-EST3 IgG and probed with a HRP-conjugated secondary antibody. The signals at OD490 following treatment with substrate were shown. N=3

A further test for a neutralizing antibody is based in competitive inhibition of Gas6 for its receptor. The ability of the antibody to inhibit binding of Gas6 to Axl-Fc receptor was tested by an EIA. A 96 well plate was coated with 0.5 microgm/ml Axl-Fc (R&D Systems), blocked with 1% BSA and incubated with the antibody alone or antibody plus 50 ng/ml recombinant Gas6. The plate was probed with an HRP-conjugated secondary antibody followed by substrate treatment and OD$_{490}$ was determined.

FIG. 3 shows an example of a goat anti-Gas6 polyclonal antibody that inhibits Gas6 binding to Axl receptor. A. Dose-dependent inhibition of Gas6 binding is shown. B. Percent inhibition of binding by the rabbit anti-EST3 IgG is shown (N=3).

While Gas6 binding to its receptor (Axl, Mer or Sky) is routinely used for screening antagonists, the invention is not so limited. Other assays including, but not limited to, Gas6-dependent receptor phosphorylation, receptor internalization, cell proliferation, prevention of cell apoptosis, and induction of signaling molecules or cell markers may be adapted.

Example 4

Generation of a Monoclonal Antibody

Recombinant human Gas6 (SEQ ID NO: 1) produced by the method of Example 2 was used to generate a human antibody in mice that express human immunoglobulins but not mouse IgM or Igκ (Lonberg, et al. supra). A female mouse was obtained from Medarex (Foster City, Calif.), and received a total of eight twice-weekly 20 µg injections of recombinant human Gas6 given intradermally (ID) in two hind footpads in Titermax Gold adjuvant (Accurate) for injections 1 and 6 and mixed with 100 µg Inject alum solution (Pierce) for all other injections. Antibody titers were screened from blood collected by retroorbital puncture. A Gas6 solid phase EIA assay was performed to assess serum titers for anti-Gas6 IgG.

For the generation of the monoclonal antibody of the invention, isolated lymphocytes from immunized mice were used in the cell fusion procedure. The immune B cells were isolated and fused with murine myeloma cells utilizing PEG$_{3000}$. The fusion was carried out at a 1:1 ratio of FO murine myeloma cells to viable lymphocytes according to the method of De St. Groth [67]. Briefly, lymphocyte and myeloma cells were mixed together, pelleted and washed twice in PBS. The pellet was resuspended with fusing solution at 37° C. over 1 minute. The cell/fusion mixture was then immersed in a 37° C. water bath for approximately 90 seconds with gentle agitation. The fusion reaction was stopped by adding 37° C. PBS. The fused cells were then centrifuged at 150×G for 5 minutes. The cells were resuspended in HAT medium and then plated 96-well flat bottom polystyrene tissue culture plates. The fusion plates were then placed in a humidified 37° C. incubator containing 5% CO$_2$ and left undisturbed for 7-10 days.

One antibody reactive to human Gas6 was identified but was unstable in cell culture. The parental hybridoma cells were subjected to Ig gene rescue. Cloning of the variable regions to salvage the antibody-encoding sequence may be necessary if the hybridoma is not stable in culture. Briefly, the method employed to clone the variable regions involved isolation of RNA from the hybridoma, followed by PCR amplification, TOPO cloning into an expression vector, and expression of the DNA in E. coli. The hybridoma cells were collected by centrifugation. Trizol reagent (GIBCOBRL, Cat. No 15596) was used to lyze the cells (1 ml per 5×10$^6$ cells). The homogenized lysates were incubated for 5 minutes at room temperature and chloroform was added to the lysates (0.2 mL per 1 mL of TRIZOL reagent). The samples were vortexed, followed by centrifugation for 5 minutes at 4° C. The aqueous phase was transferred to a fresh tube, and the RNA was precipitated from the aqueous phase by mixing with 0.5 mL of isopropyl alcohol per 1 mL of TRIZOL Reagent used for the initial homogeniziation. The mixture was kept at room temperature for 10 minutes and centrifuged for 10 minutes at 4° C. The RNA pellet was washed with 75% ethanol and air dried at room temperature for 5 min. The RNA was dissolved in 7 ul of depc H$_2$O.

Use GeneRacer Method to Amplify Variable Regions

After RNA was purified, a GeneRacer kit from Invitrogen was used to amplify the variable regions, based on the manufacturer's protocol. The GeneRacer 5' Primer was used along with either the HuK-A Primer for the light chain (SEQ ID NO: 35), or the G1-CH2 Long 3' Primer for the Heavy chain. The light chain PCR product was a strong single band around 700 bp. The Heavy chain PCR didn't yield any product. The nested PCR was performed to identify the real product. The GeneRacer nested 5' Primer and the HG1-5B long nested 3' primer (SEQ ID NO: 36) were used to amplify the heavy chain. The heavy chain nested PCR product was a strong single band around 1000 bp. A TOPO TA Cloning Kit was used to clone both HC and LC PCR products into the PCR 4-TOPO vector. The standard TOPO cloning protocol from Invitrogen was followed using One Shot chemically competent E. coli. The LB/Amp plates showed many positive colonies. The DNA was isolated from these clones using a Qiagen Mini-prep spin kit. After mini-prep, the HC and LC PCR fragments were analyzed by sequencing. The sequencing primers were M13 forward and reverse primers.

PCR Cycling Parameters:

| Heavy Chain | |
|---|---|
| 94° C. 2 min | |
| 94° C. 30 sec | |
| 68° C. 30 sec | ] 30 cycles |
| 72° C. 2 min | |
| 72° C. 5 min | |

| Light Chain | |
|---|---|
| 94° C. 2 min | |
| 94° C. 30 sec | |
| 50° C. 30 sec | ] 2 cycles |
| 72° C. 2 min | |
| 94° C. 30 sec | |
| 60° C. 30 sec | ] 28 cycles |
| 72° C. 2 min | |
| 72° C. 5 min | |

Example 5

Cloning of the Human MAB Variable Regions into Expression Vectors

Cloning of the HC variable regions into the CMV human IgG1 expression vector P1836 and the LC variable regions into the CMV human Kappa expression vector P644.

After the HC and LC sequences were obtained, the 5' and 3' primers that include restriction sites were designed to amplify the LC and HC V-regions from the first Gas 6 positive hybridoma cell cDNA. The HC variable region was cloned into the CMV human IgG1 expression vector P1836, by digesting the vector and the HC PCR fragment with BstB1 and Bsiw1 enzymes. The LC variable region was cloned into CMV human Kappa expression vector P644 by digesting the vector and the LC PCR fragment with Hind3 and Sal1 enzymes. After the two correct HC and LC constructs were made and both sequences were confirmed, a large amount of DNA was prepared using a Qiagen HiSpeed plasmid Maxi kit.

These expression constructs were introduced into 293E cells by transient transfection (in 2 of T-150 flasks). 7.5 ug of each HC and LC DNA with 90 ul of lipofectaime 2000 was used for each transfection. The Serum free medium (293SFM2) was replaced after 24 hours.

The expressed vectors were then introduced into 293E cells by transient or stable transfection. The human anti-hGas6 MAB was designated WG1.

The nucleic acid sequences of the heavy chain variable region (SEQ ID NO: 25) and light chain variable region (SEQ ID NO: 27) were conceptually translated and the CDRs identified by multiple alignment analysis of a human antibody database. The heavy chain variable amino acid sequence is given in SEQ ID NO: 26 and the heavy chain CDRs are located as shown below and as SEQ ID NOs: 29-31 for HC CDR1, HC CDR2, and HC CDR3, respectively:

MEFGLTWVFLVALLRGVQCQVQLVESGGGVVQPGRSLRLSCAASGFTFSS

YGMHWVRQAPGKGLEWVAVIWYDGSNKYYADSVKGRFTISRDNSKNTLYL

QXNSLRAEDTAMYFCAREGFYYDILTAYSLEYFQHWGQGTLVTVSS$_{146}$

The light chain variable region amino acid sequence is given in SEQ ID NO: 28 and the heavy chain CDRs are located as shown below and as SEQ ID NOs: 32-34 for LC CDR1, LC CDR2, and LC CDR3, respectively:

MSPSQLIGFLLLWVPASRGEIVLTQSPDFQSVTPKEKVTITCRASQSIGS

SLHWYQQKPDQSPKLLIKYASQSFSGVPSRFSGSGSGTDFTLTINSLEAE

DAAAYYCHQSSSLPYTFGQGTKLEIK$_{126}$

Example 6

Characterization of Human Anti-Gas6 Monoclonal Antibody

Figure 4:
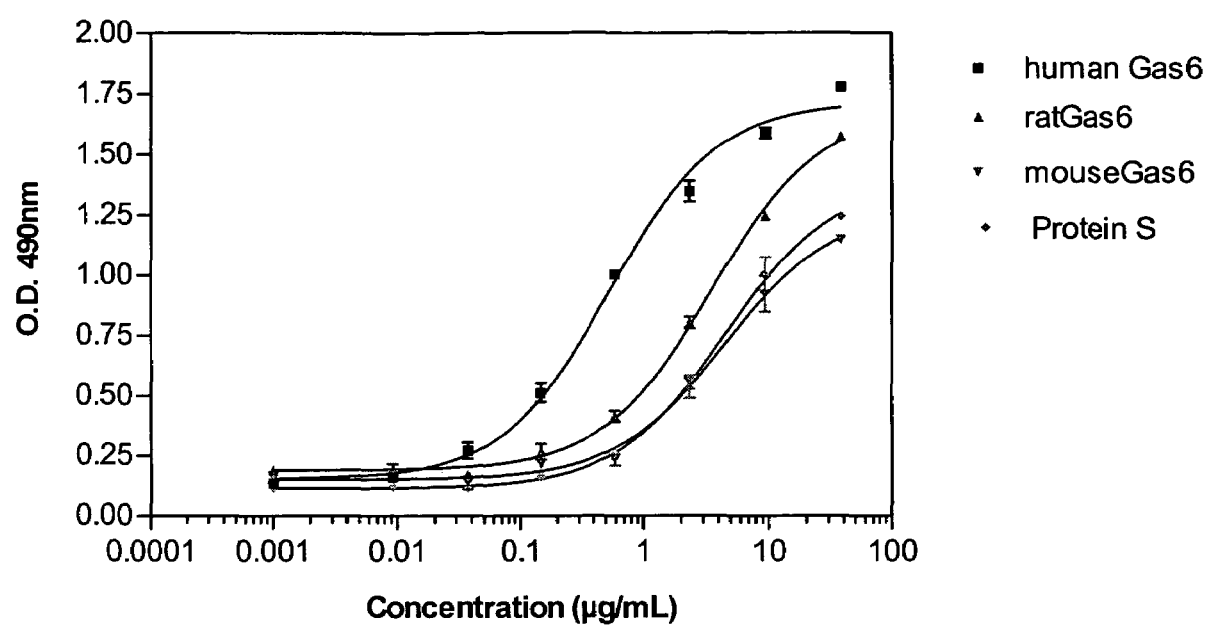
FIG. 4 is a graph showing the concentration related binding of human MAB WG1 to Gas6 from various species; human, rat, and mouse and to human Protein S.

The specificity of the MAB WG1 was confirmed using an EIA: a 96 well plate was coated with 1 µg/mL gas6 (human, rat, or mouse) or protein S overnight. The following day, the plate was washed in a saline solution and blocked with SuperBlock (Pierce). Decreasing dilutions of the antibody WG1 were then added in individual wells at 1:4 dilutions. Goat anti-human Fc-HRP (Sigma) was used as the secondary and detecting reagent. The data, plotted in FIG. 4, show that WG1 antibody binds more potentently to human Gas6 than rat Gas6 or mouse Gas6. WG1 also demonstrates more potent binding to human Gas6 than to human protein S.

Figure 5:
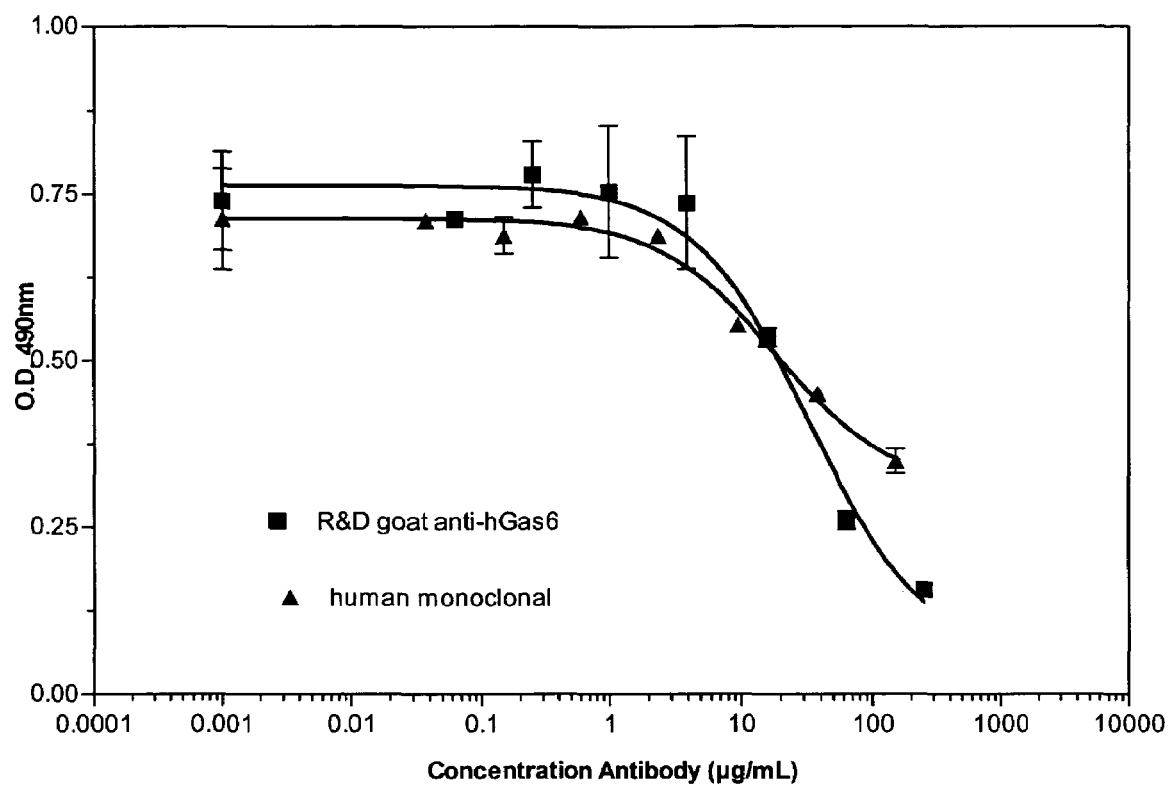
FIG. 5. is a graph showing the concentration dependence of a commercial polyclonal anti-hGas6 antibody (R&S Systems) ability to inhibit rhGas6 to an Axl-Fc chimera in an EIA format compared to that of human MAB WG1.

FIG. 5 shows the neutralization of Gas6 binding to Axl-Fc by the MAB WG1 as described in Example 3. WG1 shows similar potency to the known neutralizing polyclonal preparation commercially available from R & D Systems (goat anti-hGas6).

Epitope mapping of anti-Gas6 antibodies can be performed using mass spectrometry analysis. Recombinant Gas6 protein is mixed and incubated with the antibodies generated at 4° C. overnight. The antigen/antibody complex can then be transferred into digestion buffer and digested with trypsin at 37° C. After complete digestion, the complex is captured by protein G beads. MALDI-TOP mass spectrum analysis can then be used to determine major peaks and peptide sequence identification can be performed by LC-tandem mass spectrometry.

A 1:1 mixture of recombinant Gas6 protein and MAB WG1 was incubated overnight at 4° C. The antibody-protein complex was trypsin-digested, eluted and desalted by ZipTip C18 and spotted on MALDI-TOF chip. Spectra were obtained at laser intensity 1650 and acquisition mass range 850-5000 Da. Major mass peaks were confirmed by LC-MS/MS (service provided by ProtTech, Inc).

Figure 6:
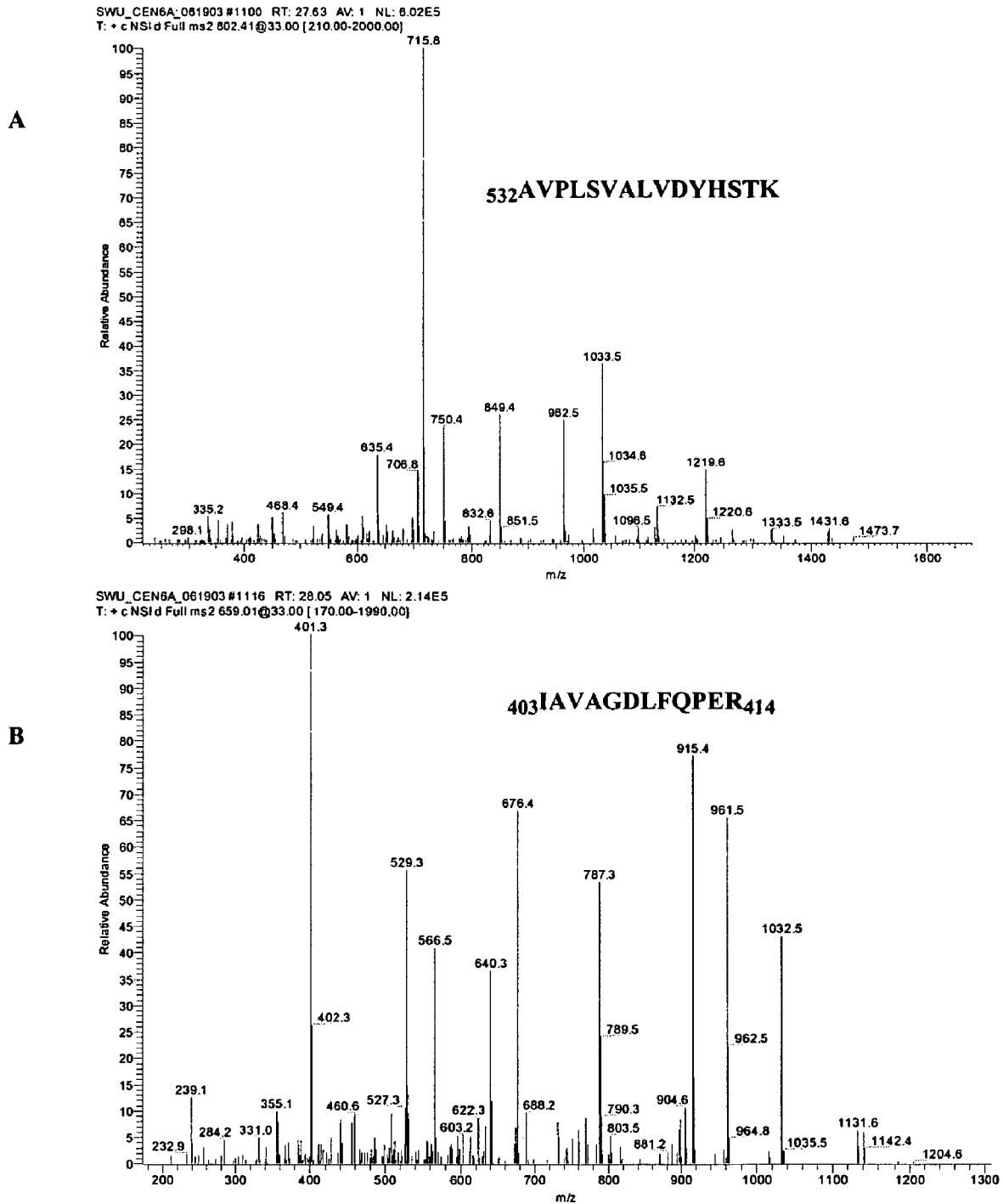
FIG. 6. The MS/MS spectra of the two Gas6 peptides bound by MAB WG1. A. m/z=1599, AVPLSVALVDYHSTK (SEQ ID NO:38)and B. m/z=1315, IAVAGDLFQPER (SEQ ID NO:37).

Table 6 shows the peptides identified as tryptic fragments bound by WG1 using LC-tandem MS. Two peptides were identified as bound by the human monoclonal antibody. FIG. 6 shows the mass spectrometry data for the two peptides identified. Both fragments matched contiguous amino acids in the record >gi|28373340|pdb|H30|A Chain A, C-Terminal Lg Domain Pair Of Human Gas6.

TABLE 6

| SEQUENCE | CAL MS | SEQUENCE IDENTIFICATION |
|---|---|---|
| IAVAGDLFQPER | 1314.69 | Gas6 (403-414) SEQ ID NO:37 |
| AVPLSVALVDYHSTK | 1598.87 | Gas6 (532-545) SEQ ID NO:38 |

The peptide fragments identified in this manner confirm that MAB WG1 binds to the G-domain of Gas6 and to the some or all of the residues contained in peptides identified by the method given in Example 1 and designated Peptides 4 (SEQ ID NO: 5) and 7 (SEQ ID NO: 8).

REFERENCES

1. Schneider, C., R. M. King, and L. Philipson, *Genes specifically expressed at growth arrest of mammalian cells.* Cell, 1988. 54: p. 787-793.
2. Manfioletti, G., et al., *The protein encoded by a growth arrest-specific gene (gas6) is a new member of the vitamin K-dependent proteins related to protein S, a negative coregulator in the blood coagulation cascade.* Mol Cell Biol, 1993. 13(8): p. 4976-85.
3. Joseph, D. R., *Sequence and functional relationships between androgen-binding protein/sex hormone-binding globulin and its homologs protein S, Gas6, laminin, and agrin.* Steroids, 1997. 62(8-9): p. 578-88.
4. Stitt, T. N., et al., *The anticoagulation factor protein S and its relative, Gas6, are ligands for the Tyro 3/Axl family of receptor tyrosine kinases.* Cell, 1995. 80(4): p. 661-70.
5. Varnum, B. C., et al., *Axl receptor tyrosine kinase stimulated by the vitamin K-dependent protein encoded by growth-arrest-specific gene 6.* Nature, 1995. 373(6515): p. 623-6.
6. Nagata, K., et al., *Identification of the product of growth arrest-specific gene 6 as a common ligand for Axl, Sky, and Mer receptor tyrosine kinases.* J Biol Chem, 1996. 271 (47): p. 30022-7.
7. Godowski, P. J., et al., *Reevaluation of the roles of protein S and Gas6 as ligands for the receptor tyrosine kinase Rse/Tyro 3.* Cell, 1995. 82(3): p. 355-8.
8. Ohashi, K., et al., *Stimulation of sky receptor tyrosine kinase by the product of growth arrest-specific gene 6.* J Biol Chem, 1995. 270(39): p. 22681-4.
9. Nakano, T., et al., *Requirement of gamma-carboxyglutamic acid residues for the biological activity of Gas6: contribution of endogenous Gas6 to the proliferation of vascular smooth muscle cells.* Biochem J, 1997. 323(Pt 2): p. 387-92.

10. Tanabe, K., et al., *Roles of gamma-carboxylation and a sex hormone-binding globulin-like domain in receptor-binding and in biological activities of Gas6*. FEBS Lett, 1997. 408(3): p. 306-10.
11. Mark, M. R., et al., *Characterization of Gas6, a member of the superfamily of G domain-containing proteins, as a ligand for Rse and Axl*. J Biol Chem, 1996. 271(16): p. 9785-9.
12. Goruppi, S., et al., *The product of a gas6 splice variant allows the release of the domain responsible for Axl tyrosine kinase receptor activation*. FEBS Lett, 1997. 415 (1): p. 59-63.
13. Nakano, T., et al., *Cell adhesion to phosphatidylserine mediated by a product of growth arrest-specific gene 6*. J Biol Chem, 1997. 272(47): p. 29411-4.
14. Dormady, S. P., X. M. Zhang, and R. S. Basch, *Hematopoietic progenitor cells grow on 3T3 fibroblast monolayers that overexpress growth arrest-specific gene-6 (GAS6)*. Proc Natl Acad Sci USA, 2000. 97(22): p. 12260-5.
15. Prieto, A. L., et al., *Gas6, a ligand for the receptor protein-tyrosine kinase Tyro-3, is widely expressed in the central nervous system*. Brain Res, 1999. 816(2): p. 646-61.
16. Ishimoto, Y. and T. Nakano, *Release of a product of growth arrest-specific gene 6 from rat platelets*. FEBS Lett, 2000. 466(1): p. 197-9.
17. Angelillo-Scherrer, A., et al., *Deficiency or inhibition of Gas6 causes platelet dysfunction and protects mice against thrombosis*. Nat Med, 2001. 7(2): p. 215-21.
18. O'Donnell, K., et al., *Expression of receptor tyrosine kinase Axl and its ligand Gas6 in rheumatoid arthritis: evidence for a novel endothelial cell survival pathway*. Am J Pathol, 1999. 154(4): p. 1171-80.
19. Melaragno, M. G., et al., *Increased expression of Axl tyrosine kinase after vascular injury and regulation by G protein-coupled receptor agonists in rats*. Circ Res, 1998. 83(7): p. 697-704.
20. Carmeliet, P. and A. Luttun, *Genetic studies on the role of proteinases and growth factors in atherosclerosis and aneurysm formation*. Annals of the New York Acad. of Sci., 2001. 947: p. 124-133.
21. Neubauer, A., et al., *Expression of axl, a transforming receptor tyrosine kinase, in normal and malignant hematopoiesis*. Blood, 1994. 84(6): p. 1931-41.
22. Neubauer, A., et al., *Recent progress on the role of Axl, a receptor tyrosine kinase, in malignant transformation of myeloid leukemias*. Leuk Lymphoma, 1997. 25(1-2): p. 91-6.
23. Dirks, W., et al., *Expression of the growth arrest-specific gene 6 (GAS6) in leukemia and lymphoma cell lines*. Leuk Res, 1999. 23(7): p. 643-51.
24. Graham, D. K., et al., *Cloning and mRNA expression analysis of a novel human protooncogene, c-mer*. Cell Growth Differ, 1994. 5(6): p. 647-57.
25. Graham, D. K., et al., *Cloning and developmental expression analysis of the murine c-mer tyrosine kinase*. Oncogene, 1995. 10(12): p. 2349-59.
26. Mark, M. R., et al., *rse, a novel receptor-type tyrosine kinase with homology to Axl/Ufo, is expressed at high levels in the brain*. J Biol Chem, 1994. 269(14): p. 10720-8.
27. Lu, Q. and G. Lemke, *Homeostatic regulation of the immune system by receptor tyrosine kinases of the Tyro 3 family*. Science, 2001. 293(5528): p. 306-11.
28. Li, R., et al., *Identification of Gas6 as a growth factor for human Schwann cells*. J Neurosci, 1996. 16(6): p. 2012-9.
29. Goruppi, S., E. Ruaro, and C. Schneider, *Gas6, the ligand of Axl tyrosine kinase receptor, has mitogenic and survival activities for serum starved NIH3T3 fibroblasts*. Oncogene, 1996. 12(3): p. 471-80.
30. Goruppi, S., et al., *Gas6 induces growth, beta-catenin stabilization, and T-cell factor transcriptional activation in contact-inhibited C57 mammary cells*. Mol Cell Biol, 2001. 21(3): p. 902-15.
31. Yanagita, M., et al., *Gas6 regulates mesangial cell proliferation through Axl in experimental glomerulonephritis*. Am J Pathol, 2001. 158(4): p. 1423-32.
32. Yin, J. L., et al., *Expression of growth arrest-specific gene 6 and its receptors in a rat model of chronic renal transplant rejection*. Transplantation, 2002. 73(4): p. 657-60.
33. Allen, M. P., et al., *Novel mechanism for gonadotropin-releasing hormone neuronal migration involving Gas6/Ark signaling to p38 mitogen-activated protein kinase*. Mol Cell Biol, 2002. 22(2): p. 599-613.
34. Goruppi, S., et al., *Requirement of phosphatidylinositol 3-kinase-dependent pathway and Src for Gas6-Axl mitogenic and survival activities in NIH3T3 fibroblasts*. Mol Cell Biol, 1997. 17(8): p. 4442-53.
35. Goruppi, S., et al., *Gas6-mediated survival in NIH3T3 cells activates stress signalling cascade and is independent of Ras*. Oncogene, 1999. 18(29): p. 4224-36.
36. Lee, W. P., et al., *Axl-gas6 interaction counteracts E1A-mediated cell growth suppression and proapoptotic activity*. Mol Cell Biol, 1999. 19(12): p. 8075-82.
37. Lee, W. P., et al., *Akt is required for Axl-Gas6 signaling to protect cells from E1A-mediated apoptosis*. Oncogene, 2002. 21(3): p. 329-36.
38. Allen, M. P., et al., *Growth arrest-specific gene 6 (Gas6)/adhesion related kinase (Ark) signaling promotes gonadotropin-releasing hormone neuronal survival via extracellular signal-regulated kinase (ERK) and Akt*. Mol Endocrinol, 1999. 13(2): p. 191-201.
39. Funakoshi, H., et al., *Identification of Gas6, a putative ligand for Sky and Axl receptor tyrosine kinases, as a novel neurotrophic factor for hippocampal neurons*. J Neurosci Res, 2002. 68(2): p. 150-60.
40. O'Bryan, J. P., et al., *axl, a transforming gene isolated from primary human myeloid leukemia cells, encodes a novel receptor tyrosine kinase*. Mol Cell Biol, 1991. 11(10): p. 5016-31.
41. Craven, R. J., et al., *Receptor tyrosine kinases expressed in metastatic colon cancer*. Int J Cancer, 1995. 60(6): p. 791-7.
42. Wimmel, A., et al., *Axl receptor tyrosine kinase expression in human lung cancer cell lines correlates with cellular adhesion*. Eur J Cancer, 2001. 37(17): p. 2264-74.
43. Crosier, P. S., et al., *Identification of a novel receptor tyrosine kinase expressed in acute myeloid leukemic blasts*. Leuk Lymphoma, 1995. 18(5-6): p. 443-9.
44. Taylor, I. C., et al., *Mouse mammary tumors express elevated levels of RNA encoding the murine homology of SKY, a putative receptor tyrosine kinase*. J Biol Chem, 1995. 270(12): p. 6872-80.
45. Lai, C., M. Gore, and G. Lemke, *Structure, expression, and activity of tyro 3, a neural adhesion-related receptor tyrosine kinase*. Oncogene, 1994. 9: p. 2567-2578.
46. Ling, L. and H. J. Kung, *Mitogenic signals and transforming potential of Nyk, a newly identified neural cell adhesion molecule-related receptor tyrosine kinase*. Mol Cell Biol, 1995. 15(12): p. 6582-92.
47. Zhan, F., et al., *Comparison of multiple myeloma and chronic lymphocytic leukemia identifies novel patterns of gene expression*. Blood, 2001. 98: p. 368a-369a.

48. Lu, Q., et al., *Tyro-3 family receptors are essential regulators of mammalian spermatogenesis.* Nature, 1999. 398 (6729): p. 723-8.
49. Nandrot, E., et al., *Homozygous deletion in the coding sequence of the c-mer gene in RCS rats unravels general mechanisms of physiological cell adhesion and apoptosis.* Neurobiol Dis, 2000. 7(6 Pt B): p. 586-99.
50. Hall, M. O., et al., *Outer segment phagocytosis by cultured retinal pigment epithelial cells requires Gas6.* Exp Eye Res, 2001. 73(4): p. 509-20.
51. Scott, R. S., et al., *Phagocytosis and clearance of apoptotic cells is mediated by MER.* Nature, 2001. 411(6834): p. 207-11.
52. Avanzi, G. C., et al., *GAS6, the ligand of Axl and Rse receptors, is expressed in hematopoietic tissue but lacks mitogenic activity.* Exp Hematol, 1997. 25(12): p. 1219-26.
53. Compernolle, V., et al., *Abnormal erythropoiesis in mice deficient in Gas6.* Blood, 2001. 98: p. 65a-66a.
54. Nakano, T., et al., *Vascular smooth muscle cell-derived, Gla-containing growth-potentiating factor for Ca(2+)-mobilizing growth factors.* J Biol Chem, 1995. 270(11): p. 5702-5.
55. Fridell, Y. W., et al., *GAS6 induces Axl-mediated chemotaxis of vascular smooth muscle cells.* J Biol Chem, 1998. 273(12): p. 7123-6.
56. Nakano, T., et al., *Prevention of growth arrest-induced cell death of vascular smooth muscle cells by a product of growth arrest-specific gene, gas6.* FEBS Lett, 1996. 387 (1): p. 78-80.
57. McCloskey, P., et al., *GAS6 mediates adhesion of cells expressing the receptor tyrosine kinase Axl.* J Biol Chem, 1997. 272(37): p. 23285-91.
58. Avanzi, G. C., et al., *GAS6 inhibits granulocyte adhesion to endothelial cells.* Blood, 1998. 91(7): p. 2334-40.
59. Augustine, K. A., et al., *Noninsulin-dependent diabetes mellitus occurs in mice ectopically expressing the human Axl tyrosine kinase receptor.* J Cell Physiol, 1999. 181(3): p. 433-47.
60. Katagiri, M., et al., *Mechanism of stimulation of osteoclastic bone resorption through Gas6/Tyro 3, a receptor tyrosine kinase signaling, in mouse osteoclasts.* J Biol Chem, 2001. 276(10): p. 7376-82.
61. Tisi, D., et al., *Structure of the C-terminal laminin G-like domain pair of the laminin alpha2 chain harbouring binding sites for alpha-dystroglycan and heparin.* Embo J, 2000. 19(7): p. 1432-40.
62. Berman, H. M., et al., *The Protein Data Bank.* Nucleic Acids Res, 2000. 28(1): p. 235-42.
63. Hoven, M. Y., et al., *Detection and isolation of antigen-specific B cells by the fluorescence activated cell sorter (FACS).* J Immunol Methods, 1989. 117(2): p. 275-84.
64. Cote, et. al., *Monoclonal antibodies and cancer therapy.* Alan R. Liss, 1985: p. 77.
65. Knappik, A., et al., *Fully synthetic human combinatorial antibody libraries (HuCAL) based on modular consensus frameworks and CDRs randomized with trinucleotides.* J Mol Biol, 2000. 296(1): p. 57-86.
66. Krebs, B., et al., *High-throughput generation and engineering of recombinant human antibodies.* J Immunol Methods, 2001. 254(1-2): p. 67-84.
67. de St. Groth, F., et al., *Production of monoclonal Antibodies: Strategy and Tactics.* J Immunol Methods, 1980. 35: 1-21.

What is claimed is:

1. An isolated mammalian Gas6 monoclonal antibody or fragment thereof that (a) binds to the G-domain of Gas6, (b) binds to the polypeptides of SEQ ID NOS. 37 and 38 and (c) neutralizes Gas6 binding to Axl-Fc.

2. A pharmaceutical composition comprising the antibody of claim 1 and a pharmaceutically acceptable carrier.

3. An isolated mammalian GAS-6 antibody, comprising the heavy chain variable region SEQ ID No. 26 and the light chain variable region sequence of SEQ ID NO 28.

4. An isolated mammalian GAS-6 antibody, comprising (i) the heavy chain complementarity determining regions (CDR) comprising amino acid sequences of SEQ ID NOS:29-31; and (ii) the light chain complementarity determining regions comprising amino acids sequences of SEQ ID NOS:32-34.

5. The GAS-6 antibody according to any one of claims 1, 2, 3 or 4, wherein said antibody binds GAS-6 with an affinity of at least one selected from at least $10^{-9}$ M, at least $10^{-10}$ M, at least $10^{-11}$ M, or at least $10^{-12}$ M.

* * * * *